(12) United States Patent
Valtakari et al.

(10) Patent No.: US 8,362,222 B2
(45) Date of Patent: *Jan. 29, 2013

(54) FUNGAL PROTEASE AND USE THEREOF

(75) Inventors: Leena Valtakari, Rajamäki (FI); Kari Juntunen, Espoo (FI); Susanna Mäkinen, Läyliäinen (FI); Pentti Ojapalo, Tuusula (FI); Marja Paloheimo, Vantaa (FI)

(73) Assignee: AB Enzymes Oy, Rajamaki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 12/803,456

(22) Filed: Jun. 28, 2010

(65) Prior Publication Data

US 2011/0008870 A1    Jan. 13, 2011

Related U.S. Application Data

(60) Provisional application No. 61/270,418, filed on Jul. 8, 2009.

(30) Foreign Application Priority Data

Jul. 8, 2009  (FI) ..................................... 20095779

(51) Int. Cl.
*C07H 21/04* (2006.01)
(52) U.S. Cl. .................................................... 536/23.2
(58) Field of Classification Search .......................... None
See application file for complete search history.

(56) References Cited

U.S. PATENT DOCUMENTS

| | | | |
|---|---|---|---|
| 3,652,399 | A | 3/1972 | Isono et al. |
| 5,288,627 | A | 2/1994 | Nielsen et al. |
| 5,770,418 | A | 6/1998 | Yaver et al. |
| 5,843,745 | A | 12/1998 | Berka et al. |
| 5,962,765 | A | 10/1999 | St. Leger et al. |
| 6,573,086 | B1 | 6/2003 | Emalfrak et al. |
| 6,682,924 | B1 | 1/2004 | Sierkstra et al. |
| 2004/0023355 | A1 | 2/2004 | Sierkstra et al. |
| 2010/0120649 | A1 | 5/2010 | Andersen |
| 2011/0003729 | A1 | 1/2011 | Juntunen et al. |
| 2011/0008870 | A1 | 1/2011 | Makinen et al. |
| 2011/0028375 | A1 | 2/2011 | Juntunen et al. |
| 2012/0107905 | A1 | 5/2012 | Juntunen et al. |

FOREIGN PATENT DOCUMENTS

| | | |
|---|---|---|
| EP | 0244234 | 11/1987 |
| EP | 0352244 A2 | 1/1990 |
| EP | 0290567 | 6/1992 |
| EP | 0290569 | 6/1992 |
| EP | 0519229 | 12/1992 |
| EP | 0519229 A2 | 12/1992 |
| EP | 0 479 870 | 10/2000 |
| EP | 1347045 | 9/2003 |
| EP | 1464626 A2 | 10/2004 |
| EP | 1870453 A1 | 12/2007 |
| EP | 1 009 815 | 1/2008 |
| EP | 1464626 B1 | 11/2009 |
| WO | WO88/03946 | 6/1988 |
| WO | 88/07581 | 10/1988 |
| WO | WO89/04361 | 5/1989 |
| WO | 89/06270 | 7/1989 |
| WO | WO92/03529 | 3/1992 |
| WO | WO92/05239 | 4/1992 |
| WO | WO92/18599 | 10/1992 |
| WO | WO94/25583 | 11/1994 |
| WO | WO96/18722 | 6/1996 |
| WO | WO97/02753 | 1/1997 |
| WO | WO97/08325 | 3/1997 |
| WO | WO97/28243 | 8/1997 |
| WO | WO98/20116 | 11/1997 |
| WO | 02/08398 | 1/2002 |
| WO | WO2006/073839 | 7/2006 |
| WO | WO2006073839 | 7/2006 |
| WO | WO 2007/145963 | 12/2007 |
| WO | WO2008/045148 | 4/2008 |
| WO | 2009/096916 | 8/2009 |
| WO | 2010/039840 | 4/2010 |
| WO | 2010/125174 | 11/2010 |
| WO | 2010/125175 | 11/2010 |
| WO | 2011/003968 | 1/2011 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Geremia et al, Molecular characterization of the proteinase-encoding gene, prb1, related to mycoparasitism by *Trichoderma harzianum* Mol Microbiol May 1993;8(3):603-613.*
UniProt database Acc# Q86ZV3_TRIHM from Steyaert et al, Mycologia 96:1245-1252(2004). Alignment with SEQ ID No. 10.*
GenBank Acc# AAA34209 from Geremia et al, Mol Microbiol May 1993;8(3):603-613. Alignment with SEQ ID No. 10.*
USPTO in house alignment Q86ZV3_TRIHM from Steyaert et al, Mycologia 96:1245-1252 (2004). Alignment with SEQ ID No. 10.*
USPTO in house alignment AAA34209 from Geremia et al, Mol Microbiol May 1993;8(3):603-613. Alignment with SEQ ID No. 10.*
Geremia, R. et al. 1993 Molecular characterization of the proteinase-encoding gene . . . Mol. Microb. 8(3), 603-613.
Steyaert, J. M. et al. 2004. Co-expression fo two genes, a chitinase (chit42) and proteinase (prb1) . . . Mycologia 96(6): 1245-1252.
Suarez, M.B. 2007. Characterization of genes encoding novel peptidases in . . . Curr. Genet. 51:331-342.

(Continued)

*Primary Examiner* — Sheridan Swope
(74) *Attorney, Agent, or Firm* — Fish & Richardson P.C.

(57) ABSTRACT

The present invention is related to a fungal serine protease enzyme useful in modification, degradation or removal of proteinaceous material, which enzyme comprises an amino acid sequence of the mature Tr Prb1 enzyme having an amino acid sequence of SEQ ID NO: 10 or a variant thereof having similar activity. The serine protease is obtainable from *Trichoderma*. Also disclosed are nucleic acid sequences encoding said protease, such as plasmid pALK2650 comprising the nucleotide sequence SEQ ID NO: 10 of the full length enzyme deposited in *E. coli* RF8052 under accession number DSM 22635. Said protease is useful as an enzyme preparation applicable in detergent compositions and for treating fibers, for treating wool, for treating hair, for treating leather, for treating food or feed, or for any applications involving modification, degradation or removal of proteinaceous material at low or moderate temperature ranges.

28 Claims, 33 Drawing Sheets

OTHER PUBLICATIONS

Dienes et al. 2007. Identification of a trypsin-like serine protease from *Thricoderma reesei* GM9414. Enzyme and Microb. Techn. 40: 1087-1094.
Database UniProt (online) May 29, 2007. Sub-name: Full-Serin endopeptidase. Accession No. A4V8W7.
Database UniProt (Online) Jun. 1, 2003. Subname: Full-alkaline proteinase. Accession No. Q86ZV3.
Database UniProt (Online) Jun. 16, 2009. RecName: Full-Alkaline proteinase. Accession No. Q03420.
Database UniProt (Online) Feb. 10, 2009. Subname: Full Extracellular serine protease. Accession No. Q874K4.
Maladier L. et al.1989 Cloning of the nitrate reductase gene (niaD) of *Aspergillus nidulans* . . . Gene 78: 147-157.
Laemmli, U.K. 1970 Cleavage of structural proteins during the assembly . . . NAture 227915): 680-685.
Karhunen, T. et al. 1993. High frequency one-step gene replacement in *Trichoderma* . . . Mol Gen Genet 241:515-522.
Kalisz, H. M. 1988. Microbial proteases. Advances in Biochemical engineering / Biotechnology. vol. 36 pp. 1-65.
Joutsjoki, V. V. et al. 1993. Transformation of *Trichoderma reesei* with the *Hormoconis* . . . Curr Genet 24: 223-228.
Gurr, S. J. et al.1987 The structure and organization of nuclear genes . . . pp. 93-139. In (JR Kinghorn, ed.) Gene Structure in Eukaryotic Microbes.
Geremia, R.A. et al. 1993. Molecular characterization of the proteinase-encoding . . . Molec. Microbiol. 8(3):603-613.
Kredics, L. et al. 2005 Extracellular proteases of *Trichoderma* species. Acta Microbiologica et Immunologica Hungarica. 52(2): 169-184.
Edman P. and Begg, G. 1967.A protein sequenator Eur. J. Biochem. 1: 80-91.
Cherry, J.R. and Fidantsef, A. L. 2003. Directed evolution of industrial enzymes . . . Curr. Opinion in biotechnol. 14: 438-443.
Chen, Y-J and Inoye, M. 2008. The intramolecular chaperone mediated protein folding. Curr. Opinion in Structural Biology. 18:765-770.
Bolton, E.T. and McCarthy B.J. 1962. A general method for the isolation of RNA . . . Proc Nat. A. S. 48: 1390-1397.
Anwar, A. and Saleemuddin, M. 1998 Alkaline proteases: a review. Bioresource Technology 64: 175-183.
AMFEP list of commercial enzymes. www. amfep.org updated Nov. 30, 2007.
Altschul S.F. et al. 1990 Basic Local Alignment Search Tool J. Mol. Biol 215:403-410.
Gupta, R. et al. 2002. An overview on fermentation, downstream processing . . . Appl. Microbiol Biotechnol. 60:381-395.
Pozo, M.J. 2004. Functional analysis of tvsp1, a serine protease-encoding gene . . . Fungal Genetics and Biology 41: 334-348.
Steyaert, J.M. 2004 Co-expression of two genes, a chitinase (chit 42) and proteinase (prb1) implicated in . . . Mycologia 96(6):1245-1252.
Manonmani, H.K. and Joseph, R. 1993. Purification and properties of an extracellular proteinase . . . Enzyme Microb. Technol. 15: 624-628.
Martinez et al. 2008. Gene sequencing and analysis of the biomass-degrading fungus *Trichoderma* . . . Nature Biotech 26:553-560.
Suarez, M. B. et al. 2007. Characterization of genes encoding novel peptidases in the biocontrol fungus . . . Curr. Genet. 51:331-342.
Shimogaki, H. 1991. Purification and properties of a novel Surface-active agent . . . Agric. Biol. Chem 55(9): 2251-2258.
Dienes, D. et al. 2007. Identification of a trypsin-like protease from *Trichoderma reesei* QM944. Enzyme and Microbial Tech. 40:1087-1094.
Rao, M.B et al. 1998. Molecular and Biotechnological aspects of microbial proteases. Microbiol. and Mol. Biol. Rev. 62(3): 597-635.
Raeder, U. et al. 1985. Rapid Preparation of DNA from filamentous fungi. Lett. Appl. Microbiol. 1: 17-20.
Antal, ZS. et al. 2000. Colony growth, in vitro antagonism and secretion of extracellular enzymes in . . . Mycol. Res. (5):545-549.
Penttila, M. et al. 1987 A versatile transformation system for the cellulolytic filamentous fungus . . . Gene 61: 155-164.
Nielsen, H. et al. 1997. Identification of procaryotic and eucaryotic signal peptides and . . . Protein Engineering 10(1): 1-6.
Nielsen, H. et al. 1998. Prediction of signal peptides and signal anchors by a hidden . . . Proc. 6th Intl. Conf. of Intelligent systems. pp. 122-130.
Mauer K-H. 2004. Detergent proteases. Current opinion in Biotechnology. 15: 330-334.
Paloheimo, M. et al. 2003. High-yield production of bacterial xylanase in filamentous . . . Appl. Env. Microb. 69(12) 7073-7082.
Gasteiger, E. et al. 2003. ExPASY: the proteomics server . . . Nucleic Acids Res. 31(13): 3784-3788.
Abu-Shady, M. R. et al., "Production, Partial Purification and Some Properties of Thermostable Alkaline Protease from Malbranchea sulfurea and its Compatibility with Commercial Detergents", Afr. J. Mycol. and Biotech., vol. 9, No. 3, (2001), pp. 17-26.
Banerjee, U. C. et al., "Thermostable alkaline protease from *Bacillus brevis* and its characterization as a laundry detergent additive", Process Biochemistry, vol. 35, (1999), pp. 213-219.
EMBL database (online), Database Accession No. DR657362, Jul. 14, 2005, from Brown, D. W., et al., "Analysis of 87,000 expressed sequence tags reveals alternatively spliced introns in multiple genes of the fumonisin gene cluster", (Unpublished) (1 page).
EMBL database (online), Database Accession No. BI750343, Jun. 15, 2004, from Harris, L. J. et al. "Expressed Sequence Tags from *Fusarium graminearum* mycelium", (Unpublished) (1 page).
EMBL database (online), Database Accession No. AM294980, Apr. 20, 2007, from Suarez, M. B., et al., "Characterization of genes encoding novel peptidases in the biocontrol fungus *Trichoderma harzianum* CECT 2413 using the TrichoEST functional genomics approach", Curr. Genet. vol. 51, No. 5, (2007), pp. 331-342 (2 pages).
European Patent Office database (online), Database Accession No. GM007507, Nov. 20, 2008, from Madison, E.L., "Protease screening methods and proteases identified thereby"; Sequence 313 from Patent No. WO2008045148-A1, Apr. 17, 2008 (1 page).
European Patent Office database (online), Database Accession No. HC687299, May 10, 2010, from Shasky, J. et al., "Methods for producing polypeptides in enzyme-deficient mutants of *Fusarium venenatum*; Sequence 84 from Patent WO2010039840", Patent No. WO2010039840-A1, Apr. 8, 2010 (1 page).
Gaucher, G. M. et al. "567. Thermomycolin", Handbook of Proteolytic Enzymes, (2004), pp. 1834-1835.
Gayle, R. B. et al., "Identification of Regions in Interleukin-1 α Important for Activity", The Journal of Biological Chemistry, vol. 268, No, 29, (1993), pp. 22105-22111.
Genbank database, Database Accession No. AAA34209.1, May 28, 1993, from Geremia, R.A. et al., "Molecular Characterization of the proteinase-encoding gene, prb1, related to mycoparasitism by *Trichoderma harzianum*", Molecular Microbiology, vol. 8, No. 3, (1993), pp. 603-613 (3 pages).
Kelly, J. M. et al., "Transformation of *Aspergillus niger* by the amdS gene of *Aspergillus nidulans*", The EMBO Journal, vol. 4, No. 2, (1985), pp. 475-479.
Maurer, K. H. et al. "Enzymes, Detergent", Encyclopedia of Industrial Biotechnology: Bioprocess, Bioseparation, and Cell Technology (Michael C. Flickinger, ed.), John Wiley & Sons, Inc., (2010), pp. 1-17.
NCBI REFSEQ Database (online), Database Accession No. XP_383491, Apr. 9, 2008, No Author Found, Hypothetical protein FG03315.1 (*Gibberella zeae* PH-1) (1 page).
Ong, P. S. et al., "Production, purification and characterization of thermomycolase, the extracellular serine protease of the thermophilic fungus *Malbranchea pulchella* var. sulfurea", Can. J. Microbiol., vol. 22, (1975), pp. 165-175.
Poutanen, P. et al., "Use of matrix-assisted laser desorption/ionization time-of-flight mass mapping and nanospray liquid chromatography/electrospray ionization tandem mass spectrometry sequence tag analysis for high sensitivity identification of yeast proteins separated by two-dimensional gel electrophoresis", Rapid Communications in Mass Spectrometry, vol. 15, No. 18, (2001), pp. 1685-1962.
Sambrook, J. and Russell, D. W., Molecular Cloning, a Laboratory Manual, Cold Spring Harbor Laboratory, New York, US, (2001), pp. 6.51, 6.52, 11.27.
Shevchenko, A. et al., "Mass spectrometric sequencing of proteins from silver-stained polyacrylamide gels", Anal. Chem., Vo. 68, No. 5 (1996), pp. 850-858.

Siezen, R. J. et al., "Subtilases: The superfamily of subtilisin-like serine proteases", Protein Science, vol. 6, (1997), pp. 501-523 (total pp. 30).

UNIPROT database (online), Database Accession No. C7ZKJ9, Oct. 13, 2009, from Coleman, J.J. et al, "The genome of *Nectria haematococca*: contribution of supernumerary chromosomes to gene expansion", PLoS Genet. 5: E1000618-E1000618, (2009), (1 page).

UNIPROT database (online), Database Accession No. C9SL49, Nov. 24, 2009, from Ma, L.-J.J., et al, "Annotation of *Verticillium albo-atrum* VaMs. 102.", Submitted (May 2008) to the EMBL/GenBank/DDBJ databases, (1 page).

UNIPROT database (online), Database Accession No. E3Q3S5, Jan. 11, 2011, from Vaillancourt, L. et al., "The genome sequence of *Glomerella graminicola* strain M1.001.", Submitted (Jun. 2009) to the EMBL/GenBank/DDBJ databases, (1 page).

UNIPROT database (online), Database Accession No. C7YXB3, Oct. 13, 2009, from Coleman, J. J. et al., "The genome of *Nectria haematococca*: contribution of supernumerary chromosomes to gene expansion", PLoS Genet. 5: E1000618-E1000618, (2009), (1 page).

UNIPROT database (online), Database Accession No. A5JS74, Jun. 26, 2007, from Gao, L. et al., "Gene cloning of serine protease from *Hirsutella minnesotania*", Submitted (Apr. 2007) to the EMBL/GenBank/DDBJ databases, (1 page).

UNIPROT database (online), Database Accession No. Q69IF7, Sep. 13, 2004, from Hane, J.K, et al., "Dothideomycete-plant interactions illuminated by genome sequencing and EST analysis of the wheat pathogen *Stagonospora nodorum*.", Plant Cell, vol. 19, (2007), pp. 3347-3368, (1 page).

International Search Report from corresponding PCT Application No. PCT/EP2011/068837 dated Dec. 15, 2011, (6 pages).

D'Acunzo, F. et al., "Oxidation of phenols by laccase and laccase-mediator systems", Eur. J. Biochem., vol. 269, (2002), pp. 5330-5335.

Fabbrini, M. et al., "Comparing the catalytic efficiency of some mediators of lacasse", Journal of Molecular Catalysis B: Enzymatic, vol. 16, (2002), pp. 231-240.

Liao, J. et al., "Engineering proteinase K using machine learning and synthetic genes", BMC Biotechnology, vol. 7, No. 16, (2007), pp. 1-19.

UNIPROT 201110 database Acc# A4V8W7_TRIHA from Suarez et al., Curr. Genet. May 2007; 51(5):331-42, Epub Apr. 6, 2007., Alignment with SEQ ID No. 18 of U.S. Appl. No. 12/799,638 (2 pages).

Search Report issued in the corresponding Finnish Patent Application No. 20106135 dated May 13, 2011 (1 page).

Guo, H.H. et al., "Protein tolerance to random amino acid change", PNAS, vol. 101, No. 25, (2004), pp. 9205-9210.

International Search Report from PCT Application No. PCT/EP2011/068837 dated Dec. 15, 2011, (6 pages).

\* cited by examiner

FIG. 1

```
  1  atggccagcc ttcgtcgcct tgccctctat ctcggagccc tgctcccggc tgttctggcc
  1   m  a  s   l  r  r   l  a  l  y   l  g  a   l  l  p   a  v  l  a 61  gctcctgctg tcaattacaa gctgcctgaa gctgttccca acaagttcat tgtcactctc
 21   a  p  a   v  n  y   k  l  p  e   a  v  p   n  k  f   i  v  t  l 121  aaagatggtg cctctgttga tacagactct caccttacat gggtgaaaga ccttcacagg
 41   k  d  g   a  s  v   d  t  d  s   h  l  t   w  v  k   d  l  h  r 181  cgctcactcg gcaagcgcag cactgctggt gttgagaaga cgtacaacat cgacagctgg
 61   r  s  l   g  k  r   s  t  a  g   v  e  k   t  y  n   i  d  s  w 241  aatgcctatg ctggcgagtt cgatgaagaa accgttaagc agatcaaggc gaatcccgac
 81   n  a  y   a  g  e   f  d  e  e   t  v  k   q  i  k   a  n  p  d 301  gtaagtattt gccctactgt tggacgagat gccaatgttc cattgcgaaa ttctaatgag 361  cataccaggt tgcttccgta gagccagact acatcatgtg gttgtctgac attgtggaag
101                v  a  s  v   e  p  d   y  i  m   w  l  s   d  i  v  e 421  acaagcgtGC TTTGACCACT CAGACTGGCG CCCCCTGGGG ACTCGGCACT GTCTCCCACC
118   d  k  r   A  L  T  T   Q  T  G   A  P  W   G  L  G  T   V  S  H 481  GCACACCCGG CTCAACTAGC TACATCTATG ACACTTCGGC TGGTAGCGGA ACATTCGCCT
138   R  T  P   G  S  T  S   Y  I  Y   D  T  S   A  G  S  G   T  F  A 541  ATGTTGTTGA CTCTGGAATC AACATTGCTC ACCAGCAATT CGGCGGACGT GCCAGCCTCG
158   Y  V  V   D  S  G  I   N  I  A   H  Q  Q   F  G  G  R   A  S  L 601  GCTACAACGC CGCTGGTGGA GATCATGTCG ACACTCTCGG CCACGGCACG CACGTTTCCG
178   G  Y  N   A  A  G  G   D  H  V   D  T  L   G  H  G  T   H  V  S 661  GAACTATCGG TGGCTCTACC TATGGTGTTG CTAAGCAGgt aagctgcttc attatacttc
198   G  I  I   G  G  S  T   Y  G  V   A  K  Q 721  ttcctttgca gtgcgggcct tgagcacgcc gggctgactc tgtaacgaaa gGCCAGCTTA
211                                                            A  S  L 781  ATCTCCGTCA AGGTCTTCCA GGGCAACAGC GCCAGCACCT CGGTCATCCT TGACGGCTAT
214   I  S  V   K  V  F  Q   G  N  S   A  S  T   S  V  I  L   D  G  Y 841  AATTGGGCCG TGAACGACAT TGTCTCCCGC AACCGCGCCA GCAAGTCTGC CATCAACATG
234   N  W  A   V  N  D   I  V  S  R   N  R  A   S  K  S   A  I  N  M 901  TCTCTCGGTG GCCCGGCCTC TTCCACCTGG GCTACGGCGA TCAATGCAGC CTTTAACAAG
254   S  L  G   G  P  A  S   S  T  W   A  T  A   I  N  A   A  F  N  K 961  GGCGTCCTGA CGATCGTGGC CGCCGGCAAT GGTGACGCTC TTGGAAACCC TCAGCCTGTC
274   G  V  L   T  I  V   A  A  G  N   G  D  A   L  G  N   P  Q  P  V 1021 TCCAGTACTT CTCCAGCCAA TGTGCCCAAC GCCATCACCG TCGCAGCCCT TGACATTAAC
294   S  S  T   S  P  A   N  V  P  N   A  I  T   V  A  A   L  D  I  N 1081 TGGCGCACCG CTTCCTTCAC CAATTATGGT GCTGGCGTTG ACGTCTTCGC TCCTGGTGTC
314   W  R  T   A  S  F   T  N  Y  G   A  G  V   D  V  F   A  P  G  V 1141 AACATCCTGT CTTCGTGGAT CGGCTCTAAC ACTGCCACAA ACACGATTAG CGGCACCTCC
334   N  I  L   S  S  W   I  G  S  N   T  A  T   N  T  I   S  G  T  S
```

FIG. 1 (continued)

```
1201 ATGGCCACTC CTCACGTTGT CGGCCTCGCT CTTTACCTGC AGGCTCTTGA GGGCCTTAGC
 354  M  A  T     P  H  V  V     G  L  A     L  Y  L     Q  A  L  E     G  L  S

1261 ACCCCGACTG CTGTAACCAA CCGCATCAAG GCCTTGGCTA CTACTGGACG CGTCACCGGC
 374  T  P  T     A  V  T  N     R  I  K     A  L  A     T  T  G  R     V  T  G

1321 AGTCTGAATG GCAGCCCCAA CACTCTCATC TTCAACGGGA ACAGTGCTTA A   (SEQ ID NO:5)
 394  S  L  N     G  S  P  N     T  L  I     F  N  G     N  S  A  -      (SEQ ID NO:6)
```

FIG. 2

```
  1  atgaccagct tccgccgtct tgctctcgct cttggagctc tgctccctgc agtcctcgcc
  1   m  t  s  f  r  r  l  a  l  a  l  g  a  l  l  p  a  v  l  a 61  gctcctactg agaagcgaca ggaactcact gccgcgcctg acaagtacat catcactctc
 21   a  p  t  e  k  r  q  e  l  t  a  a  p  d  k  y  i  i  t  l 121  aagcccgagg ctactgagaa caagatcgag gctcacttga actgggtcag cgatgtccac
 41   k  p  e  a  t  e  n  k  i  e  a  h  l  n  w  v  s  d  v  h 181  cgccgcagcc tgaacaagcg tgacacttct ggtgttgaga agaagttcaa catcagcagc
 61   r  r  s  l  n  k  r  d  t  s  g  v  e  k  k  f  n  i  s  s 241  tggaacgcct actctggcga gttcgacaag gctaccattg atgagatcaa gaagagcccc
 81   w  n  a  y  s  g  e  f  d  k  a  t  i  d  e  i  k  k  s  p 301  gaggttgctt tcgtcgagcc tgactacact gtctacctcg acttcgagac cgaactcact
101   e  v  a  f  v  e  p  d  y  t  v  y  l  d  f  e  t  e  l  t 361  gaccgtGCTC TGACCACCCA GAGCGGCGCT CCTTGGGGTC TCGCCTCCAT CTCCCGCCGA
121   d  r  A  L  T  T  Q  S  G  A  P  W  G  L  A  S  I  S  R  R 421  ACCTCCGGTG GCAGCACCTA CACCTACGAC ACCACTGCCG GCTCCGGTTC TTACGGATAC
141   T  S  G  G  S  T  Y  T  Y  D  T  T  A  G  S  G  S  Y  G  Y 481  GTCGTTGACA GCGGCATCAA CGTCAACCAC CGAGACTTCG GTGGCCGTGC TTCTCTCGGT
161   V  V  D  S  G  I  N  V  N  H  R  D  F  G  G  R  A  S  L  G 541  TACAACGCTG CCGGTGGTTC CCACGTCGAC ACCCTGGGCC ACGGTACCCA CGTTGCTGGA
181   Y  N  A  A  G  G  S  H  V  D  T  L  G  H  G  T  H  V  A  G 601  ACCATTGCTT CTTCCACCTA CGGTGTTGCC AAGGCTgtaa gtaaacccca cattatatgg
201   T  I  A  S  S  T  Y  G  V  A  K 661  tagcatctga actttatact tactatcttt agGCCAACGT CATCTCTGTC AAGGTCTTCA
213                                    A  N  V  I  S  V  K  V  F 721  CTGGCAACAG TGCCTCTACC TCCACTATCC TCGCTGGTTT CAACTGGGCT GTCAACGACA
222   T  G  N  S  A  S  T  S  T  I  L  A  G  F  N  W  A  V  N  D 781  TCACTTCCAA GGGCCGTGCT GGTCGCTCTG TCATCAACAT GTCTCTCGGC GGTCCCTCTG
242   I  T  S  K  G  R  A  G  R  S  V  I  N  M  S  L  G  G  P  S 841  CTCAGACCTG GACCACTGCT ATCAACGCTG CCTACAACTC TGGTGTCCTC TCCGTTGTTG
262   A  Q  T  W  T  T  A  I  N  A  A  Y  N  S  G  V  L  S  V  V 901  CTGCCGGTAA CGGTGACGAT TTCGGCCGCC CTCTTCCCGT CTCTGGCCAG TCTCCTGCCA
282   A  A  G  N  G  D  D  F  G  R  P  L  P  V  S  G  Q  S  P  A 961  ACGTCCCCAA CGCTCTGACC GTTGCTGCCA TTGACTCCAG CTGGCGCACT GCCTCTTTCA
302   N  V  P  N  A  L  T  V  A  A  I  D  S  S  W  R  T  A  S  F 1021 CCAACTACGG TGCCGGTGTT GATGTCTTCG CCCCTGGTGT CGGCATCCTC TCCACCTGGT
322   T  N  Y  G  A  G  V  D  V  F  A  P  G  V  G  I  L  S  T  W 1081 ACACCTCCAA CACTGCTACC AACTCCATCA GCGGTACCTC CATGGCCTGC CCTCACGTTG
342   Y  T  S  N  T  A  T  N  S  I  S  G  T  S  M  A  C  P  H  V
```

FIG. 2 (continued)

```
1141 CTGGTCTTGC TCTCTACCTC CAGGTTCTCG AGGGTCTTTC CACCCCTGCT GCCGTCACCA
 362  A  G  L    S  L  Y  L    Q  V  L  E    G  L  S  T    P  A  A  V    T

1201 ACCGGCATCAA GGCTCTTGCT ACCACTGGCC GTGTCACTGG CACCCTCAAC GGCAGCCCCA
 382  N  R  I    K  A  L  A    T  T  G  R    V  T  G  T    L  N  G  S    P

1261 ACCTGATCGC CTTCAACGGT GCCTCTACTT AA           (SEQ ID NO:11)
 402  N  L  I    A  F  N  G    A  S  T     -      (SEQ ID NO:12)
```

Microscale tests (pH 9 buffer, 10°C, 60 min)

Microscale tests (pH 9 buffer, 20°C, 60 min)

Microscale tests (pH 9 buffer, 30°C, 60 min)

Microscale tests (pH 9 buffer, 40°C, 60 min)

Microscale tests (pH 9 buffer, 50°C, 60 min)

Microscale test (pH 9 buffer 60°C, 60 min)

Microscale tests with Ariel Sensitive 3.3 g/l
(Art 117, 30°C, 60 min, pH ca. 7.9)

Microscale tests with Erisan detergent 3.3 g/l
(Art 117, 30°C, 60 min, pH ca. 8.2)

Microscale tests with Base detergent 5 g/l
(Art 117, 30°C, 60 min, pH ca. 7.5)

Microscale tests with Base detergent 3.3 g/l
(Art 117, 30°C, 60 min, pH ca. 7.4)

Microscale tests with Base detergent 1 g/l
(Art 117, 30°C, 60 min, pH ca. 7.3)

Microscale tests with Base detergent 3.3 g/l
(Art 117, 20°C, 60 min)

Microscale tests with Base detergent 3.3 g/l
(Art 117, 10°C, 60 min)

Microscale tests with detergent Art. 601, 3.3 g/l
(Art 117, 40°C, 60 min, pH ca. 10)

Microscale tests with detergent Art. 601, 3.3 g/l
(Art 117, 50°C, 60 min, pH ca. 10)

Blood/milk/ink, PE+CO, EMPA Art 117

Blood/milk/ink,CO, EMPA Art 116

FIG. 11C
Blood/milk/ink,PE+CO, CFT/PC-05-014
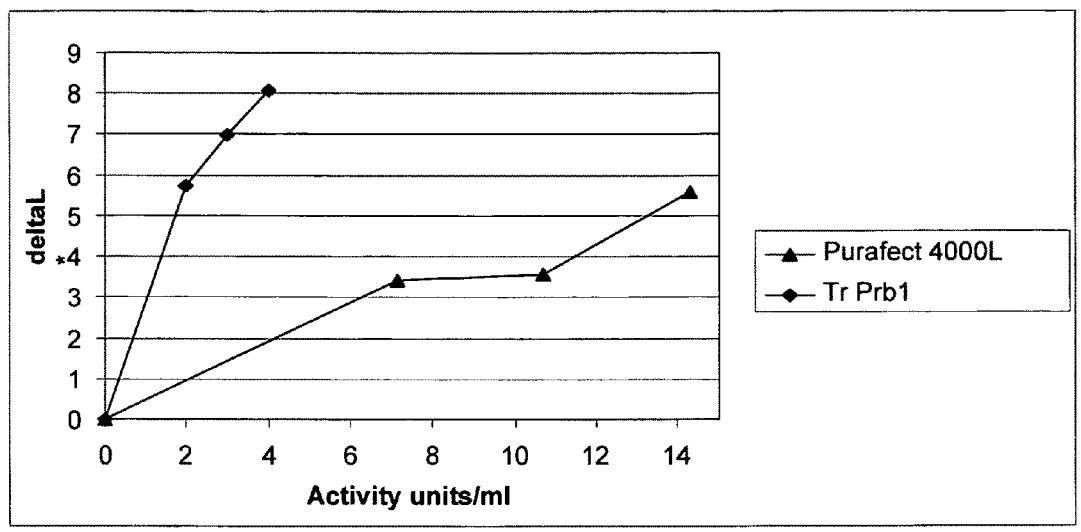
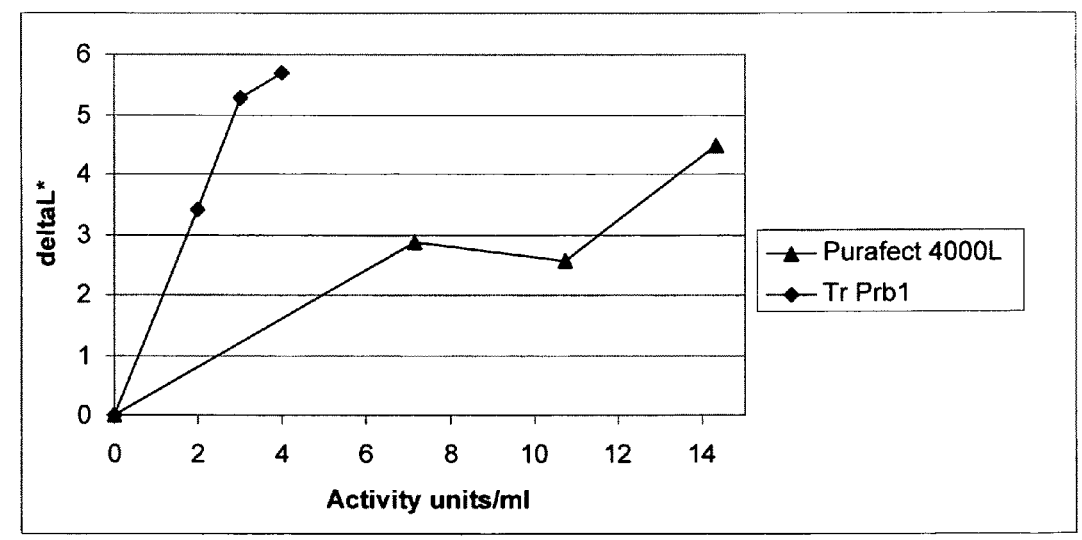
FIG. 11D
Blood/milk/ink,CO, CFT/C-05-059

FIG. 11E
Cocoa, EMPA Art 112
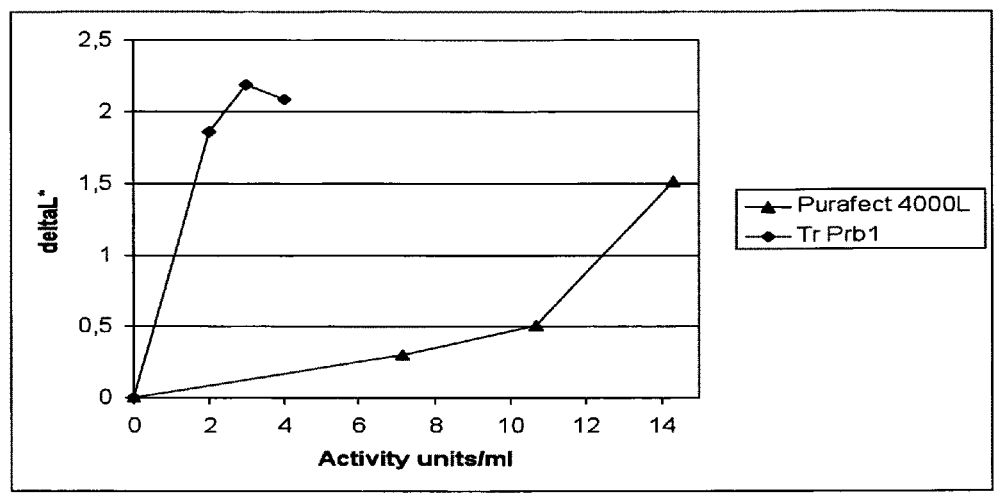
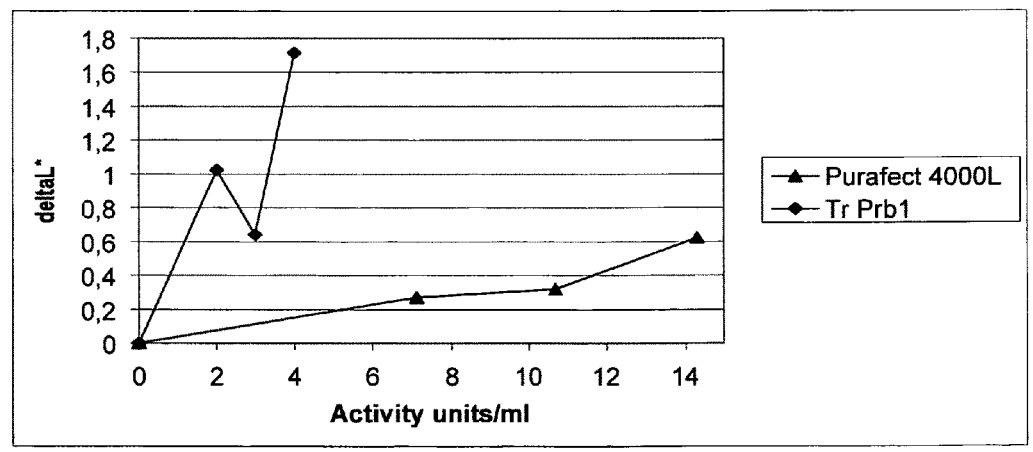
FIG. 11F
Chocolate/milk/pigment, CFT/C-03-

Groundnut oil/milk, CFT/C-10-186b

Grass, CFT/CS-08-069

Egg Yolk/pigment, CFT-CS-38-010

Blood/milk/ink, PE+CO, EMPA Art 117

Cocoa, EMPA Art 112

FUNGAL PROTEASE AND USE THEREOF

PRIORITY

This application claims priority of U.S. provisional application No. 61/270,418 filed on Jul. 8, 2009 and of Finnish national application number FI20095779 filed on Jul. 8, 2009.

SEQUENCE LISTING

This application contains sequence data provided on a computer readable diskette and as a paper version. The paper version of the sequence data is identical to the data provided on the diskette.

FIELD OF THE INVENTION

The present invention relates to a fungal serine protease enzyme useful in various industrial applications, particularly in laundry and dish-washing detergents, where performance of said enzyme at low or moderate temperature ranges is advantageous. The invention relates to an isolated nucleic acid molecule encoding said enzyme, a recombinant vector, a host cell for producing said enzyme, an enzyme composition comprising said enzyme as well as a process for preparing such composition. This invention relates also to various uses of said enzyme or compositions comprising said enzyme.

BACKGROUND

Microbial extracellular proteases account for a major part, more than one third, of the total worldwide industrial enzyme sales (Cherry and Fidantsef, 2003). Approximately 90% of the commercial proteases are detergent enzymes (Gupta et al., 2002). Other applications include such as food, feed, leather, pharmaceuticals, diagnostics, waste management and silver recovery.

The commercial detergent preparations currently in use comprise alkaline serine proteases originating from *Bacillus* species (Maurer, 2004). Variants of the *Bacillus* enzymes with improved catalytic efficiency and/or better stability towards temperature, oxidizing agents and various washing conditions have been developed through site-directed and/or random mutagenesis. Examples of commercial proteases are such as subtilisin Carlsberg (Alcalase®, Novozymes, DK), subtilisin 309 (Savinase®, Novozymes, DK), Subtilisin 147 (Esperase®, Novozymes, DK), Kannase® (Novozymes, DK); Purafect® (Genencor Inc., USA), Purafect® Ox (Genencor Inc., USA), Properase® (Genencor Inc., USA), and the BLAP S and X series (Henkel, Del.).

Alkaline serine protease genes and enzymes (EC 3.4.21) have been characterized also from eukaryotic organisms, including yeast and filamentous fungi. The use of the fungal serine proteases is known from several patent applications. For example, U.S. Pat. No. 3,652,399 and EP 519229 (Takeda Chemical Industries, Ltd., JP) disclose an alkaline protease from the genus *Fusarium* (teleomorph) or *Gibberella* (anamorph) particularly from *Fusarium* sp. S-19-5 (ATCC 20192, IFO 8884), *F. oxysporum* f. sp. *lini* (IFO 5880) or *G. saubinetti* (ATCC 20193, IFO6608), useful in the formulation of detergent and other cleanser compositions. WO1994025583 (NovoNordisk A/S, DK) discloses an active trypsin-like protease enzyme derivable from a *Fusarium* species, in particular a strain of *F. oxysporum* (DSM 2672), and the DNA sequence encoding the same. The amino acid sequence of a novel protease deriving from *Fusarium* sp. BLB (FERM BP-10493) is disclosed in WO 2006101140 (SODX Co. Ltd, Nakamura). Such detergent compositions may further comprise reversible protease inhibitors for stabilizing the enzyme(s) as disclosed in WO 1992003529 and WO 1992005239 (NovoNordisk A/S, DK) or the catalytically active amino acid sequence of a protease may be linked to a sequence comprising a cellulose binding domain as disclosed in WO 1997028243 (NovoNordisk A/S, DK).

The serine proteases may be used in applications alone or in combination with other hydrolyzing enzymes. For example, WO 88/03946 and WO 89/04361 (Novo Industri A/S, DK) disclose an enzymatic detergent additive and a detergent composition comprising a protease and a lipase, wherein the fungal protease is derived from *Fusarium*, particularly *F. oxysporum* or *F. solani*. WO 1997002753 (NovoNordisk A/S, DK) discloses a method for gentle cleaning of soiled process equipment using such a combination of a protease and a lipase. Combination of a cellulase and a protease, particularly a trypsin-like protease from *Fusarium* sp. DSM 2672 as a detergent additive or composition is disclosed in WO 1992018599 (NovoNordisk A/S, DK).

*Trichoderma* species have been described to secrete a wide variety of proteases (reviewed in Kredics et al., 2005). However, only few of them have been characterized. Isolation of a serine protease encoding gene, prb1, from the biocontrol strain *T. harzianum* (isolate later reclassified as *T. atroviride*) has been disclosed in Geremia et al. (1993). The *T. atroviride* prb1 gene sequence was used in cloning the prb1 gene from *T. hamatum* and *T. harzianum* (Steyaert et al., 2004) and the tvsp1 gene from *T. virens* (Pozo et al., 2004). The mature *T. atroviride* PRB1 and *T. virens* TVSP1 proteins were expected to have pIs at 8.98 and 9.2, respectively, and molecular weights of 29 kDa. They showed homology with several subtilisin-like serine proteases and were assigned to family S8 of serine proteases. The TrichoEST approach (Suarez et al. 2007) revealed four novel serine proteases P5431 (AM294975), P7129 (AM296482), P8048 (AM294978) and P10261 (AM294980) from a biocontrol fungus *T. harzianum* CECT 2413 belonging to S8A subfamily of proteases. The *T. reesei* genome project demonstrated presence of several genes encoding different types of proteases (Martinez et al., 2008; genome.jgi-psf.org/Trire2/Trire2.home.html). The homologue to the prb1 gene encodes a protein having ID 121495.

Characterization of the above *Trichoderma* serine proteases has been suggested to pave the way for identification of candidate biocontrol genes and improved commercial biocontrol agents. Their applications in other biotechnological processes have not been studied. The alkaline serine protease of *T. koningii* has been suggested to be applicable in detergent industry since crosslinking with glutaraldehyde resulted in an enzyme preparation stable over a wide range of temperature and pH resistant to inhibition by detergents (Manonmani and Joseph, 1993). However, the enzyme differs from the Prb1-type proteases due to its high molecular weight of 85 kDa. *Trichoderma* species, such as *T. reesei* QM9414 is known to secrete also a trypsin-like protease of family S1 having molecular weight of 25 kDa and pI of 7.3, and maximum activity at pH 8 and 50° C. (Dienes et al. 2007). EP 1347045 A1 discloses a family S1 serine protease from *T. harzianum*. Nucleic acid and amino acid sequences of acid protease NSP24 and NSP25 from *T. reesei* QM6a have been disclosed in WO 2006073839. The recombinantly produced NSP24 has utility, for example, in preparation of food and feed and in detergents.

Also, alkaline proteases from fungal species such as *Tritirachium* and *Conidiobolus* have been reported (reviewed in Anwar and Saleemuddin, 1998).

The socioeconomic challenges and governmental regulations have forced detergent industry to take in consideration many environmental aspects including not only the use of more lenient chemicals, which can be used in minor amounts and therefore leave less environmental waste trails, but also the need of energy saving. Detergent enzymes, particularly proteases, are important ingredient in detergent compositions. The need to save energy by decreasing the washing temperatures and the increased use of synthetic fibers which cannot tolerate high temperatures and current lifestyle have changed customer habits and created a demand for new enzymes, which are effective at low temperatures.

Despite the fact that numerous patent publications, reviews and articles have been published, in which serine proteases from various microorganisms, for example, the low temperature alkaline proteases from actinomycete *Nocardiopsis dassonvillei* (EP 0290567, Novo Nordisk A/S, DK) and fungal *Paecilomyces marquandii* (EP 0290569, Novo Nordisk A/S, DK) and the trypsin and chymotrypsin-like activities of cold-tolerant *Trichoderma* isolates (Antal et al., 2000) are disclosed, there is still a great need for alternative serine proteases, which are suitable for and effective in modifying, degrading and removing proteinaceous materials particularly in low or moderate temperature ranges and which are stable in the presence of detergents with highly varying properties.

Detergent industry is making great advances in adapting its new products to customers' habits and needs, the properties of new textile products and new washing machines. In order to fulfill all varying demands of detergent industry and governmental regulations, new serine protease ingredients for detergent compositions should be able to accomplish their tasks in wide pH and temperature ranges and remain stable in variety of conditions, including mechanical and chemical interventions in combination with a variety of different detergents. It is also desirable that the serine protease can be produced in high amounts, which can be cost-effectively down-stream processed, by easy separation from fermentation broth and mycelia.

SUMMARY OF THE INVENTION

The aim of the present invention is to provide a serine protease of fungal origin which shows broad substrate specificity, is active at broad pH ranges and has a broad temperature optimum, i.e. functions both at low and moderate temperatures. The serine proteases for laundry and dish detergents have to be stable also in the presence of detergents or to be compatible with detergents. Particularly, the object of the invention is to provide a serine protease, which is capable of effectively removing proteinaceous material, including stains in washing laundry and dishes, at lower temperatures than the present commercial enzyme preparations, thereby saving energy. The fungal serine protease can be produced in high-yielding fungal hosts and its down-stream processing, e.g. separation of fermentation broth and mycelia is easy to perform.

The present invention relates to a fungal serine protease enzyme which is applicable in modification, degradation or removal of proteinaceous materials at low or moderate temperature ranges. The enzyme has serine protease activity and comprises an amino acid sequence of the mature Tr Prb1 enzyme as defined in SEQ ID NO:10 or a variant thereof having similar properties. Preferably the enzyme is applicable as a detergent additive.

The enzyme of the invention is obtainable from a filamentous fungus *Trichoderma*, more preferably from *T. reesei*, most preferably from *T. reesei* QM6a strain (ATCC 13631, CBS 383.78, IMI 192654, IMI 45548 and T.V. B117). Preferably the enzyme has serine protease activity and comprises an amino acid sequence of the mature Tr Prb1 enzyme as defined in SEQ ID NO: 10.

The enzyme of the invention has a molecular mass between 25 and 35 kDa. The enzyme has optimal temperature at a range from 30° C. to 70° C. at pH 9. Said enzyme has pH optimum at the pH range of at least pH 6 to pH 11 at 50° C. The temperature and pH optima were determined using 15 min reaction time and casein as a substrate. The serine protease of the invention is capable in modifying, degrading or removing proteinaceous stains in the presence of detergent between 10° C. and 60° C.

Said enzyme is encoded by an isolated polynucleotide sequence, which encodes a polypeptide comprising an amino acid sequence of the mature Tr Prb1 enzyme as defined in SEQ ID NO: 10. Preferably, said mature enzyme is encoded by an isolated nucleic acid molecule comprising the nucleotide sequence SEQ ID NO: 9.

The fungal serine protease enzyme of the invention is encoded by an isolated polynucleotide sequence included in plasmid pALK2650 comprising the nucleotide sequence SEQ ID NO:5 deposited in *E. coli* RF8052 under accession number DSM 22635. The plasmid pALK2650 comprises the polynucleotide sequence encoding the full-length fungal serine protease enzyme.

The fungal serine protease enzyme is produced from a recombinant expression vector comprising the nucleic acid molecule encoding a fungal serine protease of the invention operably liked to regulatory sequences capable of directing the expression of the serine protease encoding gene in a suitable host. Suitable hosts include heterologous hosts, preferably microbial hosts of the genus *Trichoderma, Aspergillus, Fusarium, Humicola, Chrysosporium, Neurospora, Rhizopus, Penicillium* and *Mortiriella*.

Preferably, said enzyme is produced in *Trichoderma* or *Aspergillus*, most preferably in *T. reesei*.

The present invention relates also to an isolated nucleic acid molecule encoding a fungal serine protease enzyme applicable in modification, degradation or removal of proteinaceous materials at low or moderate temperature ranges selected from the group consisting of:
  (a) a nucleic acid molecule encoding a polypeptide having serine protease activity and comprising the amino acid sequence as depicted in SEQ ID NO:10 or a variant thereof having similar properties;
  (b) a nucleic acid molecule comprising the polynucleotide sequence as depicted in SEQ ID NO: 9;
  (c) a nucleic acid molecule comprising the coding sequence of the polynucleotide sequence SEQ ID NO:5 contained in DSM 22635;
  (d) a nucleic acid molecule the polynucleotide sequence of which differs from the polynucleotide sequence of a nucleic acid molecule of (b) or (c) due to the degeneracy of the genetic code.

The invention further relates to a recombinant expression vector comprising the nucleotide sequence of the invention operably linked to regulatory sequences capable of directing expression of said serine protease gene in a suitable host.

The invention relates also to a host cell comprising the recombinant expression vector as described above. Preferably, the host cell is a microbial host, such as a filamentous fungus. Preferred hosts are of a genus *Trichoderma, Aspergillus, Fusarium, Humicola, Chrysosporium, Neurospora,*

*Rhizopus*, *Penicillium* and *Mortiriella*. More preferably the host is *Trichoderma* or *Aspergillus*, most preferably a filamentous fungus *T. reesei*. The host may be homologous or heterologous to the nucleotide sequence of the invention.

The present invention relates to a process of producing a polypeptide of the invention having serine protease activity, said process comprising the steps of culturing the host cell of the invention and recovering the polypeptide. Also within the invention is a polypeptide having serine protease activity encoded by the nucleic acid sequence of the invention and which is obtainable by the process described above.

The invention relates to a process for obtaining an enzyme preparation comprising the steps of culturing a host cell of the invention and either recovering the polypeptide of the invention from the cells or separating the cells from the culture medium and obtaining the supernatant. Within the invention is also an enzyme preparation obtainable by the process described above.

The invention relates to an enzyme preparation, which comprises the serine protease enzyme of the invention.

The enzyme preparation of the invention may further comprise other enzymes selected from the group of protease, amylase, cellulase, lipase, xylanase, mannanase, cutinase, pectinase or oxidase with or without a mediator as well as suitable additives selected from the group of stabilizers, buffers, surfactants, bleaching agents, mediators, anti-corrosion agents, builders, antiredeposition agents, optical brighteners, dyes, pigments, caustics, abrasives and preservatives, etc.

The spent culture medium of the production host can be used as such, or the host cells may be removed, and/or it may be concentrated, filtrated or fractionated. It may also be dried. The enzyme preparation of the invention may be in the form of liquid, powder or granulate.

Also within the invention is the use of the serine protease enzyme or the enzyme preparation of the invention for detergents, for treating fibers, for treating wool, for treating hair, for treating leather, for treating food or feed, or for any applications involving modification, degradation or removal of proteinaceous material. Particularly, the enzyme or enzyme preparation is useful as a detergent additive in detergent liquids and detergent powders.

BRIEF DESCRIPTION OF DRAWINGS

FIG. 1 shows the nucleotide sequence (SEQ ID NO:5) of the *Trichoderma reesei* QM6a prb1 (Tr prb1) gene and the deduced amino acid sequence (SEQ ID NO:6). The putative signal peptide is in lower case letters and underlined. The putative pro sequence and the deduced amino acids of the pro sequence are in lower case letters. The mature nucleotide sequence is in capital letters. The intron sequences are in lower case, italic letters and marked by a dotted line below the nucleotide sequence. The stop codon is shown by an asterisk below the sequence. This figure shows the nucleotide sequence of Tr prb1 gene from the ATG start codon to the TAA stop codon (nucleotides 1 to 1371), the sequence region encoding the amino acid sequence from Met1 to Ala409 of the Tr Prb1 protein.

FIG. 2 shows the nucleotide sequence of the *Fusarium graminearum* ALKO1726 Fg prtS8A gene and the deduced amino acid sequence. The putative signal peptide, analyzed by SignalP V3.0 program is in lower case letters and underlined. The putative pro sequence and the deduced amino acids of the pro sequence are in lower case letters. The mature nucleotide sequence is in capital letters. The location of the putative intron sequence is in lower case, italic letters and marked by a dotted line below the nucleotide sequence. The stop codon is shown by an asterisk below the sequence. This figure shows the nucleotide sequence of Fg prt8A gene from the nucleotides 1 to 1292, the sequence region encoding the amino acid sequence from Met1 to Thr411 of the Fg_ALKO1726 protein.

ΔL*(deltaL*)=lightness value L* of enzyme treated fabric–lightness value L* of fabric treated without enzyme. A shows the performance at 30° C. with Liquid Base detergent at concentration of 5 g/l and pH appr. 7.5. B shows the performance at 30° C. with Liquid Base detergent at concentration of 3.3 g/l and pH appr. 7.4. C shows the performance at 30° C. with Liquid Base detergent at concentration of 1 g/l and pH appr. 7.3. D shows the performance at 20° C. with Liquid Base detergent at concentration of 3.3 g/l. E shows the performance at 10° C. with Liquid Base detergent at concentration of 3.3 g/l.

Figure 10A:
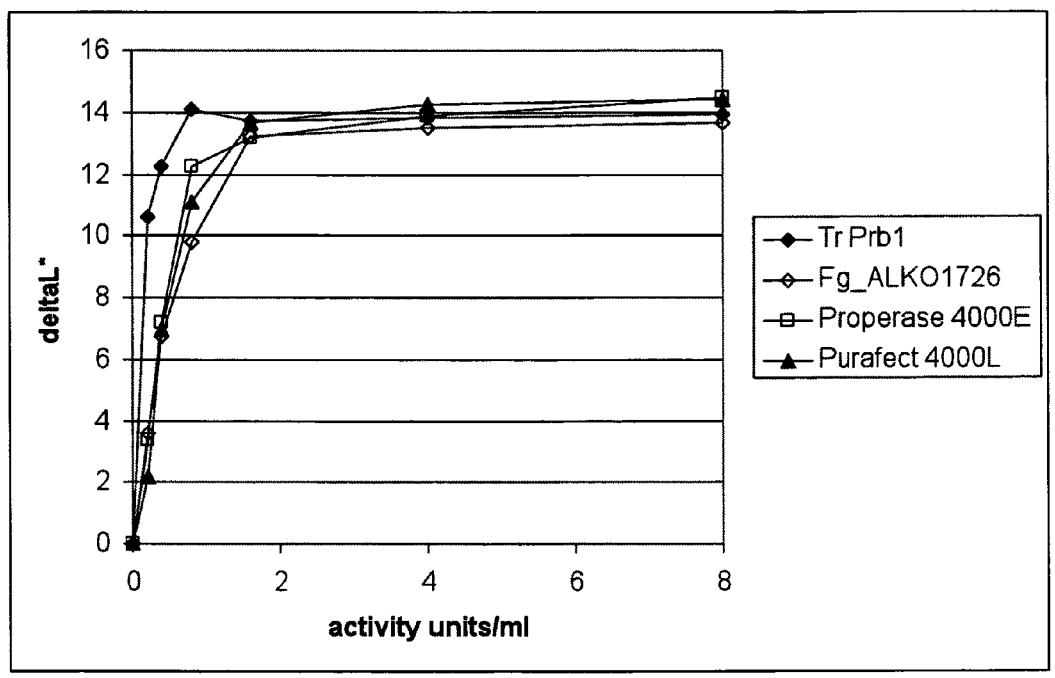
Figure 10B:
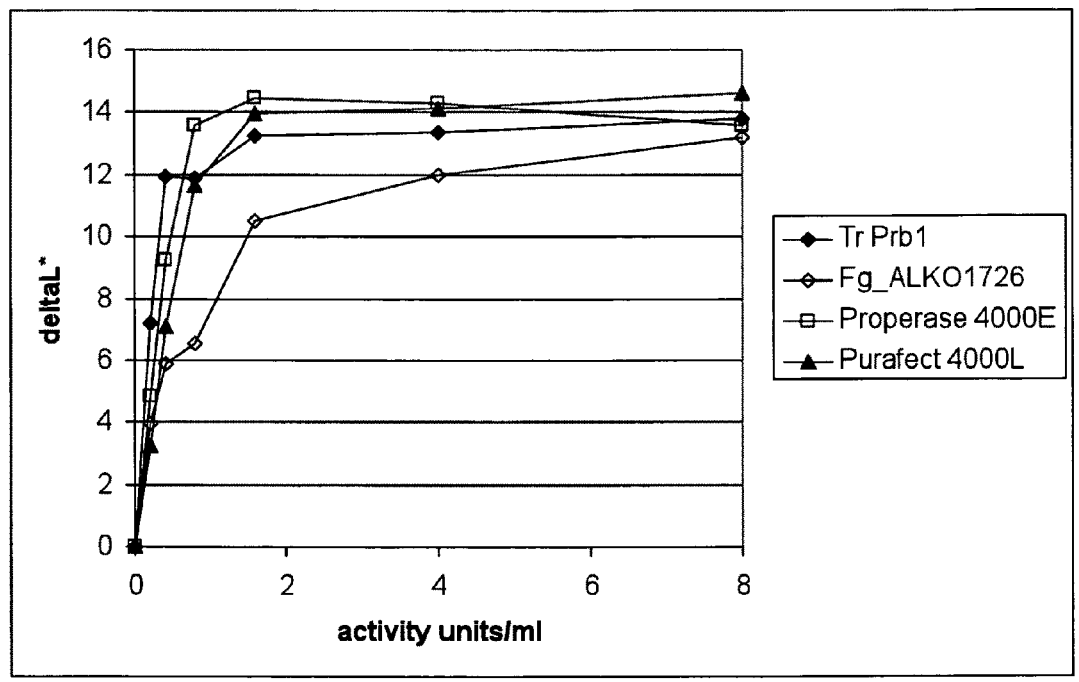
Figure 11A:
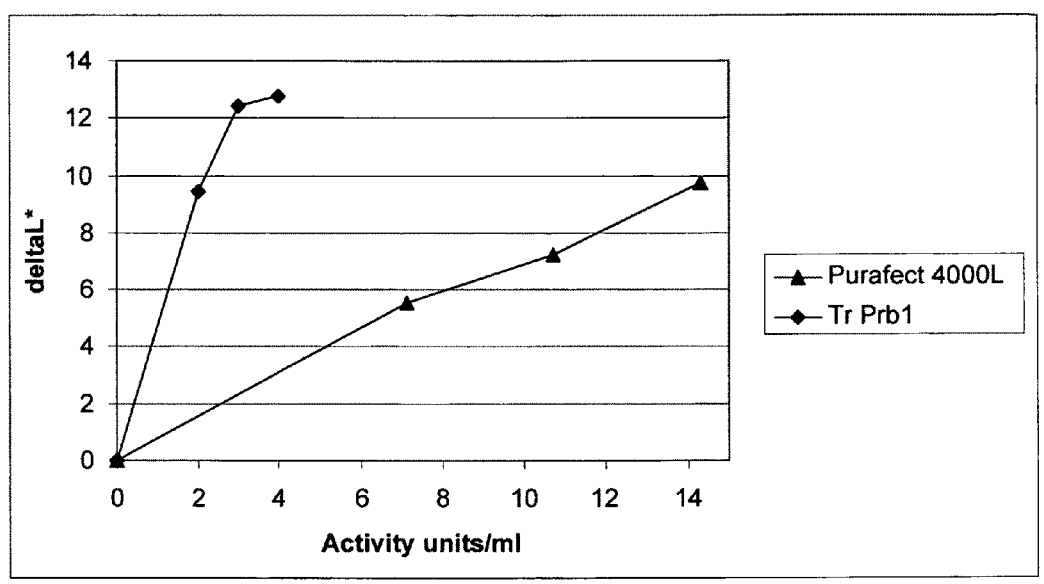
Figure 11B:
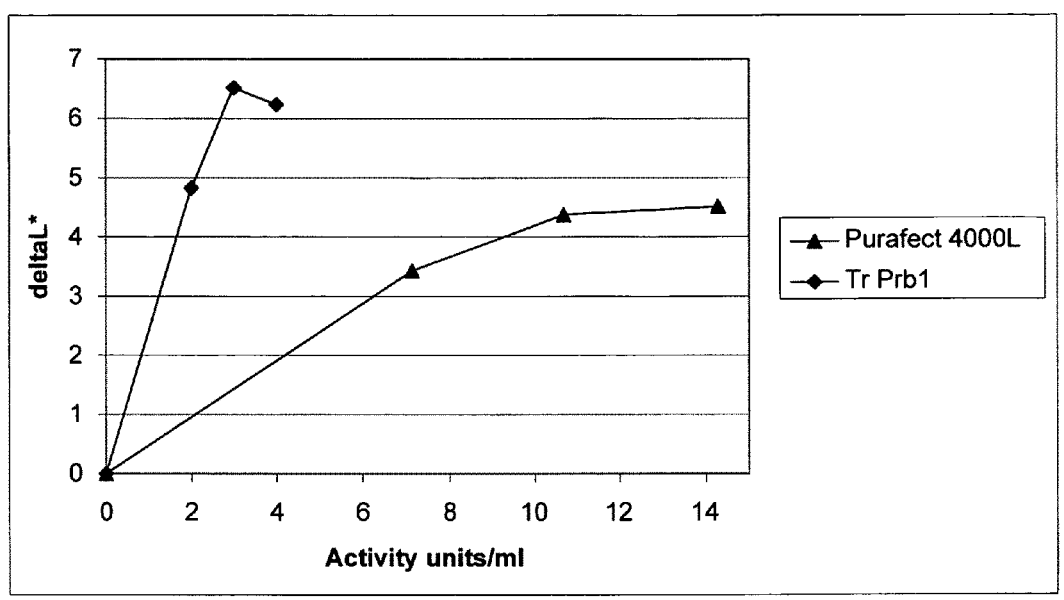
Figure 11G:
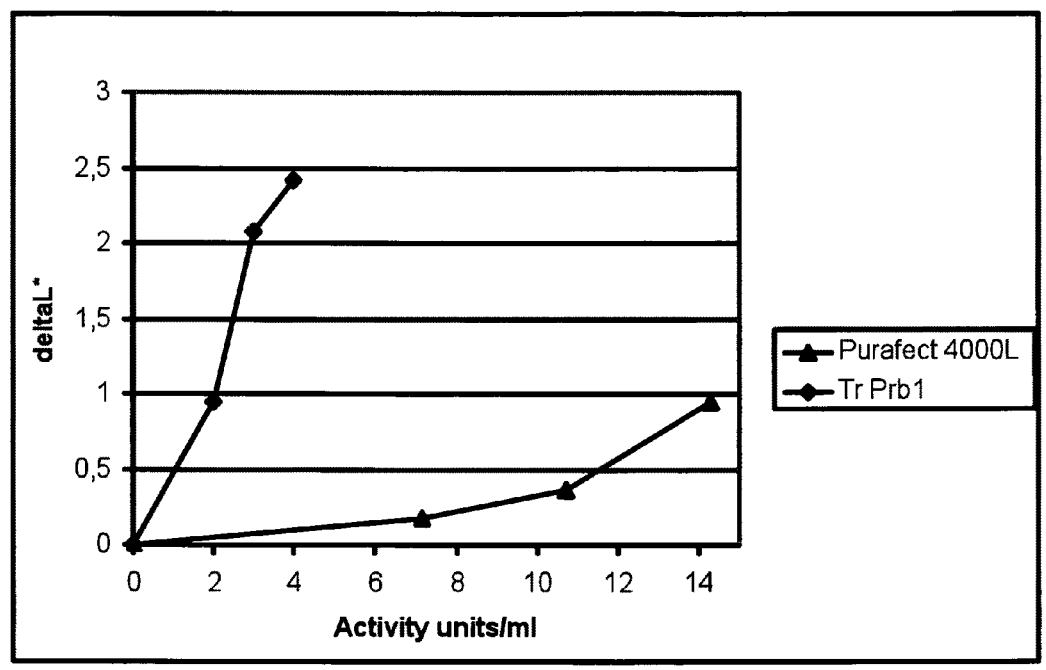
Figure 11H:
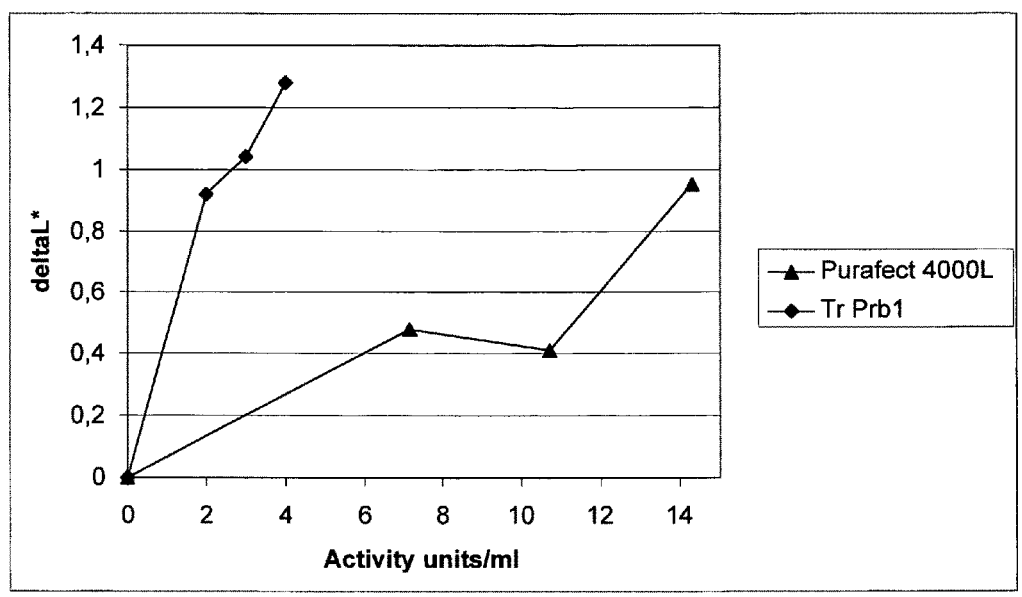
Figure 11I:
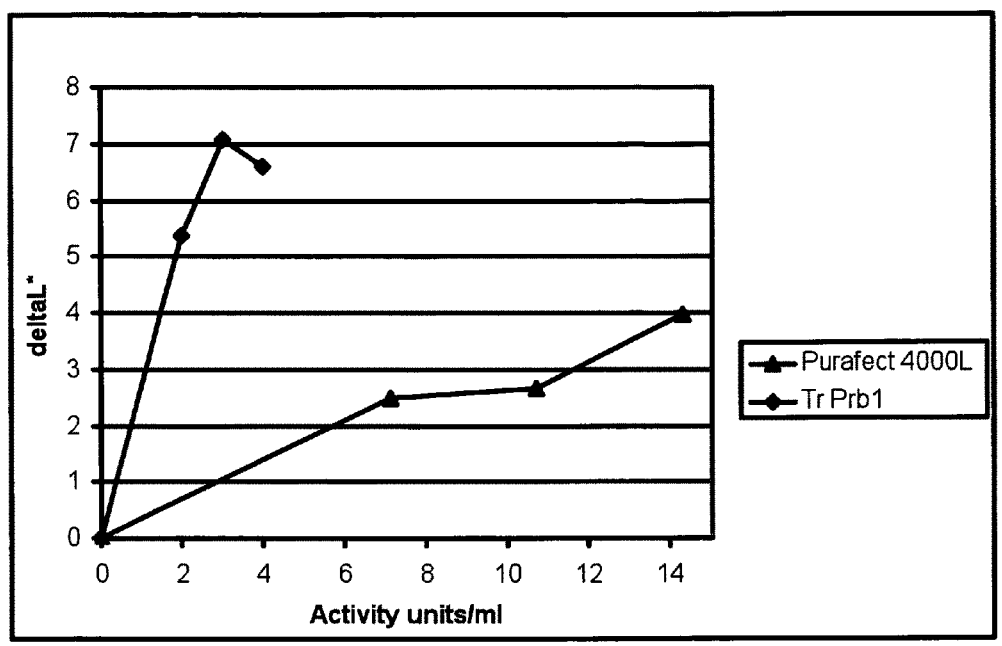

FIG. 10A-B describes the performance of recombinant proteins Tr Prb1 and Fg_ALKO1729 with blood/milk/ink stain (Art. 117, EMPA) in the presence of detergent powder (Art. 601, EMPA) at 40-50° C. and pH appr. 10. Commercial preparations Purafect® 4000L and Properase® 4000E were used for comparison. ΔL*(deltaL*)=lightness value L* of enzyme treated fabric–lightness value L* of fabric treated without enzyme A shows the performance at 40° C. B shows the performance at 50° C.

FIG. 11A-I describes the performance of recombinant protein Tr Prb1 with different stains (from EMPA and CFT) and Liquid Base detergent for colored fabrics in full-scale trials at 30° C. with 15 min washing time. Commercial preparations Purafect® 4000L was used for comparison. ΔL*(deltaL*) =lightness value L* of enzyme treated fabric–lightness value L* of fabric treated without enzyme. A shows performance on blood/milk/ink/PE+CO (Art. 117, EMPA). B shows performance on blood/milk/ink/PE+CO (Art. 116, EMPA). C shows performance on blood/milk/ink/PE+CO (CFT/PC-05-014). D shows performance on blood/milk/ink/CO (CFT/C-05-059b). E shows performance on cocoa (Art. 112, EMPA). F shows performance on chocolate/milk/pigment (CFT/C-03-030). G shows performance on groundnut oil/milk (CFT/C-10-186b). H shows performance on grass (CFT/CS-08-069). I shows performance on egg yolk/pigment (CFT/CS-38-010).

Figure 12A:
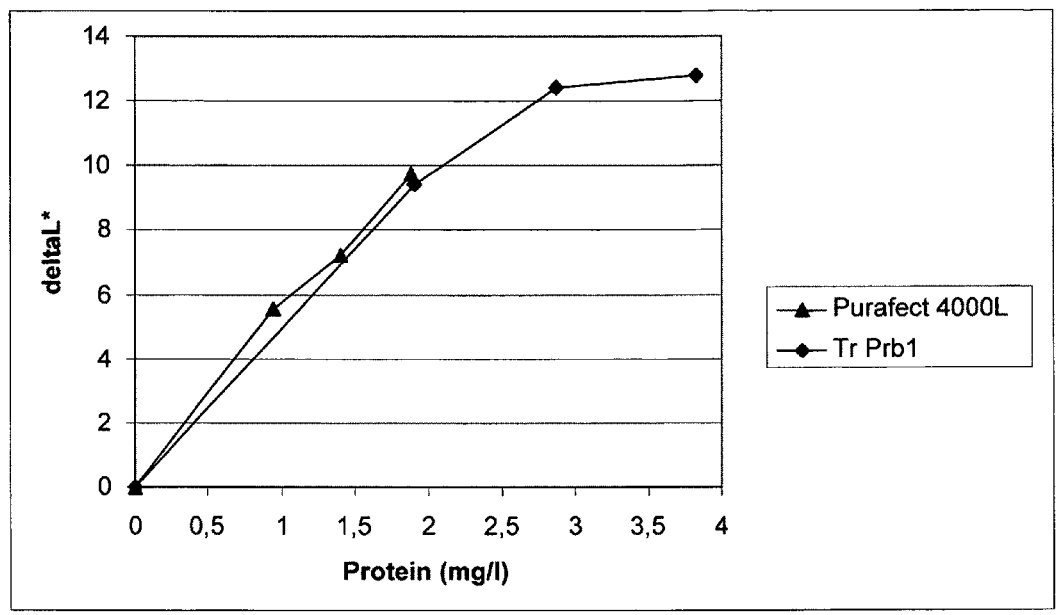
Figure 12B:
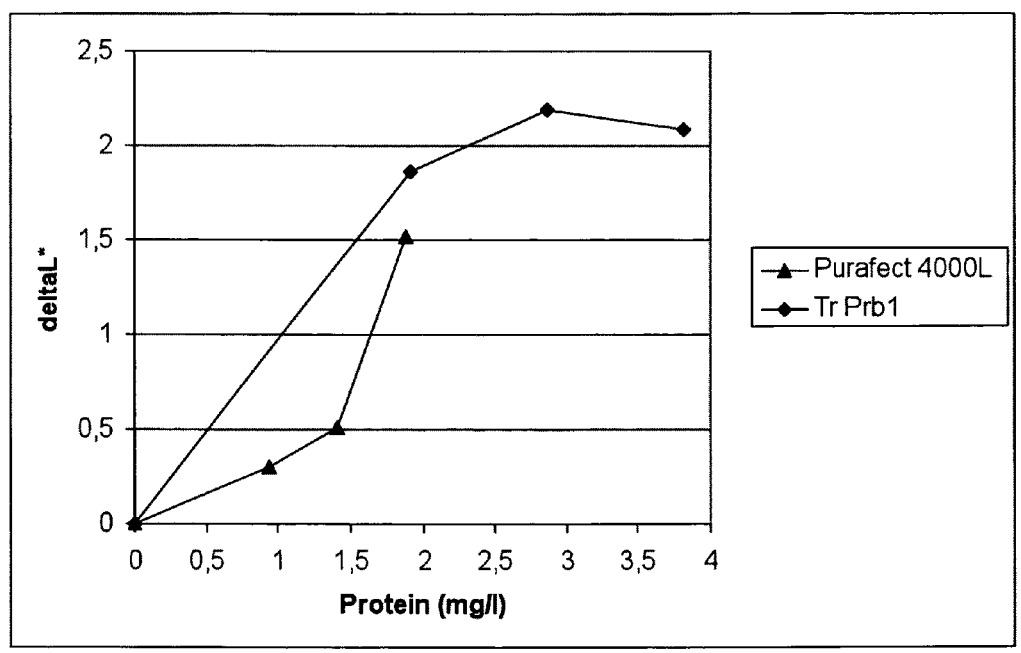

FIG. 12A-B describes the performance of recombinant protein Tr Prb1 with different stains and Liquid Base detergent for colored fabrics in full-scale trials at 30° C. with 15 min washing time, when enzyme dosage calculated was as amount of protein. Commercial preparations Purafect® 4000L was used for comparison. ΔL*(deltaL*)=lightness value L* of enzyme treated fabric–lightness value L* of fabric treated without enzyme. A shows performance on blood/milk/ink/PE+CO (Art. 117, EMPA). B shows performance on grass (CFT/CS-08-069).

SEQUENCE LISTING

SEQ ID NO: 1 Sequence of the 5'-PCR primer PRO213 used for cloning the *Trichoderma reesei* QM6a prb1 gene encoding Prb1 protease (protein ID 121495 according to Joint Genome Institute *T. reesei* genome, v. 2.0) and for fusing it to cbh1 promoter (exact fusion).

SEQ ID NO: 2 Sequence of the 3'-PCR primer PRO214 used for cloning the *Trichoderma reesei* QM6a prb1 gene encoding the Prb1 protease (protein ID 121495 according to Joint Genome Institute *T. reesei* genome, v. 2.0) and for fusing it to cbh1 terminator (via a linker).

SEQ ID NO: 3 Sequence of the 5'-PCR primer PRO245 used for cloning the *Fusarium graminearum* ALKO1726 protease and for fusing it to cbh1 promoter (exact fusion).

SEQ ID NO: 4 Sequence of the 3'-PCR primer PRO246 used for cloning the *Fusarium graminearum* ALKO1726 protease and for fusing it to cbh1 terminator (via a linker).

SEQ ID NO: 5 The nucleotide sequence of the full-length *Trichoderma reesei* QM6a protease gene prb1 (Tr prb1) encoding the Prb1 protease (ID 121495).

SEQ ID NO: 6 The deduced amino acid sequence of the full-length *Trichoderma reesei* QM6a protease Prb1 (Tr Prb1) including amino acids from Met1 to Ala409.

SEQ ID NO: 7 The nucleotide sequence encoding the amino acid sequence of the proenzyme form of *Trichoderma reesei* Prb1 protease.

SEQ ID NO: 8 The amino acid sequence of the proenzyme form of *Trichoderma reesei* Prb1 protease including amino acids Ala21 to Ala 409 of the full length protease.

SEQ ID NO: 9 The nucleotide sequence encoding the amino acid sequence of the mature form of *Trichoderma reesei* Prb1 protease.

SEQ ID NO: 10 The amino acid sequence of the mature form of *Trichoderma reesei* Prb1 protease including amino acids Ala121 to Ala409 of the full length enzyme.

SEQ ID NO: 11 The nucleotide sequence of the full-length *Fusarium graminearum* ALKO1726 protease gene Fg prtS8A.

SEQ ID NO: 12 The deduced amino acid sequence of the full-length *Fusarium graminearum* ALKO1726 protease (Fg_ALKO1726) including amino acids from Met1 to Thr411.

SEQ ID NO: 13 The nucleotide sequence encoding the amino acid sequence of the proenzyme form of *Fusarium graminearum* ALKO1726 protease.

SEQ ID NO: 14 The amino acid sequence of the proenzyme form of *Fusarium graminearum* ALKO1726 protease including amino acids Ala21 to Thr411 of the full length protease.

SEQ ID NO: 15 The nucleotide sequence encoding the amino acid sequence of the mature form of *Fusarium graminearum* ALKO1726 protease.

SEQ ID NO: 16 The amino acid sequence of the mature form of *Fusarium graminearum* ALKO1726 protease including amino acids Ala123 to Thr411 of the full length enzyme.

DEPOSITS

*Fusarium graminearum* ALKO1726 was deposited at the Centraalbureau Voor Schimmelcultures at Uppsalalaan 8, 3508 AD, Utrecht, the Netherlands on 3 Jun. 2009 and assigned accession number CBS 124697.

The *E. coli* strain RF8052 including the plasmid pALK2650 was deposited at the Deutsche Sammlung von Mikroorganismen und Zellkulturen GmbH (DSMZ), Inhoffenstrasse 7 B, D-38124 Braunschweig, Germany on June 3 and assigned accession number DSM 22635.

The *E. coli* strain RF8098 including the plasmid pALK2707 was deposited at the Deutsche Sammlung von Mikroorganismen und Zellkulturen GmbH (DSMZ), Inhoffenstrasse 7 B, D-38124 Braunschweig, Germany on 3 Jun. 2009 and assigned accession number DSM 22636.

DETAILED DESCRIPTION

The present invention provides a serine protease of fungal origin, which protease shows broad substrate specificity, is active at high pH ranges and has a broad temperature optimum, i.e. good performance both at low and moderate temperatures. The enzyme is ideal for detergent applications, withstanding typical detergent compositions and being effective at low enzyme levels in detergent solutions. Particularly, the serine protease is active at low temperatures, even at or below 10° C., the preferred range being from 10° C. to 60° C.

Thus, the present invention provides an alternative serine protease for use in detergent and other industrial applications, in which the performance at low or moderate temperature ranges is desirable. The fungal serine protease can be produced in high-yielding fungal hosts and its down-stream processing, e.g. separation of fermentation broth and mycelia is easy to perform.

By "serine protease" or "serine endopeptidase" or "serine endoproteinase" is in connection to this invention meant an enzyme classified as EC 3.4.21 by the Nomenclature of the International Union of Biochemistry and Molecular Biology. Serine proteases are found in both single-cell and complex organisms. Based on their structural similarities, serine proteases have been grouped into at least six clans (SA, SB, SC, SE, SF and SG; S denoting serine protease), which have been further subgrouped into families and subfamilies with similar amino acid sequences and three-dimensional structures (see, for example the Serine protease home page at biochem.wustl.edu/~protease/, Department of Biochemistry and Molecular Biophysics, Washington University of Medicine, St. Louis, Mo., USA). These protein hydrolyzing or degrading enzymes are characterized by the presence of a nucleophilic serine group in their active site, and the proteases of the major clans SA and SB are also distinguished by having essential aspartate and histidine residues, which along with the serine, form a catalytic triad. The enzymes target different regions of the polypeptide chain, based upon the amino acid residues surrounding the site of cleavage.

The serine protease of the present invention belongs to clan SB, family 8 consisting of subtilisin-like serine proteases" or "subtilases". This class of serine proteases, represented by various *Bacillus* species, like *B. amyloliquifaciens, B. licheniformis* and *B. subtilis* (Rao et al., 1998), is specific for aromatic or hydrophobic residues, such as tyrosine, phenylalanine and leucine.

By the term "serine protease activity" as used in the invention is meant hydrolytic activity on protein containing substrates, e.g. casein, haemoglobin, keratin and bovine serum albumin (BSA). The methods for analysing proteolytic activity are well-known in the literature and are referred e.g. in Gupta et al. (2002).

Proteases can be classified using group specific inhibitors. The diverse group of "serine protease inhibitors" includes synthetic chemical inhibitors and natural proteinaceous inhibitors. One group of natural inhibitors are serpins (abbreviated from serine protease inhibitors), such as antithrombin and alpha 1-antitrypsin. Artificial synthetic inhibitors include 3,4-dichloroisocoumarin (3,4-DCI), diisopropylfluorophosphate (DFP), phenylmethylsulfonyl fluoride (PMSF) and tosyl-L-lysine chloromethyl ketone (TLCK). Some of the serine proteases are inhibited by thiol reagents such as p-chloromercuribenzoate (PCMB) due to the presence of a cysteine residue near the active site. Thus, the serine protease activity can be determined in an assay based on cleavage of a specific substrate or in an assay using any protein containing substrate with or without a specific inhibitor of serine proteases under suitable conditions.

The serine proteases are synthesized as inactive "zymogenic precursors" or "zymogens" in the form of a preproenzyme, which are activated by removal of the signal sequence (secretion signal peptide or prepeptide) and the prosequence (propeptide) to yield an active mature form of the enzyme (Chen and Inouye, 2008). This activation process involves action of proteases and may result from limited self-digestive or autocatalytic processing of the serine protease. The prosequence may be cleaved for example during posttranslational phases of the production or in the spent culture medium or during the storage of the culture medium or enzyme preparation. Activation of the proenzyme may also be achieved by adding a proteolytic enzyme capable of converting the inactive proenzyme into active mature enzyme into the culture medium where the host organism is cultivated or adding the proteolytic enzyme to the culture supernatant after cultivation process. The shortening of the enzyme can also be achieved e.g. by truncating the gene encoding the polypeptide prior to transforming it to the production host.

The term "mature" means the form of enzyme which after removal of the signal sequence and propeptide comprises the essential amino acids for enzymatic or catalytic activity. In filamentous fungi it is the native form secreted into the culture medium.

Microorganism strains capable of producing protease activity can be screened on different substrates. Chosen strains can be cultivated on a suitable medium to produce a sufficient amount of an interesting serine protease for isolation or purification and further characterization of its properties. Alternatively, genes encoding serine proteases in various organisms can be isolated and the amino acid sequence encoded by the genes can be compared with the amino acid sequence of the serine proteases isolated and characterized in the Examples here.

The serine protease enzyme of the invention may derive from a fungus, including filamentous fungi and yeasts, for example from a *Trichoderma* genus. Fungal alkaline proteases are advantageous to the bacterial proteases due to the ease of down-stream processing to produce a microbe-free enzyme or enzyme composition. Mycelium can be easily removed through filtration techniques prior to the purification of the enzyme.

The native or recombinant serine protease can be purified by using conventional methods of enzyme chemistry, such as salt preparation, ultrafiltration, ion exchange chromatography, affinity chromatography, gel filtration and hydrophobic interaction chromatography. Purification can be monitored by protein determination, enzyme activity assays and by SDS polyacrylamide gel electrophoresis. The enzyme activity and stability of the purified enzyme at various temperature and pH values as well as the molecular mass and the isoelectric point can be determined.

The purification of two recombinant serine proteases has been demonstrated in Example 3. The filtrated and desalted culture supernatants of *T. reesei* QM6a and *F. graminearum* ALKO1726 were applied to a Q Sepharose FF column. The flow-through fractions were applied to a Superdex 75 10/300 GL column. Purification was followed by activity assays on casein as described in Example 2c and 8. Naturally, it is possible to separate the enzyme of the present invention by using other known purification methods instead, or in addition to the methods described herein. The recombinant serine proteases were used for characterization of pH and temperature profiles as described in Example 3.

Determination of the pH optimum can be carried out in a suitable buffer at different pH values by following the activity on a protein substrate. Serine proteases are generally active at neutral or alkaline pH, with an optimum between pH 7 and 11, and have broad substrate specificity. The "alkaline serine proteases" mean enzymes that are active and stable at pH 9 to pH 11 or even at pH 10 to 12.5 (Shimogaki et al., 1991) and have isoelectric point around pH 9.

The temperature optimum of the serine protease can be determined in a suitable buffer at different temperatures by using casein as a substrate as described in Examples 2c, 3 or 8 or by using other substrates and buffer systems described in the literature (Gupta et al., 2002). The temperature optima of the natural serine proteases are around 60° C. (Rao et al., 1998).

pI can be determined by isoelectric focusing on an immobilized pH gradient gel composed of polyacrylamide, starch or agarose or by estimating the pI from the amino acid sequence, for example by using the pI/MW tool at ExPASy server expasy.org/tools/pi_tool.html; Gasteiger et al., 2003).

The molecular mass of the purified serine protease can be determined by mass spectrometry or on SDS-PAGE according to Laemmli (1970). The molecular mass can also be predicted from the amino acid sequence of the enzyme. The mature serine protease or mature serine protease enzyme typically has a molecular mass between 20 to 35 kDa, typically around 25 to 30 kDa (Rao et al., 1998). The N-terminus of the purified protease as well as internal peptides can be sequenced according to Edman degradation chemistry (Edman and Begg, 1967) or by other methods described in the literature.

Protease activity is generally based on degradation of soluble substrates. In detergent application proteases have to work on substances which are at least partly insoluble. Thus an important parameter for a detergent protease is the ability to adsorb to and hydrolyze these insoluble fragments.

Another important parameter for selection of detergent proteases is its isoelectric point or pI value. The detergent proteases perform best when the pH value of the detergent solution in which it works is approximately the same as the pI value for the enzyme.

In the present invention "a good performance in presence of detergent" means that the enzyme or preparation comprising said enzyme, in this case the fungal serine protease of the invention, functions at lower temperature ranges than many commercial subtilisins presently for sale. In other words, "good performance" means that the enzyme is capable of modifying, degrading or removing proteinaceous stains or material at low to moderate temperature ranges, but has especially good performance at lower temperature ranges (10-30° C.) than the present commercial products, for example the commercial enzyme product Purafect® 4000L (Genencor Inc., USA) or Savinase® (Novozymes A/S, DK). For example, by modifying pH, selecting detergents with suitable properties, including enzyme protecting agents and by controlling washing conditions the activity of the serine protease of the invention may be maintained at temperatures as low as 10° C.

The expression "detergent" is used to mean substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical "proteinaceous material" includes blood, milk, ink, egg, grass and sauces. For testing purposes mixtures of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

The term "low temperature" in context of the present application means temperature ranges from 10° C. to 30° C., which according to the Experiments are not optimal for the performance of many of the presently available enzyme preparations, particularly the detergent enzyme preparations. By the term "moderate temperature" is meant a temperature range from 30° C. to 60° C.

The term "applicable at low or moderate temperature ranges" includes industrial applications in which it is desirable that the enzyme functions effectively at low or moderate temperature ranges (10° C. to 60° C.). Such applications include their use in food, feed and leather industry, pharmaceuticals, diagnostics, waste management and silver recovery. As meant herein, these applications exclude the use of the serine protease enzyme of the invention as a biocontrol agent in biological control of plant pathogenic fungi and nematodes.

According to a preferred embodiment of the invention the fungal serine protease enzyme is a polypeptide applicable or useful in modification, degradation or removal of proteinaceous materials in applications, in which performance of the enzyme at low or moderate temperatures is desirable. Said fungal serine protease has serine protease activity and comprises the mature enzyme of Tr Prb1 having the amino acid sequence SEQ ID NO:10 and is capable of modifying, degrading or removing protein containing material at low or moderate temperatures. The mature enzyme lacks the signal sequence or prepeptide and the prosequence or propeptide. The mature serine protease of the invention includes amino acids Ala121 to Ala409 of the full length protease characterized in SEQ ID NO:6. Thus, within the scope of the invention is also the full-length Tr Prb1 enzyme having SEQ ID NO:6 including the signal sequence (prepeptide) and propeptide and the mature enzyme as well as the proenzyme form lacking the signal sequence (prepeptide) but including the propeptide and the mature enzyme, thus having SEQ ID NO:8.

Natural variants of the amino acid sequence SEQ ID No:10 are also included in the context of the invention. These variants include minor changes in the amino acid sequence, for example as a result to production of the protein in a heterologous host organism, which may cause changes in one or more positions in the amino acid sequence due to deletion, substitution, insertion, addition or combination thereof. These variations, however, do not alter the biological function of the molecules. Thus, the variants are similar in properties, i.e. in characteristics and activity to the serine protease having the amino acid sequence SEQ ID NO:10.

By the term "identity" is here meant the identity between two amino acid sequences compared to each other within the corresponding sequence region having approximately the same amount of amino acids. For example, the identity of a full-length or a mature sequence of the two amino acid sequences may be compared. The identity of the sequences may be measured by using ClustalW alignment (e.g. in www.ebi.ac.uk/Tools/Clustalw) using the matrix: BLOSUM, Gap open: 10, Gap extension: 0.5. The identity of the two sequences is high, preferably at least 94%, preferably at least 95%, more preferably 96%, more preferably 97%, even more preferably 98%, and most preferably 99%.

Preferably, the fungal serine protease of the invention is applicable as a detergent additive.

The serine protease of the present invention is named Tr Prb1, an isolated serine protease originating from the genus *Trichoderma*, more preferably from *T. reesei*, most preferably *T. reesei* QM6a strain (ATCC 13631, CBS 383.78, IMI 192654, IMI 45548 and T.V. B117) and is a member of clan SB, family 8 of serine endoproteinases.

A preferred embodiment of the invention is a fungal serine protease which has serine protease activity and comprises the mature enzyme of Tr Prb1 having the amino acid sequence SEQ ID NO:10.

The present invention relates to a fungal serine protease enzyme, the mature form of which has a molecular mass or molecular weight between 20 and 35 kDa, preferably between 25 and 33 kDa, more preferably between 28 and 30 kDa. The most preferred MW is the predicted molecular mass of Tr Prb1 being 29 kDa for the mature polypeptide obtained by using the Compute pI/MW tool at ExPASy server (Gasteiger et al., 2003).

The enzyme of the invention is effective in degrading proteinaceous material at a broad temperature range. The optimal temperature of the enzyme is from 30° C. to 70° C. (about 20% of the maximum activity), preferably from 40° C. to 60° C. (at least about 40% of the maximum activity), and more preferably between 50° C. and 60° C. (at least 70% of the maximum activity), most preferably at 50° C. (the maximum activity of Tr Prb1) when measured at pH 9 using 15 min reaction time and casein as a substrate as described in Example 3.

According to one preferred embodiment of the invention the fungal serine protease enzyme has pH optimum at a pH range from at least pH 6 to pH 11, showing over 20% of the maximum activity at a pH range from pH 6 to pH 10 at 50° C. using 15 min reaction time and casein as a substrate as described in Example 2c and Examples 3 or 8. In particular, the pH optimum is between pH 6 and pH 10 (at least about 90% of the maximum activity).

The fungal serine protease of the invention has good performance in the presence of detergent, i.e. is capable of modifying, degrading or removing proteinaceous stains or material in the presence of detergent at low (10° C. to 30° C.) to moderate temperature (30° C. to 60° C.) ranges, specifically at lower temperature ranges than the present commercial products, for example the commercial enzyme product Purafect® 4000L and Properase® 4000E (Genencor Inc., USA), and Savinase® (Novozyme A/S, DK). Depending on the washing conditions and auxiliary ingredients and additives in detergents the enzyme of the invention functions between 10° C. and 60° C., preferably at or below 50° C. The Tr Prb1 enzyme functions also in temperatures at or below 45° C., at or below 40° C., at or below 35° C., at or below 30° C., at or below 25° C., at or below 20° C., at or below 15° C., or at or below 10° C.

In the presence of a detergent, the fungal serine protease of the invention functions as defined above between 10° C. and 60° C. and particularly, said fungal serine protease Tr Prb1 has a good performance in detergent at ≦30° C. In Examples 5 to 7, comparative experiments are described, and from FIGS. 7 to 12 it is evident that the performance of the fungal serine protease Tr Prb1 in varying conditions and exposed to varying treatments, on multitude of different stains on different textile material, measured as deltaL*, is by far better than the performance of the commercial products, Savinase® Ultra 16L (Novozymes A/S, DK), Properase® 4000E and Purafect® 4000L (Genencor Inc, USA). According to the manufacturer Properase® is an alkaline protease suitable for low-temperature washing conditions.

From said experimental results it can be concluded that the fungal serine protease of the invention is capable of satisfying the greatly varying demands of detergent customers and detergent industry and industry providing washing machinery and is well suited to the requirements of future regulations and customer habits.

The serine protease enzyme of the invention has pI, which as predicted from the deduced amino acid sequence is between pI 8.7 and pI 9.4, preferably between pI 8.8 and pI 9.3. The predicted pI of Tr Prb1 enzyme of the invention is pI 8.9.

According to one preferred embodiment the fungal serine protease enzyme of the invention is encoded by an isolated nucleic acid molecule, which encodes a polypeptide comprising the amino acid sequence characterized in SEQ ID NO:10 or a variant thereof having similar properties.

Isolation of cDNA or a genomic gene encoding the serine protease of the invention may be performed using PCR and primers designed based on the known nucleotide or amino acid sequences of homologous serine proteases. Also, oligonucleotides synthesized on the amino acid sequence of N-terminal or tryptic peptides of the purified enzyme or a PCR product obtained by using the above oligonucleotides can be used as probes in isolation of cDNA or a genomic gene encoding the serine protease of the invention. The serine protease clones may also be screened based on activity on plates containing a specific substrate for the enzyme or by using antibodies specific for a serine protease.

In the present invention the Tr prb1 gene was isolated using PCR and primers designed according to the sequence of the prb1 gene (gene ID 121495), published by DOE Joint Genome Institute (T. reesei QM6a genome sequence v2.0, genome.jgi-psf.org/cgi-bin/dispGeneModel?db=Trire2&id121495) as described in Example 1b. Standard molecular biology methods can be used in isolation of cDNA or a genomic DNA of the host organism, e.g. the methods described in the molecular biology handbooks, such as Sambrook and Russell, 2001.

In case the polynucleotide sequence is isolated using a DNA probe prepared by PCR, the hybridization with a DNA probe consisting of more than 100-200 nucleotides, is usually performed at "high stringency" conditions, i.e. hybridization at a temperature, which is 20-25° C. below the calculated melting temperature (Tm) of a perfect hybrid, the Tm calculated according to Bolton and McCarthy (1962). Usually prehybridization and hybridization are performed at least at 65° C. in 6×SSC (or 6×SSPE), 5×Denhardt's reagent, 0.5% (w/v) SDS, 100 µg/ml denatured, fragmented salmon sperm DNA. Addition of 50% formamide lowers the prehybridization and hybridization temperatures to 42° C. Washes are performed in low salt concentration, e.g. in 2×SSC-0.5% SDS (w/v) for 15 minutes at room temperature (RT), followed in 2×SSC-0.1% SDS (w/v) at RT, and finally in 0.1×SSC-0.1% SDS (w/v) at least at 65° C.

Thus, within the scope of the invention is a polypeptide sequence, which is encoded by a nucleic acid molecule encoding the amino acid sequence of the full-length serine protease of the invention including the prepeptide (signal sequence) and the propeptide in addition to the mature form of the enzyme, and which amino acid sequence is characterized in SEQ ID NO:6.

Also, within the scope of the invention is a polypeptide sequence, which is encoded by a nucleic acid molecule encoding the propeptide of serine protease enzyme of the invention including the propeptide in addition to the mature form of the enzyme, and which amino acid sequence is characterized in SEQ ID NO: 8.

One preferred embodiment of the invention is a fungal serine protease enzyme encoded by an isolated nucleic acid molecule, which comprises the nucleotide sequence encoding the mature form of the Tr Prb1 serine protease having SEQ ID NO: 9.

Thus, the Tr Prb1 polypeptide of the invention is encoded by the nucleic acid molecule having the nucleotide sequence SEQ ID NO:5 comprising the "coding sequence" for the enzyme. The expression "coding sequence" means the nucleotide sequence which initiates from the translation start codon (ATG) and stops at the translation stop codon (TAA, TAG or TGA) and may contain intron sequences. The translated full-length polypeptide starts usually with methionine. The fungal serine protease enzyme of the invention may be encoded also by a nucleic acid molecule comprising the nucleotide sequence SEQ ID NO: 7, which encodes the Tr Prb1 proenzyme form.

According to a preferred embodiment of the invention the fungal serine protease enzyme is encoded by an isolated polynucleotide sequence included in plasmid pALK2650 comprising the nucleotide sequence SEQ ID NO:5 in *E. coli* RF8052, deposited at the Deutsche Sammlung von Mikroorganismen and Zellkulturen (DSMZ) under accession number DSM 22635.

One embodiment of the invention is the serine protease enzyme produced from a recombinant expression vector comprising the nucleic acid molecule, which encodes the fungal serine protease enzyme as characterized above operably linked to regulatory sequences capable of directing the expression of said serine protease encoding gene in a suitable host. Construction of said recombinant expression vector and use of said vector is described in more detail in Example 2.

Suitable hosts for production of the fungal serine protease enzyme are homologous or heterologous hosts, such as the microbial hosts including bacteria, yeasts and fungi. Filamentous fungi, such as *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable hosts include species such as *T. reesei, A. niger, A. oryzae, A. sojae, A. awamori* or *A. japonicus* type of strains, *F. venenatum* or *F. oxysporum, H. insolens* or *H. lanuginosa, N. crassa* and *C. lucknowense*, some of which are listed as enzyme production host organisms in e.g. AMFEP 2007 list of commercial enzymes (www.amfep.org/list.html). More preferably, the enzyme is produced in a filamentous fungal host of the genus *Trichoderma* or *Aspergillus*, such as *T. reesei* or *A. niger, A. oryzae* or *A. awamori*. According the most preferred embodiment of the invention the fungal serine protease enzyme is produced in *T. reesei*.

The present invention relates also to an isolated nucleic acid molecule encoding the fungal serine protease enzyme applicable in modification, degradation or removal of proteinaceous materials at low or moderate temperature ranges selected from the group consisting of:
(a) a nucleic acid molecule encoding a polypeptide having serine protease activity and comprising the amino acid sequence as depicted in SEQ ID NO:10 or a variant thereof having similar properties;
(b) a nucleic acid molecule comprising the polynucleotide sequence as depicted in SEQ ID NO: 9;
(c) a nucleic acid molecule comprising the coding sequence of the polynucleotide sequence SEQ ID NO:5 contained in DSM 22635;
(d) a nucleic acid molecule the polynucleotide sequence of which differs from the polynucleotide sequence of a nucleic acid molecule of (b) to (c) due to the degeneracy of the genetic code.

The nucleic acid molecule of the invention may be RNA or DNA, wherein the DNA may constitute of the genomic DNA or cDNA.

Standard molecular biology methods can be used in isolation and enzyme treatments of the polynucleotide sequence encoding the fungal serine protease of the invention, including isolation of genomic and plasmid DNA, digestion of DNA to produce DNA fragments, sequencing, *E. coli* transformations etc. The basic methods are described in the standard molecular biology handbooks, e.g. Sambrook and Russell, 2001.

Isolation of the full length Tr prb1 gene encoding the Tr Prb1 polypeptide is described in Example 1. Briefly, the gene was isolated using PCR and primers designed according to the sequence of the prb1 gene (gene ID 121495), published by DOE Joint Genome Institute (*T. reesei* QM6a genome sequence v2.0, genome.jai-psf.org/cgi-bin/dispGeneModel?db=Trire2&id121495). The full-length Tr prb1 gene was included in the plasmid pALK2650 deposited in *E. coli* to the DSMZ culture collection under accession number DSM 22635. The deduced amino acid sequence of the serine protease was analyzed from the DNA sequence.

The nucleotide sequence of the full-length *T. reesei* serine protease Tr prb1 (SEQ ID NO: 5) and the deduced sequence (SEQ ID NO: 6) are presented in FIG. 1A-B. The length of the gene is 1371 bp (including the stop codon). Two putative introns were found having the length of 68 and 73 bps, respectively. The deduced protein sequence consists of 409 amino acids including a predicted signal sequence of 20 amino acids (SignalP V3.0; Nielsen et al., 1997 and Nielsen and Krogh, 1998) and a propeptide from Ala21 to Ala121. The predicted molecular mass was 29 kDa for the mature polypeptide and the predicted pI was 8.94. These predictions were made using the Compute pI/MW tool at ExPASy server (Gasteiger et al., 2003). The deduced amino acid sequence contained two possible N-glycosylation sites (Asn252 and Asn396), but according to CBS Server NetNGlyc V1.0 only one site, Asn252 is probable. The homologies to the published protease sequences were searched using the BLASTP program, version 2.2.21 at NCBI (National Center for Biotechnology Information) (Altschul et al., 1990). The identity values of the mature Tr Prb1 sequence to the corresponding regions of homologous sequences were obtained by using ClustalW alignment (Matrix: BLOSUM, Gap open: 10, Gap extension: 0.5 (e.g. in www.ebi.ac.uk/Tools/Clustalw).

The serine protease Tr Prb1 of the present invention showed highest homology (92-93% identity) to an alkaline protease from *T. hamatum* (AAP15044; Steyaert et al., 2004), serine endopeptidase from *Hypocrea lixii* (teleomorph *T. harzianum*; CAL25580; Suarez et al. 2007), alkaline proteinase from *T. atroviride* (ALP_TRIAT; Geremia et al., 1993) and extracellular serine protease Tvsp1 from *Hypocrea virens* (AAO63588; Pozo et al., 2004). The identity of Tr Prb1 mature amino acid sequence to the corresponding region of ALP protease (EMBL accession no. M87516; Geremia et al. 1993; disclosed as SEQ ID NO:313 in U.S. 60/818,910 (Catalyst Bioscience Inc.)) was 92%.

Thus, within the scope of the invention is an isolated polynucleotide sequence or isolated nucleic acid molecule, which encodes a fungal serine protease enzyme or polypeptide comprising the amino acid sequence of the mature form of the Tr Prb1 enzyme characterized in SEQ ID NO: 10, i.e. amino acids Ala121 to Ala409 of the full length serine protease of SEQ ID NO:6.

Also, isolated polynucleotide sequences encoding natural variants of the amino acid sequence SEQ ID NO: 10 are included. These variants include minor changes in the amino acid sequence, e.g. changes in one or more positions in the amino acid sequence due to deletion, substitution, insertion, addition or combination thereof. These variations, however, do not alter the biological function of the molecules. Thus, the variants have the properties, i.e. characteristics and activity of the serine protease having the amino acid sequence SEQ ID NO:10. Identity between two amino acid sequences may be compared with each other within the corresponding sequence region having approximately the same amount of amino acids. For example, the identity of a full-length or a mature sequence of the two amino acid sequences may be compared. The identity of the sequences may be measured by using ClustalW alignment (e.g. in www.ebi.ac.uk/Tools/Clustalw)

using the matrix: BLOSUM, Gap open:10, Gap extension: 0.5. The identity of the two sequences is high, preferably at least 94%, preferably at least 95%, more preferably 96%, more preferably 97%, even more preferably 98%, and most preferably 99%.

The isolated polynucleotide sequence or isolated nucleic acid molecule comprises preferably the polynucleotide sequence as defined in SEQ ID NO:9, i.e. a polynucleotide sequence encoding the amino acid sequence of the mature Tr Prb1 of SEQ ID NO:10.

The isolated nucleic acid molecule of the invention may be a molecule comprising the coding sequence of the polynucleotide sequence SEQ ID NO: 5 contained in DSM 22635 carrying the nucleotide sequence of the full length Tr prb1 gene.

The nucleic acid molecule of the invention may also be an analogue of the nucleotide sequence characterized in above. The "degeneracy" means analogues of the nucleotide sequence, which differ in one or more nucleotides or codons, but which encode the recombinant protease of the invention.

Thus, within the scope of the invention is an isolated nucleic acid molecule comprising a nucleotide sequence as depicted in SEQ ID NO:5, SEQ ID NO:7 or SEQ ID NO:9 and analogues thereof.

According to one preferred embodiment of the invention, the isolated nucleic acid molecule encodes a fungal serine protease for use as a detergent additive.

The present invention relates also to a recombinant expression vector or recombinant expression construct, which can be used to propagate or express the nucleic acid sequence encoding the chosen serine protease in a suitable prokaryotic or eukaryotic host. The recombinant expression vector comprises DNA or nucleic acid sequences which facilitate or direct expression and secretion of the serine protease encoding sequence in a suitable host, such as promoters, enhancers, terminators (including transcription and translation termination signals) and signal sequences operably linked the polynucleotide sequence encoding said serine protease. The expression vector may further comprise marker genes for selection of the transformant strains or the selection marker may be introduced to the host in another vector construct by co-transformation. Said regulatory sequences may be homologous or heterologous to the production organism or they may originate from the organism, from which the gene encoding the serine protease is isolated.

Examples of promoters for expressing the serine protease of the invention in filamentous fungal hosts are the promoters of *A. oryzae* TAKA amylase, alkaline protease ALP and triose phosphate isomerase, *Rhizopus miehei* lipase, *Aspergillus niger* or *A. awamori* glucoamylase (glaA), *Fusarium oxysporum* trypsin-like protease, *Chrysosporium lucknowense* cellobiohydrolase 1 promoter, *Trichoderma reesei* cellobiohydrolase I (Cel7A) etc.

In yeast, for example promoters of *S. cerevisiae* enolase (ENO-1), galactokinase (GAL1), alcohol dehydrogenase (ADH2) and 3-phosphoglycerate kinase can be used to provide expression.

Examples of promoter sequences for directing the transcription of the serine protease of the invention in a bacterial host are the promoter of lac operon of *Escherichia coli*, the *Streptomyces coelicolor* agarase dagA promoter, the promoter of the *B. licheniformis* alpha-amylase gene (amyL), the promoter of the *B. stearothermophilus* maltogenic amylase gene (amyM), the promoters of the *B. sublitis* xylA and xylB genes, etc.

Suitable terminators include those of the above mentioned genes or any other characterized terminator sequences functional in the host strain.

Suitable transformation or selection markers include those which complement a defect in the host, for example the dal genes from *B. subtilis* or *B. licheniformis* or *Aspergillus* amdS and niaD. The selection may be based also on a marker conferring antibiotic resistance, such as ampicillin, kanamycin, chloramphenicol, tetracycline, phleomycin or hygromycin resistance.

Extracellular secretion of the serine protease of the invention is preferable. Thus, the recombinant vector comprises sequences facilitating secretion in the selected host. The signal sequence of the serine protease of the invention or the presequence or prepeptide may be included in the recombinant expression vector or the natural signal sequence may be replaced with another signal sequence capable of facilitating secretion in the selected host. Thus, the chosen signal sequence may be homologous or heterologous to the expression host.

Examples of suitable signal sequences are those of the fungal or yeast organisms, e.g. signal sequences from well expressed genes. Such signal sequences are well known from the literature.

The recombinant vector may further comprise sequences facilitating integration of the vector into the host chromosomal DNA to obtain stable expression.

The Tr Prb1 protease of the invention was expressed with the signal sequence from the *T. reesei* cbh1 (cel7A) promoter as described in Example 1. The expression construct used to transform the *T. reesei* host included also cbh1 terminator and amdS marker for selecting the transformants from the untransformed cells.

The present invention relates also to host cells comprising the recombinant expression vector as described above. Suitable hosts for production of the fungal serine protease enzyme are homologous or heterologous hosts, such as the microbial hosts including bacteria, yeasts and fungi. Production systems in plant or mammalian cells are also possible.

Filamentous fungi, such *Trichoderma, Aspergillus, Fusarium, Humicola, Chrysosporium, Neurospora, Rhizopus, Penicillium* and *Mortiriella*, are preferred production hosts due to the ease of down-stream processing and recovery of the enzyme product. Suitable expression and production host systems are for example the production system developed for the filamentous fungus host *Trichoderma reesei* (EP 244234), or *Aspergillus* production systems, such as *A. oryzae* or *A. niger* (WO 9708325, U.S. Pat. No. 5,843,745, U.S. Pat. No. 5,770,418), *A. awamori, A. sojae* and *A. japonicus*-type strains, or the production system developed for *Fusarium*, such as *F. oxysporum* (Malardier et al., 1989) or *F. venenatum*, and for *Neurospora crassa, Rhizopus miehei, Mortiriella alpinis, H. lanuginosa* or *H. insolens* or for *Chrysosporium lucknowense* (U.S. Pat. No. 6,573,086). Suitable production systems developed for yeasts are systems developed for *Saccharomyces, Schizosaccharomyces* or *Pichia pastoris*. Suitable production systems developed for bacteria are a production system developed for *Bacillus*, for example for *B. subtilis, B. licheniformis, B. amyloliquefaciens*, for *E. coli*, or for the actinomycete *Streptomyces*. Preferably the serine protease of the invention is produced in a filamentous fungal host of the genus *Trichoderma* or *Aspergillus*, such as *T. reesei*, or *A. niger, A. oryzae, A. sojae, A. awamori* or *A. japonicus*-type strains. According the most preferred embodiment of the invention the fungal serine protease enzyme is produced in *T. reesei*.

The host may be free of homogenous proteases due to removal of proteases either by inactivation or removal of one or more host proteases, e.g. by deletion of the gene(s) encoding such homogenous or homologous proteases.

The present invention relates also to a process for producing a polypeptide for use for modifying, degrading or removing proteinaceous material in industrial applications, where performance of the enzyme at low or moderate temperatures is desirable, preferably for use as a detergent additive, said polypeptide having serine protease activity, and said process comprising the steps of culturing the natural or recombinant host cell carrying the recombinant expression vector for a serine protease of the invention under suitable conditions and optionally isolating said enzyme. The production medium may be a medium suitable for growing the host organism and containing inducers for efficient expression. Suitable media are well-known from the literature.

The invention relates to a Tr Prb1 polypeptide for use for modifying, degrading or removing proteinaceous material in applications at low or moderate temperatures, preferably for use as a detergent additive, which polypeptide has serine protease activity and is encoded by the nucleic acid molecule of the invention and is obtainable by the process described above. Preferably, the polypeptide is a recombinant protease enzyme obtained by culturing the host cell carrying the recombinant expression vector for a serine protease of the invention.

The recombinant enzyme of the invention has a molecular mass between 25 and 35 kDa. The enzyme has optimal temperature at a range from 30° C. to 70° C. at pH 9. Said enzyme has pH optimum at the pH range of at least pH 6 to pH 11 at 50° C. The temperature and pH optima were determined using 15 min reaction time and casein as a substrate. The serine protease of the invention is capable in modifying, degrading or removing proteinaceous stains in the presence of detergent between 10° C. and 60° C.

The invention further relates to a process for obtaining an enzyme preparation comprising a polypeptide for use for modifying, degrading or removing proteinaceous material in applications at low or moderate temperatures, preferably for use as a detergent additive, which polypeptide has serine protease activity, and said process comprises the steps of culturing a host cell carrying the expression vector of the invention and either recovering the polypeptide from the cells or separating the cells from the culture medium and obtaining the supernatant having serine protease activity.

The present invention relates also to an enzyme preparation for use for modifying, degrading or removing proteinaceous material in applications at low or moderate temperatures, preferably for use as a detergent additive, which enzyme preparation comprises the serine protease enzyme characterized above. The enzyme preparation or composition has serine protease activity and is obtainable by the process according to the invention. Preferably, the enzyme composition comprises the recombinant serine protease enzyme obtained by culturing a host cell, which carries the recombinant expression vector of the invention.

Said enzyme preparation may further comprise different types of enzymes in addition to the serine protease of this invention, for example another protease, an amylase, a lipase, a cellulase, a cutinase, a pectinase, a mannanase, a xylanase and/or an oxidase such as a laccase or peroxidase with or without a mediator. These enzymes are expected to enhance the performance of the serine proteases of the invention by removing the carbohydrates and oils or fats present in the material to be handled. Said enzymes may be natural or recombinant enzymes produced by the host strain or may be added to the culture supernatant after the production process.

Said enzyme preparation may further comprise a suitable additive selected from the group of surfactants or surface active agent, buffers, anti-corrosion agents, stabilizers, bleaching agents, mediators, builders, caustics, abrasives and preservatives, optical brighteners, antiredeposition agents, dyes, pigments, etc.

Surfactants are useful in emulsifying grease and wetting surfaces. The surfactant may be a non-ionic including semi-polar and/or anionic and/or cationic and/or zwitterionic.

Buffers may be added to the enzyme preparation to modify pH or affect performance or stability of other ingredients.

Suitable stabilizers include polyols such as propylene glycol or glycerol, a sugar or sugar alcohol, lactic acid, boric acid, or boric acid derivatives, peptides, etc.

Bleaching agent is used to oxidize and degrade organic compounds. Examples of suitable chemical bleaching systems are $H_2O_2$ sources, such as perborate or percarbonate with or without peracid-forming bleach activators such as tetraacetylethylenediamine, or alternatively peroxyacids, e.g. amide, imide or sulfone type. Chemical oxidizers may be replaced partially or completely by using oxidizing enzymes, such as laccases or peroxidases. Many laccases do not function effectively in the absence of mediators.

Builders or complexing agents include substances, such as zeolite, diphosphate, triphosphate, carbonate, citrate, etc. The enzyme preparation may further comprise one or more polymers, such as carboxymethylcellulose, poly(ethylene glycol), poly(vinyl alcohol), poly(vinylpyrrolidone), etc. Also, softeners, caustics, preservatives for preventing spoilage of other ingredients, abrasives and substances modifying the foaming and viscosity properties can be added.

According to one preferred embodiment of the invention said enzyme preparation is in the form of liquid, powder or granulate.

The fungal serine protease of the present invention may like other proteases, particularly alkaline proteases be used in the detergent, protein, brewing, meat, photographic, leather, dairy and pharmaceutical industries (Kalisz, 1988; Rao et al., 1998). For example, it may be used as an alternative to chemicals to convert fibrous protein waste (e.g. horn, feather, nails and hair) to useful biomass, protein concentrate or amino acids (Anwar and Saleemuddin, 1998). The use of fungal serine protease of the present invention may like other enzymes prove successful in improving leather quality and in reducing environmental pollution and saving energy and it may be useful in synthesis of peptides and resolution of the mixture of D,L-amino acids. Subtilisin in combination with broad-spectrum antibiotics in the treatment of burns and wounds is an example of the use of serine proteases in pharmaceutical industry, therefore the fungal serine protease of the present invention may also find such use and may also like alkaline proteases be applicable in removal of blood on surgical equipments and cleaning contact lenses or dentures. Like alkaline protease from *Conidiobolus coronatus*, the fungal serine protease of the present invention may be used for replacing trypsin in animal cell cultures. The proteases of the invention can also be used in cleaning of membranes and destruction of biofilms. In baking the proteases can be used e.g. in destruction of the gluten network and in other food applications in hydrolysis of food proteins, e.g. proteins in milk. They can also be used e.g. in treating yeast, rendering (extracting more protein from animal bones), creating new flavours, reducing bitterness, changing emulsifying properties, generating bioactive peptides and reducing allergenicity of proteins. The substrates include animal, plant and microbial proteins.

Detergent industry, particularly the laundry detergent industry, has emerged as the single major consumer of proteases active at high pH range (Anwar and Saleemuddin, 1998). The ideal detergent protease should possess broad substrate specificity to facilitate the removal of large variety of stains due to food, grass, blood and other body secretions. It has to be active in the pH and ionic strength of the detergent solution, the washing temperature and pH, and tolerate mechanical handling as well as the chelating and oxidizing agents added to detergents. The pI of the protease must be near the pH of the detergent solution. Due to present energy crisis and the awareness for energy conservation, it is currently desirable to use the protease at lower temperatures.

The present invention relates also to the use of the serine protease enzyme or the enzyme preparation for detergents, treating textile fibers, for treating wool, for treating hair, for treating leather, for treating feed or food, or for any application involving modification, degradation or removal of proteinaceous material.

One preferred embodiment of the invention is therefore the use of the serine protease enzyme as characterized above as a detergent additive useful for laundry detergent and dish wash compositions, including automatic dish washing compositions.

A detergent is a substance or material intended to assist cleaning or having cleaning properties. The term "detergency" indicates presence or degree of cleaning property. The degree of cleaning property can be tested on different proteinaceous or protein containing substrate materials or stains or stain mixtures bound to solid, water-insoluble carrier, such as textile fibers or glass. Typical proteinaceous material includes blood, milk, ink, egg, grass and sauces. For testing purposes mixtures of proteinaceous stains are commercially available. The function of the detergent enzyme is to degrade and remove the protein-containing stains. Test results depend on the type of stain, the composition of the detergent and the nature and status of textiles used in the washing test (Maurer, 2004).

Typically, the protease or wash performance is measured as "stain removal efficiency" or "stain removal effect" or "degree of cleaning property" meaning a visible and measurable increase of lightness or change in color of the stained material, e.g. in artificially soiled swatches or test cloths. Lightness or change in color values can be measured, for example by measuring the color as reflectance values with a spectrophotometer using L*a*b* color space coordinates as described in Examples 4 to 7. Fading or removal of proteinaceous stain indicating of the protease performance (stain removal efficiency) is calculated for example as ΔL*, which means lightness value L* of enzyme treated fabric minus lightness value L* of fabric treated with washing liquor (buffer or detergent solution) without enzyme (enzyme blank or control). The presence of detergent may improve the performance of the enzyme in removing the stains.

The serine protease of the present invention degrades various kinds of proteinaceous stains under conditions of neutral and alkaline pH and in the absence or presence of detergents with different compositions (as shown in Examples 4 to 7). The protease is capable of degrading proteinaceous material also at a broad temperature range, particularly at low temperature ranges, such as 10° C. to 30° C. (Example 4, FIG. 7).

As shown in Example 5 with different liquid detergents the Tr Prb1 serine protease of the invention removed the blood/milk/ink stain at low washing temperatures considerably better than the commercial protease preparations Savinase® Ultra 16L, Purafect® 4000L and Properase® 4000E. FIG. 8 shows the result with Ariel Sensitive and Erisan detergents. FIG. 9A-C shows the result with different dosages of a Base detergent at 30° C. and 9D-E shows the results with detergent concentration 3.3 g/l at 10° C. and 20° C. The enzyme preparations were dosed as activity units.

The performance of the Tr Prb1 protease was tested also in detergent powder at 40° C. and 50° C. at pH approximately 10 as described in Example 6. The ability of the enzyme in removing blood/milk/ink standard stain on polyester-cotton material was assayed. Each enzyme preparation was dosed as activity units (mmol tyrosine/minute/volume). As shown in FIG. 10 the Tr Prb1 protease of the invention is suitable also for powder detergents at very alkaline conditions.

The performance of recombinant Tr Prb1 enzyme preparation produced in *T. reesei* was tested in the presence of liquid base detergent in full scale in a washing machine at 30° C. (Example 7). Nine different protease sensitive tracers for testing side effects are presented in Table 5 and the process conditions in Table 6. Enzyme dosages used in the test trials were calculated both as enzyme activities and as amount of enzyme protein. Results presented in FIGS. 11A-I show that the performance of Tr Prb1 at low temperature and short cycle wash (15 min) was considerably higher with all tested stains compared to commercial protease preparation Purafect® 4000L when the enzyme was dosed as activity. Also if dosing was calculated as amount of added protein (FIG. 12), the stain removal efficiency was similar or slightly better than with Purafect® 4000L.

According to a preferred embodiment of the invention the fungal serine protease of the invention is useful in detergent liquids and detergent powders as shown in Examples 5 to 7. The enzyme of enzyme preparation of the invention may be formulated for use in a hand or machine laundry or may be formulated for use in household hard surface cleaning or preferably in hand or machine dishwashing operations.

The application discloses also a fungal serine protease from *Fusarium graminearum* ALKO1726, obtainable from the strain deposited at Centraalbureau voor Schimmelcultures under accession number CBS 124697.

The optimal temperature of the Fg_ALKO1726 enzyme was from 30° C. to 60° C. (at least 30% of the maximum activity at 50° C.), from 40° C. to 60° C. (at least about 40% of the maximum activity), or at 50° C. (the maximum activity of Fg_ALKO1726) when measured at pH 9 using 15 min reaction time and casein as a substrate as described in Examples 2c, 3 and 8.

The Fg_ALKO1726 serine protease enzyme had pH optimum at a pH range from at least pH 6 to pH 11, showing at least 50% of the maximum activity at pH 9 at 50° C. using 15 min reaction time and casein as a substrate as described in Example 2c and Examples 3 and 8. At least about 60% of the maximum activity was exhibited between pH 7 and pH 10. The predicted pI of Fg_ALKO1726 enzyme of the invention was pI 9.3.

In the presence of a detergent the Fg_ALKO1726 enzyme functioned between 10° C. and 60° C., preferably at or below 50° C. The enzyme functioned also in temperatures at or below 45° C., at or below 40° C., at or below 35° C., or at or below 30° C.

The *F. graminearum* serine protease comprises the amino acid sequence of the mature Fg_ALKO1726 enzyme as defined in SEQ ID NO: 16. The mature serine protease includes amino acids Ala123 to Ala411 of the full length protease characterized in SEQ ID NO: 12. The amino acid sequence of the proenzyme form of Fg_ALKO1726 protease is defined in SEQ ID NO: 14.

The Fg_ALKO1726 serine protease enzyme is encoded by a nucleic acid molecule comprising the nucleotide sequence SEQ ID NO:11, which encodes the Fg_ALKO1726 full length enzyme (SEQ ID NO:12), or the nucleotide sequence SEQ ID NO:13, which encodes the Fg_ALKO1726 proenzyme form (SEQ ID NO:14), or it may be encoded by a nucleic acid molecule comprising the nucleotide sequence SEQ ID NO:15, which encodes the mature Fg_ALKO1726 polypeptide (SEQ ID NO:16).

The Fg prtS8A gene encoding Fg_ALKO1726 serine protease was isolated by PCR and using primers specific to the sequence XM__383491 as described in Example 1. The full-length Fg prtS8A gene was included in the plasmid pALK2707 deposited in E. coli RF8098 to the DSMZ culture collection under accession number DSM 22636. The deduced amino acid sequence of the serine protease was analyzed from the DNA sequence.

The nucleotide sequence of the full length Fg prtS8A (SEQ ID NO: 11) and the deduced sequence (SEQ ID NO: 12) are presented in FIG. 2A-B. The length of the gene is 1292 bp (including the stop codon). One putative intron was found having the length of 56 bps. The deduced protein sequence consists of 411 amino acids including a predicted signal sequence of 20 amino acids (SignalP V3.0; Nielsen et al., 1997 and Nielsen and Krogh, 1998) and a propeptide from Ala21 to Ala123. The predicted molecular mass was 29 kDa for the mature polypeptide and the predicted pI was 9.30. These predictions were made using the Compute pI/MW tool at ExPASy server (Gasteiger et al., 2003). The deduced amino acid sequence contained three possible N-glycosylation sites (Asn77, Asn254 and Asn 398), but according to CBS Server NetNGlyc V1.0 only one site, Asn77 (located in the pro sequence) is probable. The homologies to the published protease sequences were searched using the BLASTP program, version 2.2.21 at NCBI (National Center for Biotechnology Information) (Altschul et al., 1990). The identity values of the mature Fg_ALKO1726 sequence to the corresponding regions of homologous sequences were obtained by using ClustalW alignment (Matrix: BLOSUM, Gap open: 10, Gap extension: 0.5 (e.g. in www.ebi.ac.uk/Tools/Clustalw).

The identity of Fg_ALKO1726 sequence with the *Gibberella zeae* hypothetical protein XP_383491 was 99%. Two differences in the amino acid sequences of the mature polypeptides were found, amino acid 188 being Ser in Fg_ALKO1726 and Ala in XP_383491, and amino acid 289 being Phe in Fg_ALKO1726 and Leu in XP_383491. The Fg_ALKO1726 mature sequence showed 72 to 78% identity to an alkaline protease from *T. hamatum* (AAP15044; Steyaert et al., 2004), serine endopeptidase from *Hypocrea lixii* (teleomorph *T. harzianum*; CAL25580; Suarez et al. 2007), alkaline proteinase from *T. atroviride* (ALP_TRIAT; Geremia et al., 1993) and extracellular serine protease Tvsp1 from *Hypocrea virens* (AAO63588; Pozo et al., 2004). The identity of Fg_ALKO1726 mature amino acid sequence to the corresponding region of ALP protease (EMBL accession no. M87516; Geremia et al. 1993; disclosed as SEQ ID No: 313 in U.S. 60/818,910 (Catalyst Bioscience Inc.)) was 76%. The identity between Tr Prb1 and Fg_ALKO1726 mature sequences was 76%.

The enzyme preparation containing Fg_ALKO1726 protease was produced in *T. reesei* under the control of *T. reesei* cbh1 (cel7A) promoter as described in Example 2. The spent culture medium from laboratory scale bioreactor cultivations was used in testing the performance of Fg_ALKO1726 in laundry washings with or without a detergent. As shown in Examples 4-6, in different test conditions the performance of Fg_ALKO1726 serine protease preperation was at least as good as or slightly better than the commercial protease preparations Savinase® Ultra 16L, Purafect® 4000L or Properase® 4000E. However, the stain removal effect was lower than obtained with the enzyme preparation containing the Tr Prb1 serine protease of the invention.

EXAMPLE 1

Cloning of the *Trichoderma reesei* QM6a prb1 (Tr prb1) and *Fusarium graminearum* ALKO1726 Fg prtS8A Protease Genes (a) Isolation of DNA and Molecular Biology Methods Used Standard molecular biology methods were used in the isolation and enzyme treatments of DNA (e.g. isolation of plasmid DNA, digestion of DNA to produce DNA fragments), in *E. coli* transformations, sequencing etc. The basic methods used were either as described by the enzyme, reagent or kit manufacturer or as described in the standard molecular biology handbooks, e.g. Sambrook and Russell (2001). Isolation of genomic DNAs from *T. reesei* QM6a and *F. graminearum* ALKO1726 was done as described by Raeder and Broda (1985). The phenol extraction stage was performed using PhaseLock tubes (Eppendorf, Germany).

(b) Oligonucleotide Primers for Gene Cloning

The Tr prb1 and Fg prtS8A genes were cloned by PCR using the *T. reesei* QM6a and *F. graminearum* ALKO1726 genomic DNA preparations as templates. The PCR primers for cloning the Tr prb1 gene were designed according to the sequence of prb1 (ID 121495), published by DOE Joint Genome Institute (*T. reesei* QM6a genome sequence v2.0, genome.jgi-psf.org/Trire2/Trire2.home.html). The PCR primers for cloning the Fg prtS8A gene were designed according to the sequence XM.sub.-383491, previously published in EMBL database and obtained from *Gibberella zeae* PH-1 (anamorph: *Fusarium graminearum*). The XM.sub.-383491 is described in the database as a partial mRNA which encodes a hypothetical protein EAA71059. The sequences of primers used in cloning the Tr prb1 and Fg prtS8A genes are shown in Table 1. The 5'-PCR primers PRO213 and PRO245 included (from 5'- to 3'-direction), respectively, the end of the cbh1 promoter sequence (from SacII site) fused to the beginning of the Tr prb1 and Fg prtS8A gene sequences (26 and 27 nucleotides including ATG, respectively). In addition, the primers contained three (PRO213) or two (PRO245) additional nucleotides at their 5'-ends to ensure the cleavage of PCR products from the SacII site and enable the exact fusion of the genes to the SacII site of the full-length cbh1 promoter. The 3'-PCR primers PRO214 and PRO246 included (from 5'- to 3'-direction), respectively, the BamHI site and the end of the Tr prb1 and Fg prtS8A genes (26 or 25 nucleotides including the STOP codon, respectively). In addition, PRO214 contained three and PRO246 two additional nucleotides at the 5'-ends to ensure cleavage from the BamHI site which was used in fusing the genes to cbh1 terminator via a linker.

TABLE 1

Oligonucleotides (SEQ ID NOs: 1-4) used as PCR primers in cloning of the Tr prb1 and Fg prtS8A genes. The primers, their corresponding SEQ ID NOs, and sequences (5' -> 3') are shown. The sequences deriving from the Tr prb1 and Fg prtS8A genes are in bold letters.

| Oligonu-cleotide | SEQ ID NO: | Sequence |
|---|---|---|
| PRO213 | 1 | TCCCCGCGGACTGCGCATCATGGCCAGCCTTCGTC GCCTTGCCCT |
| PRO214 | 2 | CGCGGATCCTTAAGCACTGTTCCCGTTGAAGATGA |
| PRO245 | 3 | ACCCGCGGACTGCGCATCATGACCAGCTTCCGCCG TCTTGCTCTC |
| PRO246 | 4 | CGGGATCCTTAAGTAGAGGCACCGTTGAAGGCG |

(c) PCR Reactions

*T. reesei* QM6a and *F. graminearum* ALKO1726 (CBS 124697) genomic DNAs were used as templates in the PCR reactions. The PCR reaction mixtures contained 1× Phusion HF buffer (Finnzymes, Finland), 0.2 mM dNTPs, 0.5 µM each primer and 0.5 units of Phusion DNA polymerase (Finnzymes, Finland) and approximately 0.5-1 µg of genomic DNA per 50 µl reaction volume. The conditions for the PCR reactions were the following: 30 s initial denaturation at 98° C., followed by 25 cycles of 10 s at 98° C., 30 s annealing at 49.4, 54.7 and 60.2° C. (Tr prb1) or 54.4, 59.5 and 64.8° C. (Fg prtS8A), 1 mM extension at 72° C. and a final extension at 72° C. for 7 min. DNA products having the expected sizes (according to calculations basing on published sequences), ~1.4 and ~1.3 kb, respectively were obtained from all the reactions using the primer combinations PRO213 (SEQ ID NO:1) with PRO214 (SEQ ID NO:2) and PRO245 (SEQ ID NO:3) with PRO246 (SEQ ID NO:4). The DNA products were isolated and purified from the PCR reaction mixtures. They were cleaved using SacII and BamHI and ligated to pALK1910 vector cleaved with SacII and BamHI. The pALK1910 includes a ~2.2 kb cbh1 promoter (to SacII site) and a linker (including e.g. BamHI site) enabling ligation of a gene to the cbh1 promoter and terminator (~0.6 kb, from STOP to AvaII site). The products from two separate *T. reesei* PCR reactions were sequenced and found to be identical with each other and with the sequence published by DOE Joint Genome Institute. Also the products from two separate *F. graminearum* PCR reactions were sequenced and found to be identical with each other. The plasmids including the Tr prb1 and Fg prtS8A genes fused to cbh1 promoter and terminator were named as pALK2650 and pALK2707, respectively. The *E. coli* strains RF8052 and RF8098 including the plasmids pALK2650 and pALK2707 were deposited to the DSM collection under the accession numbers DSM 22635 and DSM 22636, respectively. The expression cassettes pALK2701 (Tr prb1) and pALK2708 (Fg prtS8A) were further constructed from these plasmids as described in Example 2.

(d) Characterisation of the Genes Encoding the Tr Prb1 and Fg_ALKO1726 Proteases and the Deduced Amino Acid Sequences The Tr prb1 sequence (SEQ ID NO:5) and the deduced amino acid sequence (SEQ ID NO:6) are shown in FIGS. 1A-B. The length of the gene is 1371 bp (including the stop codon). The gene contains two introns of 68 and 73 bp. The deduced amino acid sequence consists of 409 amino acids including a predicted signal sequence of 20 amino acids (genome.jgi-psf.org/Trire2/Trire2.home.html and SignalP V3.0; Nielsen et al., 1997 and Nielsen and Krogh, 1998). The predicted molecular mass was 29062.21 Da for the mature polypeptide and the predicted pI was 8.94. These predictions were made using the Compute pI/MW tool at ExPASy server (Gasteiger et al., 2003). The deduced amino acid sequence contained two possible N-glycosylation sites at amino acid positions Asn252 and Asn396 (FIG. 1), but according to CBS Server NetNGlyc V1.0 only predicts the site at position Asn252 as potential N-glycosylation site.

The Fg prtS8A sequence (SEQ ID NO: 11) and the deduced amino acid sequence (SEQ ID NO: 12) are shown in FIG. 2A-B. The length of the gene is 1292 bp (including the stop codon). The gene contains one putative intron of 56 bp (5' and 3' border sequences according to those of fungal introns, according to Gurr et al., 1987). The deduced amino acid sequence consists of 411 amino acids including a predicted signal sequence of 20 amino acids (SignalP V3.0; Nielsen et al., 1997 and Nielsen and Krogh, 1998). The predicted molecular mass was 28935.98 Da for the mature polypeptide and the predicted pI was 9.30. These predictions were made using the Compute pI/MW tool at ExPASy server (Gasteiger et al., 2003). The deduced amino acid sequence contained three possible N-glycosylation sites at amino acid positions Asn77, Asn254 and Asn398 (FIG. 2), but according to CBS Server NetNGlyc V1.0 only predicts the site at position Asn77 (located in the pro-sequence) as a potential N-glycosylation site.

(e) Homology, Identity and Alignment Studies

The homologies of the sequences encoding the mature Tr Prb1 and Fg_ALKO1726 proteins to the published protease sequences (non-redundant GenBank CDS translations+ PDB+SwissProt+PIR+PRF excluding environmental samples from WGS projects) were searched using the protein BLASTP program version 2.2.21 at NCBI (National Center for Biotechnology Information) with default settings (Altschul et al., 1990). The highest identities (92-93%) for Tr Prb1 were as follows: an alkaline proteinase from *Trichoderma hamatum* (AAP15044; Steyaert et al., 2004), serin endopeptidase from *Hypocrea lixii* (*Trichoderma harzianum*; CAL25580; Suarez et al., 2007), alkaline proteinase from *Trichoderma atroviride* (ALP_TRIAT; Geremia et al., 1993) and extracellular serine protease Tvsp1 from *Hypocrea virens* (AAO63588; Pozo et al., 2004). The identities for Fg_ALKO1726 with the hypothetical protein from *Gibberella zeae* (*Fusarium graminearum*) XP_383491 sequence were 99%. Only two differences were detected in the amino acid sequences of the above two mature amino acid sequences (amino acid 188 is Ser in Fg_ALKO1726 and Ala in XP_383491 and amino acid 289 Phe in Fg_ALKO1726 and Leu in XP_383491). The next closest homologues to Fg_ALKO1726 were found to be the Tr Prb1 homologues (see above). The identities of the Fg_ALKO1726 mature sequence towards these sequences were from 74 to 78%. Also homology was found to a sequence included in the patent application U.S. 60/818,910 (Catalyst Bioscience Inc.) as SEQ ID NO:313. The identity values of this sequence with the Tr Prb and Fg_ALKO1726, obtained by using mature sequence regions and ClustalW alignment (www.ebi.ac.uk/Tools/clustalw; Matrix: BLOSUM, Gap open: 10, Gap extension: 0.5) were 92% (Tr Prb1) and 76% (Fg_ALKO1726). The identity between Tr Prb1 and Fg_ALKO1726 was 76%, using the above ClustalW alignment.

EXAMPLE 2

Production of the Recombinant Tr Prb1 and Fg_ALKO1726 Proteases in *Trichoderma reesei*

(a) Preparation of the Expression Cassettes and their Transformation into *T. reesei*

Figure 3:
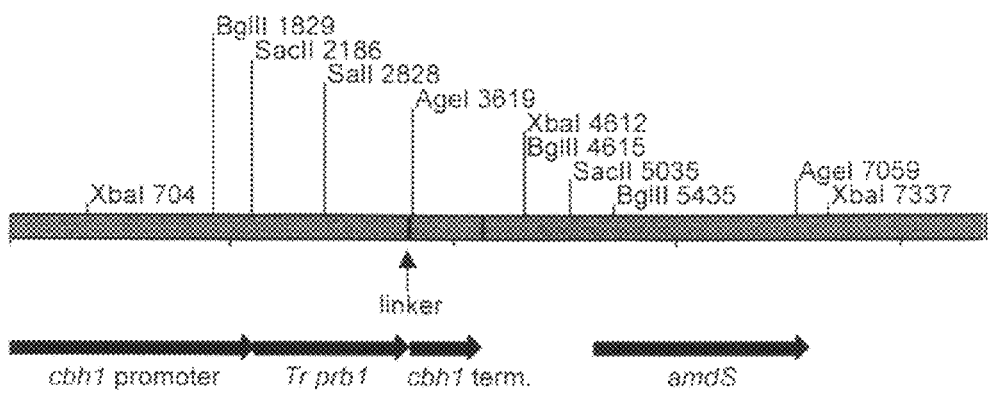
FIG. 3 schematically shows the cassette (8762 bp NotI fragment from pALK2701) used for overexpressing the Tr prb1 gene in *Trichoderma reesei*. The locations of the linker used for fusing the 3'-end of the prb1 gene to cbh1 terminator and a selection of restriction sites in the cassette are shown.
Figure 4:
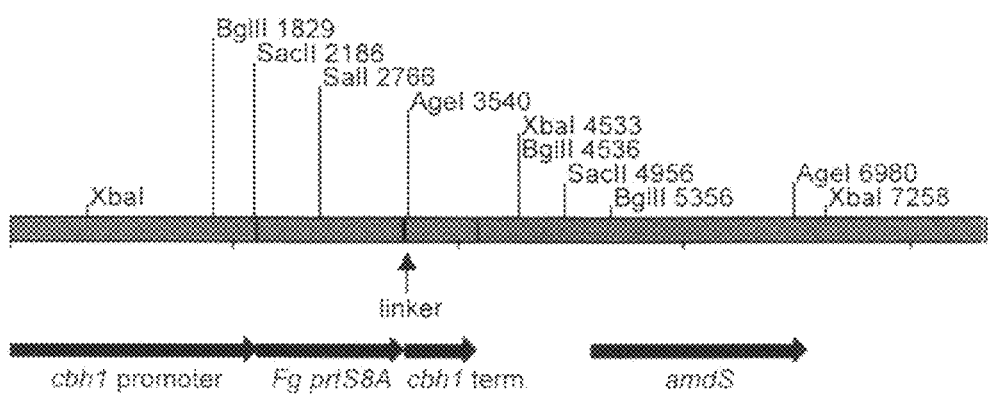
FIG. 4 schematically shows the cassette (8683 bp NotI fragment from pALK2708) used for expressing the Fg prtS8A gene in *Trichoderma reesei*. The locations of the linker used for fusing the 3'-end of the prb1 gene to cbh1 terminator and a selection of restriction sites in the cassette are shown.

The expression plasmids pALK2701 (Tr prb1) and pALK2708 (Fg prtS8A) for production of recombinant Tr Prb1 and Fg_ALKO1726 proteins in *Trichoderma reesei* were constructed by ligating the amdS (acetamidase) marker gene into the plasmids pALK2650 and pALK2707 (Example 1c), respectively. The amdS marker was ligated after the cbh1 terminator into the expression constructions. Analogous constructions have been described in e.g. Paloheimo et al. (2003). In the expression cassettes pALK2701 and pALK2708 (FIGS. 3 and 4), the Tr prb1 and Fg prtS8A genes with their own signal sequences are exactly fused to the *T. reesei* cbh1 (cel7A) promoter by PCR. The 3'-ends of the genes are fused to cbh1 terminator using a BamHI site created after the stop codon in PCR. This leaves no original terminator sequences in the constructions prior to the cbh1 terminator sequence. The ~8.7 kb linear expression cassettes (presented in FIGS. 3 and 4) were isolated from the vector backbones using NotI digestion and were used for transforming *T. reesei* protoplasts. The host strain used does not produce any of the four major *T. reesei* cellulases (CBHI, CBHII, EGI, EGII). The transformations were performed as in Penttilä et al. (1987) with the modifications described in Karhunen et al. (1993). The transformants were purified on selection plates through single conidia prior to sporulating them on PD.

(b) Protease Production in Shake Flasks and Laboratory Scale Bioreator

A selection of transformants were inoculated from the PD slants to shake flasks containing 50 ml of complex lactose-based cellulase inducing medium (Joutsjoki et al., 1993) buffered with 5% $KH_2PO_4$ at pH 6.0. The protease production of the transformants was analyzed from the culture supernatants after growing them for 7 days at 30° C., 250 rpm. In SDS-PAGE gels, a major protein band of about 29 kDa corresponding to the expected molecular mass of the Tr Prb1 and recombinant Fg_ALKO1726 proteases were detected from the spent culture supernatants. The protease activities were assayed from the culture supernatants using casein as a substrate as described in Example 2c or 8. Clearly increased protease activities compared to host were detected. The integration of the expression cassette(s) into the fungal genomes was confirmed from chosen transformants by using Southern blot analysis in which several genomic digests were included and the respective expression cassette was used as a probe.

The *T. reesei* transformants producing the best protease activities in the shake flask cultivations were chosen to be cultivated in laboratory scale bioreactors. Cellulase inducing complex medium was used in the cultivations. The spent culture medium obtained from the cultivations was used in application tests (Examples 4-7) and as starting material for purification and further characterization of the Tr Prb1 and recombinant Fg_ALKO1726 proteases.

(c) Protease Activity Assay

Protease activity was assayed by the casein Folin-Ciocalteau method. Rate of casein degradation by a protease was measured by spectrophotometrical monitoring of the release of acid-soluble fragments as a function of time. Casein substrate used in the assay was prepared as follows: 6 g of Casein Hammerstein Grade MP Biomedicals, LLC (101289) was dissolved in 500 ml of 100 mM Tris, 20 μM $CaCl_2$, 7 μM $MgCl_2$, 25 μM $NaHCO_3$. The pH of the substrate solution was adjusted to 9.0 with HCl. The enzyme reactions were stopped using a TCA solution which contained: 0.11 M TCA, 0.22 M sodium acetate, 0.33 M acetic acid, 0.5 M $Na_2CO_3$ in 1000 ml distilled water. The Folin reagent used in the assay was prepared by diluting 25 ml of 2 N Folin-Ciocalteu's phenol reagent (SIGMA, F 9252) to 100 ml by distilled water. The reaction was started by first incubating 2.5 ml of substrate solution for 5 min at the given temperature after which 0.5 ml of enzyme solution was added and reaction was conducted for 15 min (for determination of temperature or pH profiles) or 30 min. After 15 or 30 min reaction 2.5 ml of reaction stop solution was added, the contents were mixed and allowed to stand for 30 minutes at room temperature. Tubes were centrifuged 4000 rpm for 10 minutes (Hettich Rotanta 460). One ml of clear supernatant was pipetted and mixed with 2.5 ml 0.5 M $Na_2CO_3$ and 0.5 ml diluted Folin reagent. After waiting for 5 min (color development) the absorbance of the mixture (color) was measured at 660 nm against an enzyme blank. The enzyme blank was prepared as follows: 0.5 ml enzyme solution was mixed with 2.5 ml stopping solution and 2.5 ml substrate, and the mixture was incubated for 15 or 30 min at the given temperature. One unit of enzyme activity was defined as the enzyme quantity that liberates the acid soluble protein hydrolysis product corresponding to 1 μg of tyrosine per ml (or g) of the reaction mixture per min.

EXAMPLE 3

Purification and Characterisation of the Recombinant Tr Prb1 and Fg_ALKO1726 Proteases Cells and solids were removed from the spent culture medium obtained from the fermentation (Example 2) by centrifugation for 30 min, 50000 g at +4° C. (Sorvall RC6 plus). 15 ml of the supernatant was used for purification of protease. All purification steps were performed at cold room. After centrifugation, sample was filtered through 0.44 μm filter (MILLEX HV Millipore) before applying to HiPrep 26/10 Desalting column (from GE Healthcare) equilibrated in 20 mM Tris pH 8.8. Gel filtered sample was applied to a 20 mL Q Sepharose FF column (from GE Healthcare) equilibrated in 20 mM Tris pH 8.8. Flow trough fraction with proteolytic activity was concentrated using Amicon Ultra centrifugal filter device 10000 MWCO (Millipore). Concentrated sample was applied into Superdex 75 10/300 GL column (GE Healthcare) and eluted with 20 mM Hepes, 150 mM NaCl pH 6.8. Protease containing fractions were combined and used for characterization of pH and temperature profiles.

Temperature Profiles

Figure 5A:
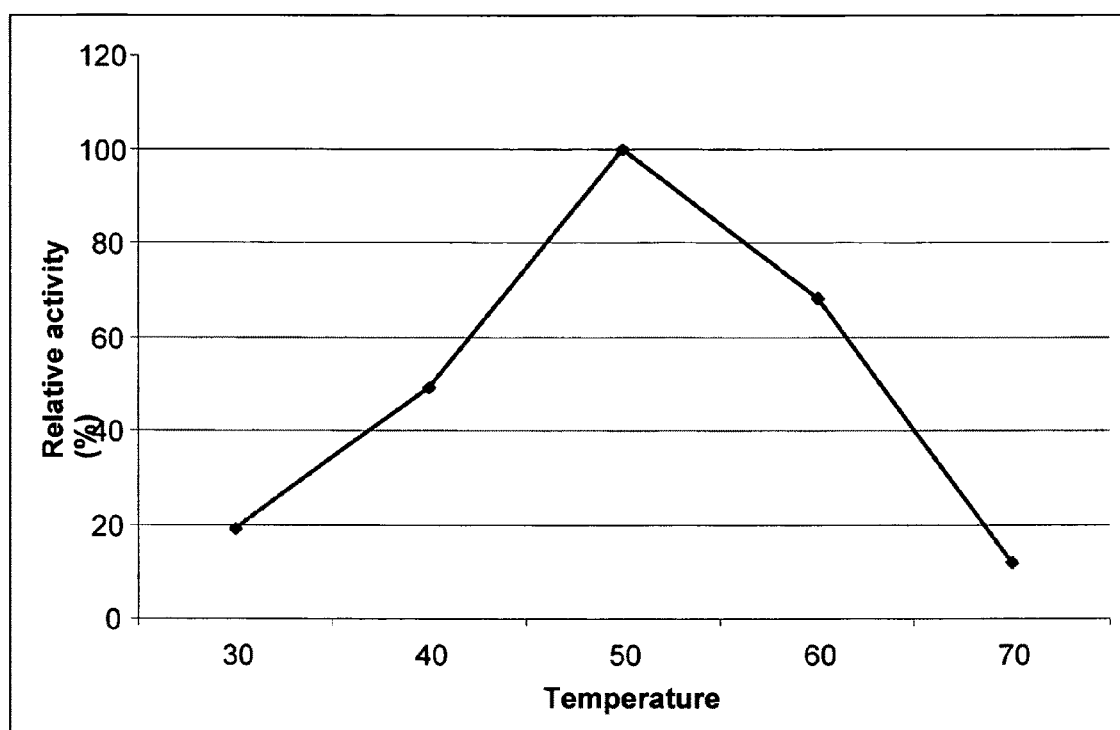
FIG. 5A-B describes the temperature profiles of the *T. reesei* Prb1 (Tr Prb1) and *F. graminearum* Fg_ALKO1726 recombinant proteins assayed at pH 9 using 15 min reaction time and casein as a substrate. The data points are averages of three separate measurements. A shows the results from Tr Prb1 assays. B shows the results from Fg_ALKO1726 assay.
Figure 5B:
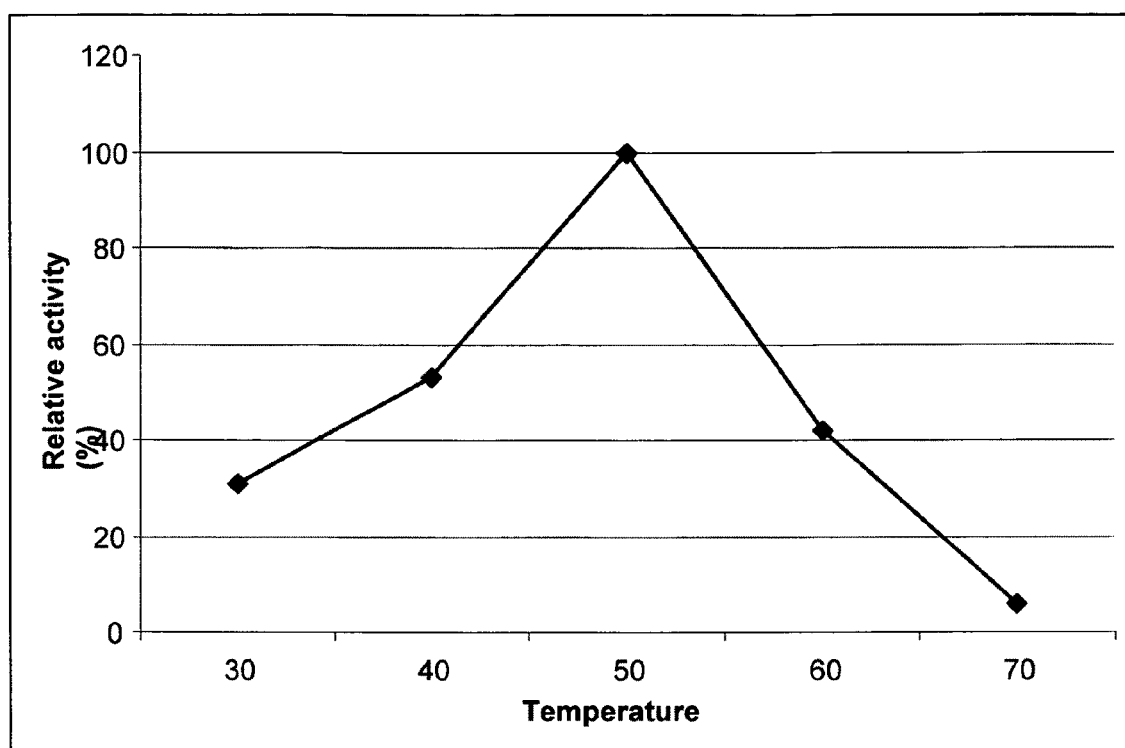

The temperature profiles for the Tr Prb1 and Fg_ALKO1726 proteases were analysed at pH 9 by using the assay described in Example 2c or 8 using 15 min reaction time and 0.11 M TCA stop solution. The results are shown in FIGS. 5A (Tr Prb1) and 5B (Fg_ALKO1726). Both the proteases have their optimal temperatures at around 50° C.

pH-Profiles

Figure 6A:
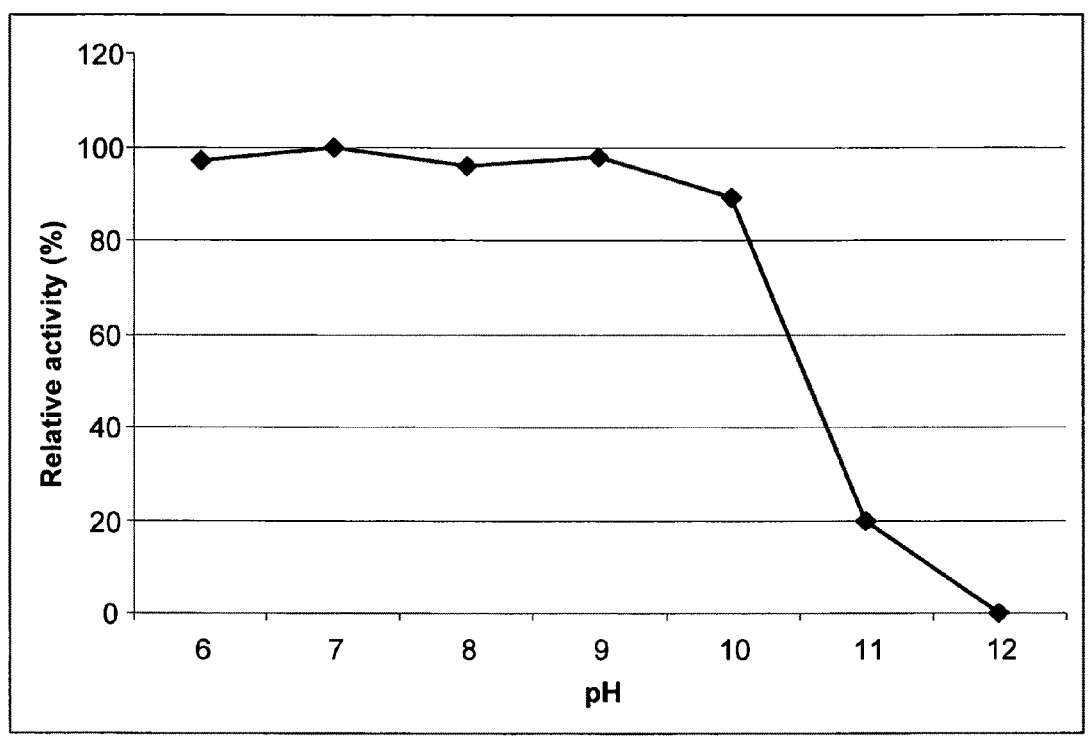
FIG. 6A-B describes the effect of pH on the activity of recombinant Tr Prb1 and Fg_ALKO1726 proteins. The buffer used was 40 mM Britton-Robinson buffer, casein was used as a substrate, reaction time was 15 mM and reaction temperature was 50° C. The data points are averages of three separate measurements. A shows the results from Tr Prb1 assays. B shows the results from Fg_ALKO1726 assay.
Figure 6B:
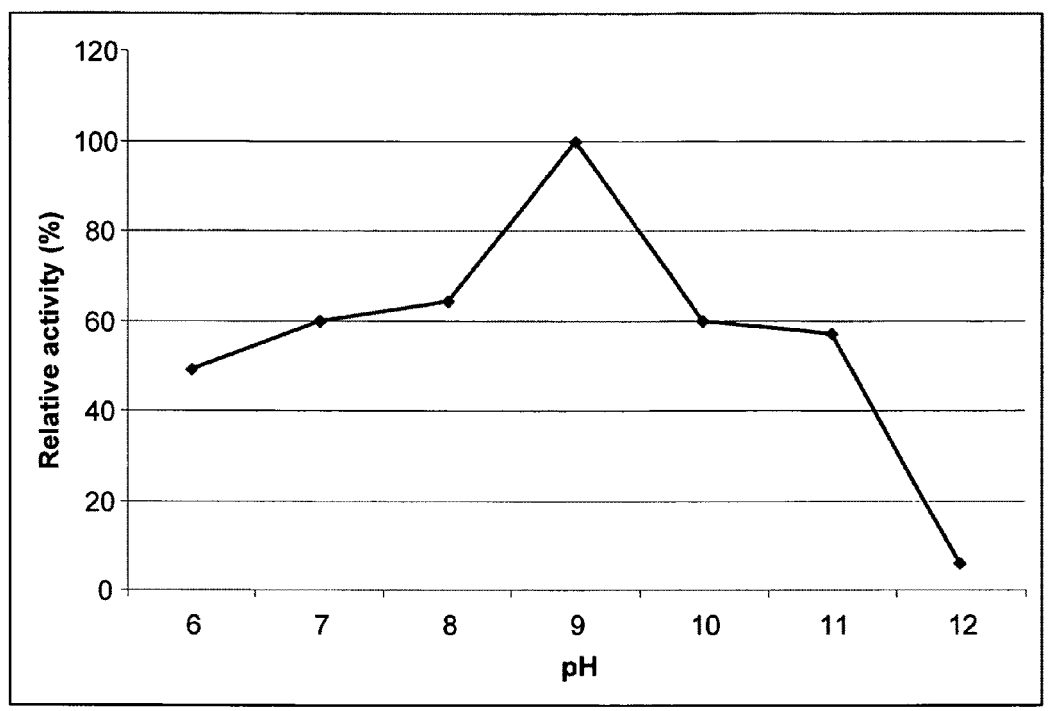
Figure 7A:
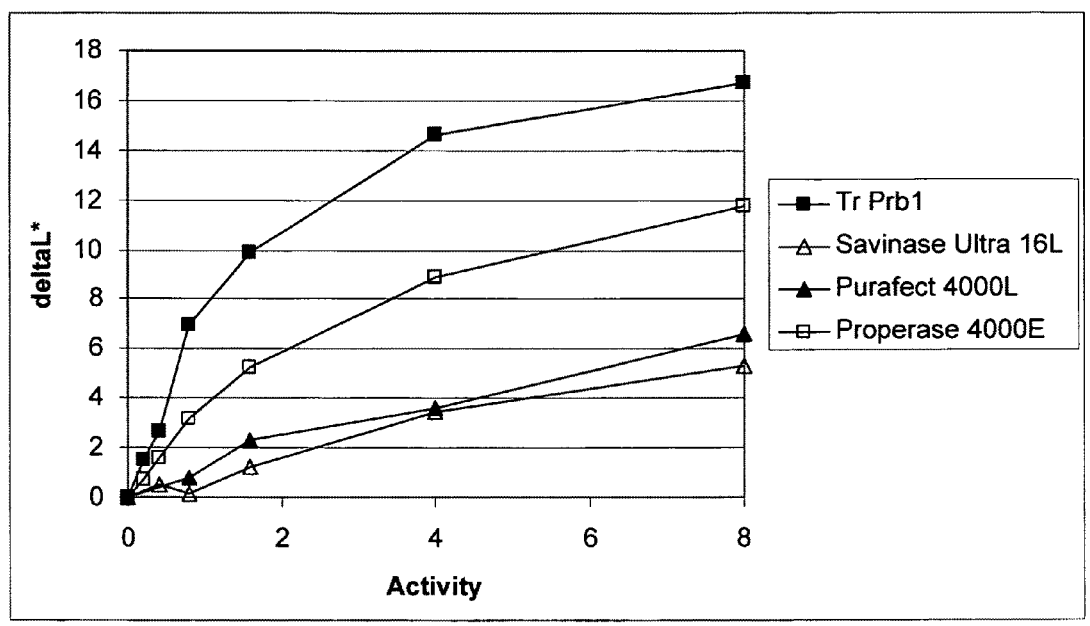
FIG. 7A-F describes the performance of recombinant proteins Tr Prb1 and Fg_ALKO1729 with blood/milk/ink stain (Art 117, EMPA) at different temperatures (pH 9, 60 min). Commercial preparations Savinase Ultra® 16L (Novozymes A/S, DK), Purafect® 4000L (Genencor Inc., USA) and Properase® 4000E (Genencor Inc., USA) were used for comparison. ΔL*(deltaL*)=lightness value L* of enzyme treated fabric–lightness value L* of fabric treated with buffer only (enzyme blank). A shows the performance of recombinant protein Tr Prb1 and commercial protease preparations at 10° C. B shows the performance of recombinant protein Tr Prb1 and Fg_ALKO1729 and commercial protease preparations at 20° C. C shows the performance of recombinant protein Tr Prb1 and Fg_ALKO1729 and commercial protease preparations at 30° C. D shows the performance of recombinant protein Tr Prb1 and Fg_ALKO1729 and commercial protease preparations at 40° C. E shows the performance of recombinant protein Tr Prb1 and commercial protease preparations at 50° C. F shows the performance of recombinant protein Tr Prb1 and commercial protease preparations at 60° C.
Figure 7B:
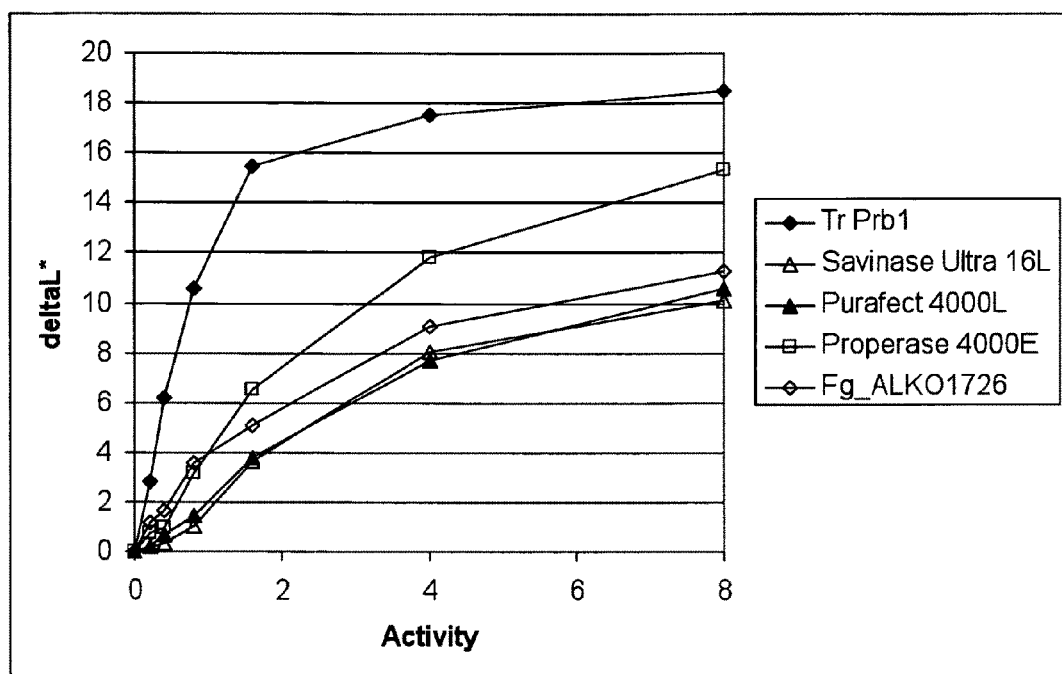
Figure 7C:
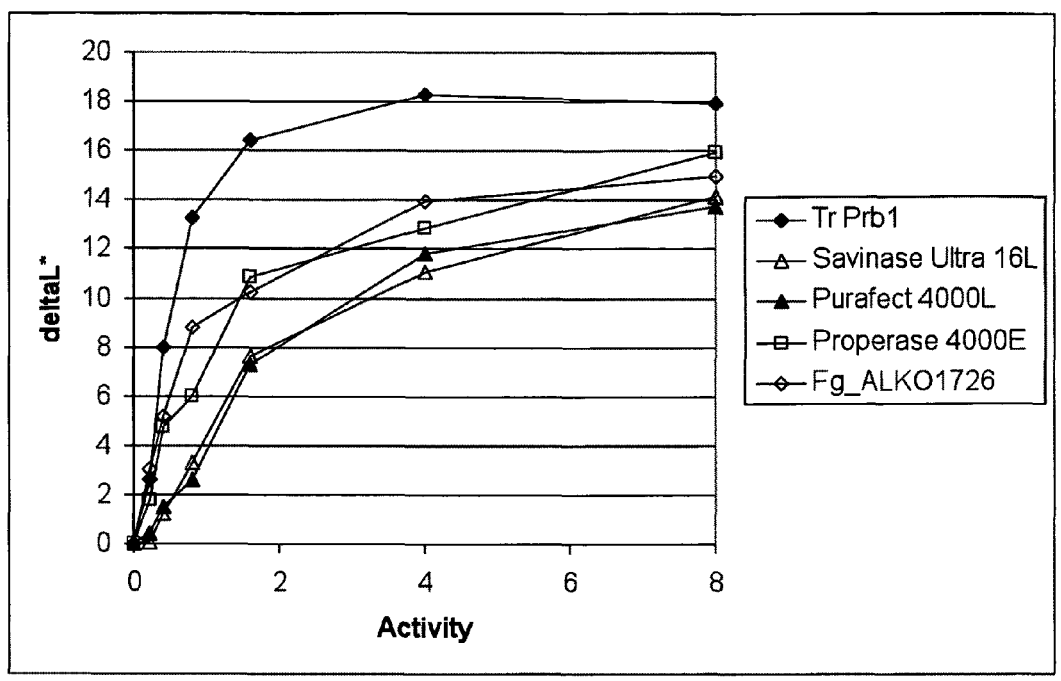
Figure 7D:
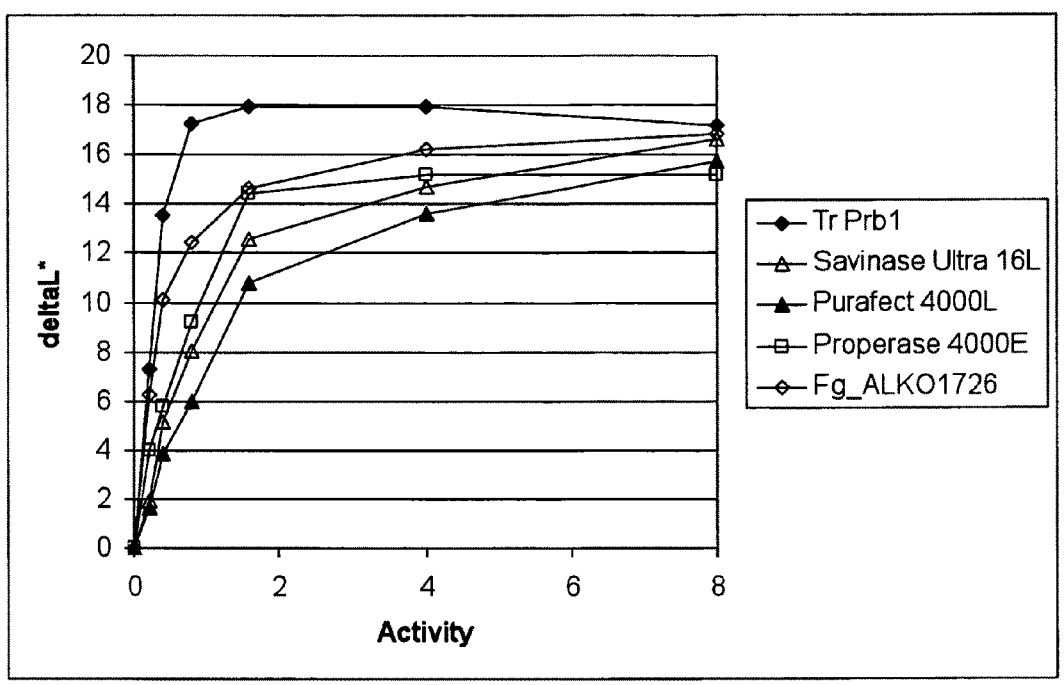
Figure 7E:
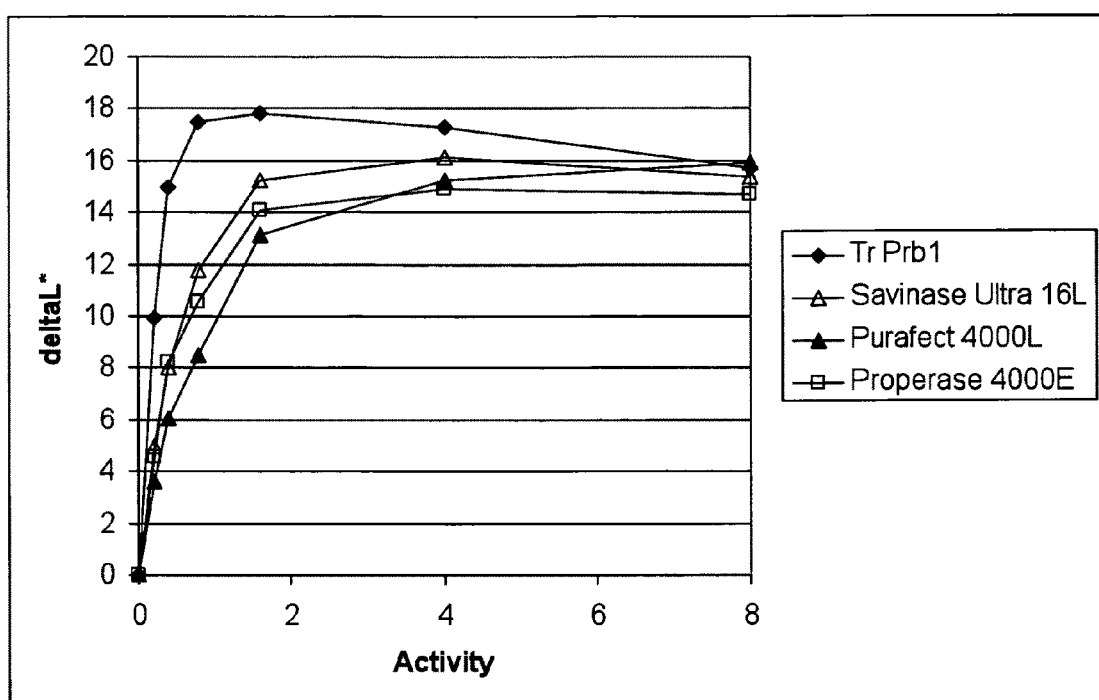
Figure 7F:
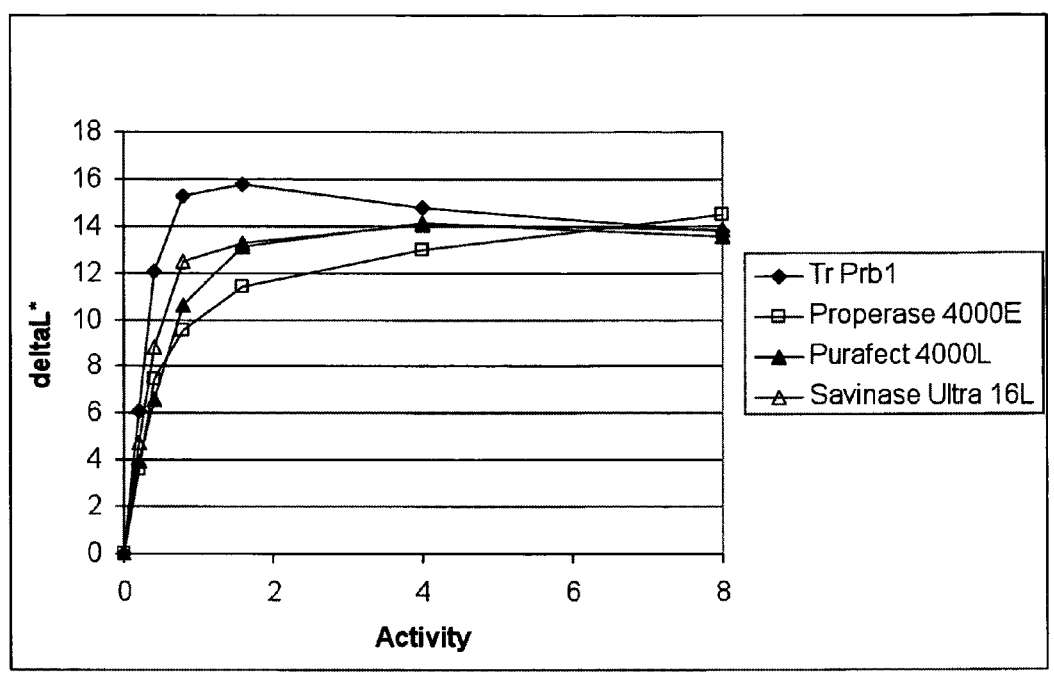

The pH profiles of the proteases were determined at 50° C. using casein as a substrate and 15 min reaction time as described in Example 2c or 8. The pH of the reaction was adjusted to pH 6-12 using 40 mM Britton-Robinson buffer. The 0.11 M TCA stop solution contained 0.22 M sodium acetate and 0.33 M acetic acid. The results are shown in FIGS. 6A (Tr Prb1) and 6B (Fg_ALKO1726). Both proteases were active on broad pH area. The Tr Prb1 exhibits relative activity of over 85% from pH 6 to pH 10. The pH optimum of the Tr Prb1 is broad, it has at least 95% of the maximum activity between pH 6 and pH 9 in the conditions used in the measurements.

EXAMPLE 4

Performance of Recombinant Proteins Tr Prb1 and Fg_ALKO1726 at pH 9 Buffer at Different Temperatures Recombinant proteins Tr Prb1 and Fg_ALKO1726 produced in *Trichoderma* (as described in Example 2 were tested for their ability to remove blood/milk/ink standard stain (Art.117, polyester+cotton, EMPA Testmaterialen AG, Swizerland) at temperatures 10-60° C. or 20-40° C., respectively. Commercial protease preparations Savinase® Ultra 16 L (Novozymes), Purafect® 4000 L (Genencor International) and Properase® 4000 E (Genencor International) and treatment without enzyme (control) were used for comparison. The stain fabric was first cut into 1.5 cm×1.5 cm swatches and the pieces were made rounder by cutting the corners. Pieces were placed in wells of microtiter plates (Nunc 150200). Into each well having diameter of 2 cm, 1.5 ml enzyme dilution in Glysine-NaOH buffer pH 9 was added on top of the fabric. Each enzyme was dosed 0, 0.2, 0.4, 0.8, 1.6, 4, and 8 activity units (µmol tyrosine/min) per 1.5 ml buffer. Activity was measured using 30 min reaction time as described in Example 2(c) or 8. The measurements were performed at pH 8.5 and the stop solution contained 0.11 M TCA. A 10 min incubation time for color development after addition of diluted Folin reagent was used. Microtiter plates with samples were incubated in a horizontal shaker at 10-60° C./20-40° C. for 60 min with 125 rpm. After that the swatches were carefully rinsed under running water (appr. at washing temperature) and dried overnight at indoor air on a grid, protected against daylight.

The stain removal effect was evaluated by measuring the color as reflectance values with Minolta CM 2500 spectrophotometer using L*a*b* color space coordinates (illuminant) D65/2°). The color from both sides of the swatches was measured after the treatment. Each value was the average of at least 2 parallel fabric samples measured from both side of the fabric. Fading of blood/milk/ink stain indicating of the protease performance (stain removal efficiency) was calculated as ΔL*, which means lightness value L* of enzyme treated fabric minus lightness value L* of fabric which was treated with washing liquor (buffer) without enzyme (enzyme blank, control).

The results are shown in FIGS. 7A-F. Tr Prb1 protease preparation showed higher stain removal capacity at whole temperature range from 10 to 60° C. in pH 9 buffer, especially at lowest washing temperatures like 10-30° C., compared to commercial protease preparations Savinase® Ultra 16L, Purafect® 4000L and Properase® 4000E. Fg_ALKO1726 protease preparation was slightly better than protease preparations Savinase® Ultra 16L and Purafect® 4000L at 20-40° C.

EXAMPLE 5

Performance of Recombinant Proteins Tr Prb1 and Fg_ALKO1726 with Different Liquid Detergents at Low Temperatures Recombinant proteins Tr Prb1 and Fg_ALKO1726 produced in *Trichoderma* (as described in Example 2) were tested for their ability to remove blood/milk/ink standard stain (Art.117, cotton+polyester, EMPA) with different liquid detergents at 30° C. Liquid Base detergent (pH>8.0) for colored fabric containing 25% washing active substances, polyol and polymers (Table 2) was used at concentrations of 1-5 g/l and commercial detergents Ariel Sensitive (pH>8.0, Procter & Gamble, UK, Table 3) and Erisan (pH>9.0, Farmos, Finland, Table 4) containing no enzymes were used at concentration of 3.3 g/l. Commercial protease preparations Savinase® Ultra 16L, Purafect® 4000L, Properase® 4000E and treatment without enzyme (control) were used for comparison. Tr Prb1 was also tested at 10 and 20° C. using Base detergent (3.3 g/l). Each enzyme was dosed 0, 0.2, 0.4, 0.8, 1.6, 4, and 8 activity units (µmol tyrosine/min) per ml wash liquor. Activity was measured as described in Example 4. In each experiment, at least two of the dosages of commercial enzymes per wash liquor were equal to dosage of approximately 0.2-0.5% of enzyme preparation per weight of detergent, which is in typical economical use level for detergent enzymes.

TABLE 2

Composition of Liquid Base detergent for colored fabric

| Ingredients | % |
|---|---|
| NaLES (sodium lauryl ether sulphate) | 4.9 |
| Nonionic C12-15 7EO (ethylene oxide) | 15 |
| Na-Soap (Palm Kernel FA) | 4.4 |
| Coco Glucoside | 1 |
| <Total Surfactant> | <25.30> |
| Polyol (Glycerin) | 5 |
| Phosphonate (32%) (ThermPhos) | 2 |
| PVP-Sokalan HP 53 (BASF) | 1 |
| Sokalan PA 15 (BASF) | 1.56 |
| Sorez-100 (ISP) | 0.4 |
| Water up to 100% | |

TABLE 3

Composition of Ariel Sensitive

| Ingredients | % |
|---|---|
| Soap | <5 |
| Optical brighterers | <5 |
| Phosphate | <5 |
| Parfum | <5 |
| Anionic tensides | <5-15% |
| Nonionic tensides | <5-15% |

TABLE 4

Composition of Erisan detergent for delicate and colored fabrics

| Ingredients | % |
|---|---|
| Soap | <5 |
| Citrate | <5 |
| Phosphate | <5 |
| Polycarboxylate | <5 |
| Anionic tensides | <5-15% |
| Nonionic tensides | <5-15% |

Amounts of 1, 3.3 or 5 g of liquid detergent was dissolved in 1 liter of tap water (dH≦4), mixed well with magnetic stirrer and tempered to 30° C. The pH in the wash liquors was approximately 7.3-7.5 with Base detergent depending on detergent concentration.or appr. 7.9 with Ariel and appr. 8.2 with Erisan. Stain fabric was cut into pieces like described in Example 4. Swatches were placed in wells of microtiter plates (Nunc 150200) and 1.5 ml washing liquor containing detergent and enzyme dilution in water (below 60 µl) was added on top of the fabric. The plates with samples were incubated in a horizontal shaker at 30° C. for 60 min with 125 rpm. After that the swatches were carefully/thoroughly rinsed under running water (approx. at the washing temperature) and dried overnight at indoor air, on a grid, protected against daylight. Tests with Base detergent were performed in the same way also at 10° C. and 20° C. using detergent concentration 3.3 g/l.

The color of the swatches after treatment was measured with Minolta CM 2500 spectrophotometer using L*a*b* color space coordinates and stain removal effect calculated as ΔL* as described in Example 4. For treatment without enzyme (enzyme blank), the corresponding detergent solution was used as washing liquor.

Figure 8A:
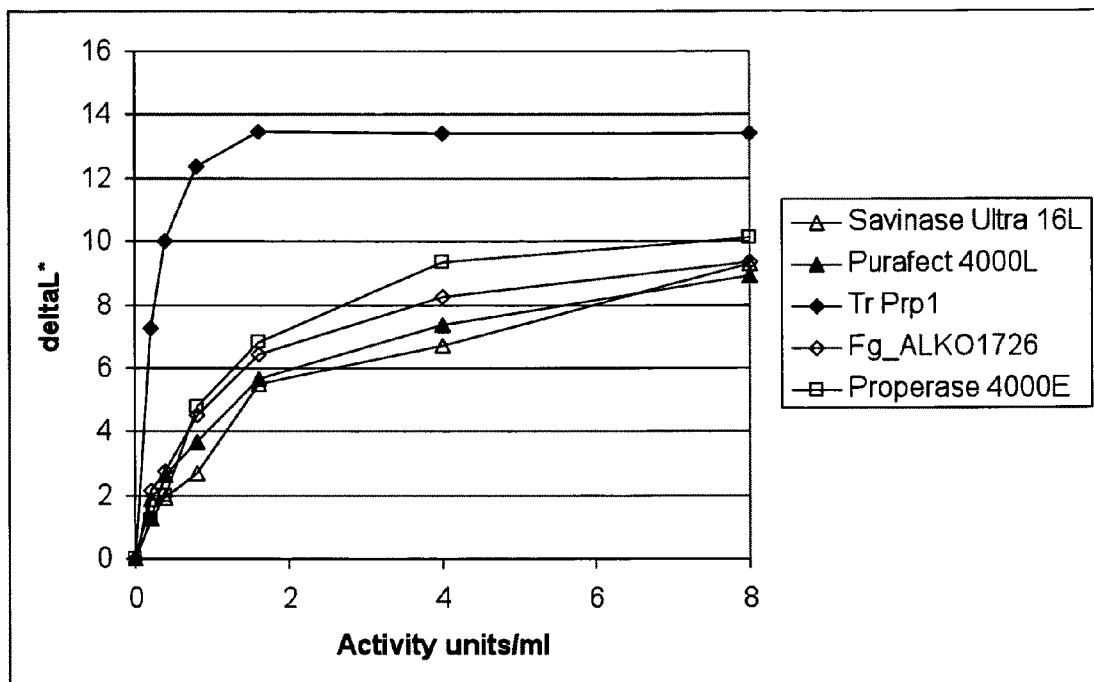
FIG. 8A-B shows the performance of recombinant proteins Tr Prb1 and Fg_ALKO1729 with blood/milk/ink stain (Art 117, EMPA) with different liquid detergents at 30° C. Commercial preparations and Properase® 4000E (Genencor Inc., USA), Purafect® 4000L and Savinase® Ultra 16L were used for comparison. ΔL*(deltaL*)=lightness value L* of enzyme treated fabric–lightness value L* of fabric treated without enzyme. A shows the performance with Ariel sensitive (Procter & Gamble, UK) at concentration of 3.3 g/l and pH appr. 7.9. B shows the performance with Erisan (Farmos, Finland) at concentration of 3.3 g/l and pH appr. 8.2.
Figure 8B:
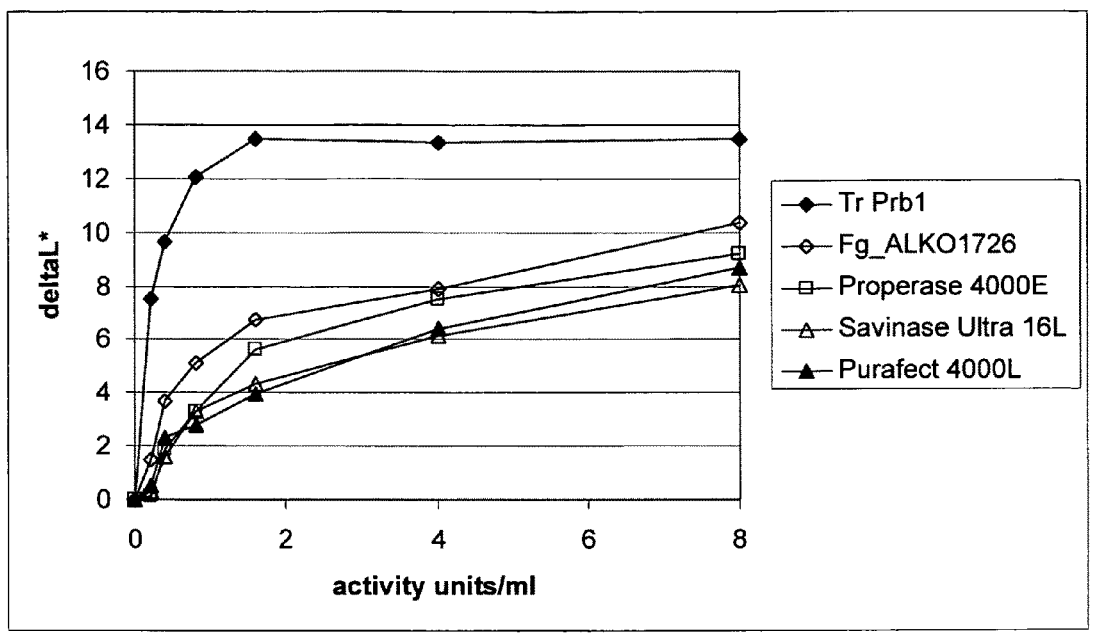
Figure 9A:
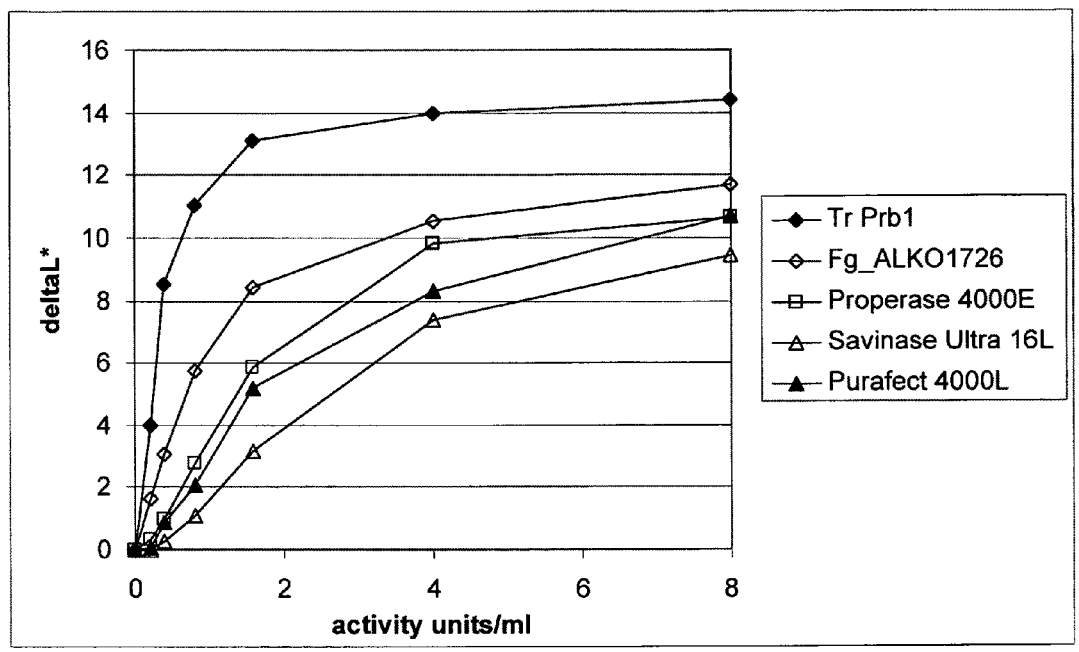
FIG. 9A-E shows the performance of recombinant proteins Tr Prb1 and Fg_ALKO1729 with blood/milk/ink stain (Art 117, EMPA) with Liquid Base detergent for coloured fabrics (Table 2) at different detergent concentrations at 30° C. and with detergent concentration 3.3 g/l at 10° C. and 20° C. Commercial preparations Properase® 4000E, Purafect® 4000L and Savinase® Ultra 16L were used for comparison.
Figure 9B:
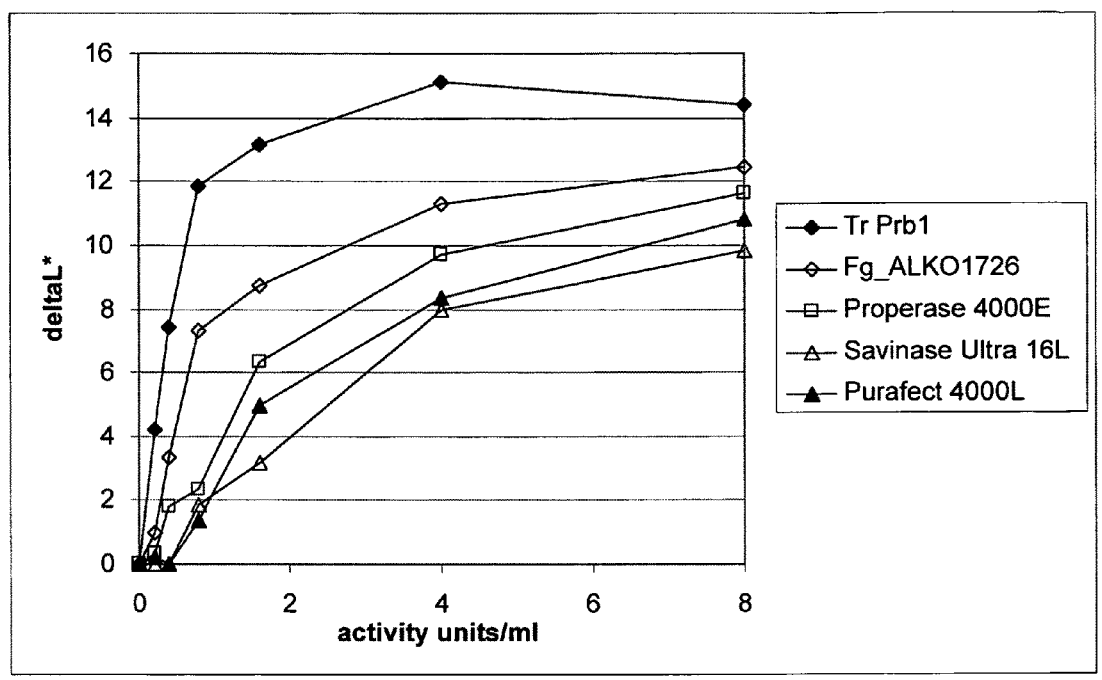
Figure 9C:
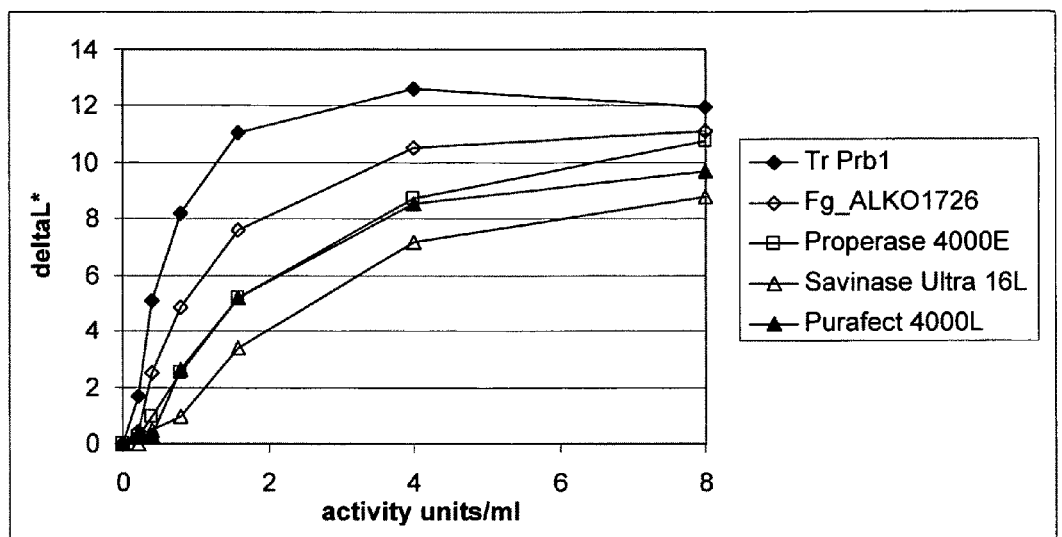
Figure 9D:
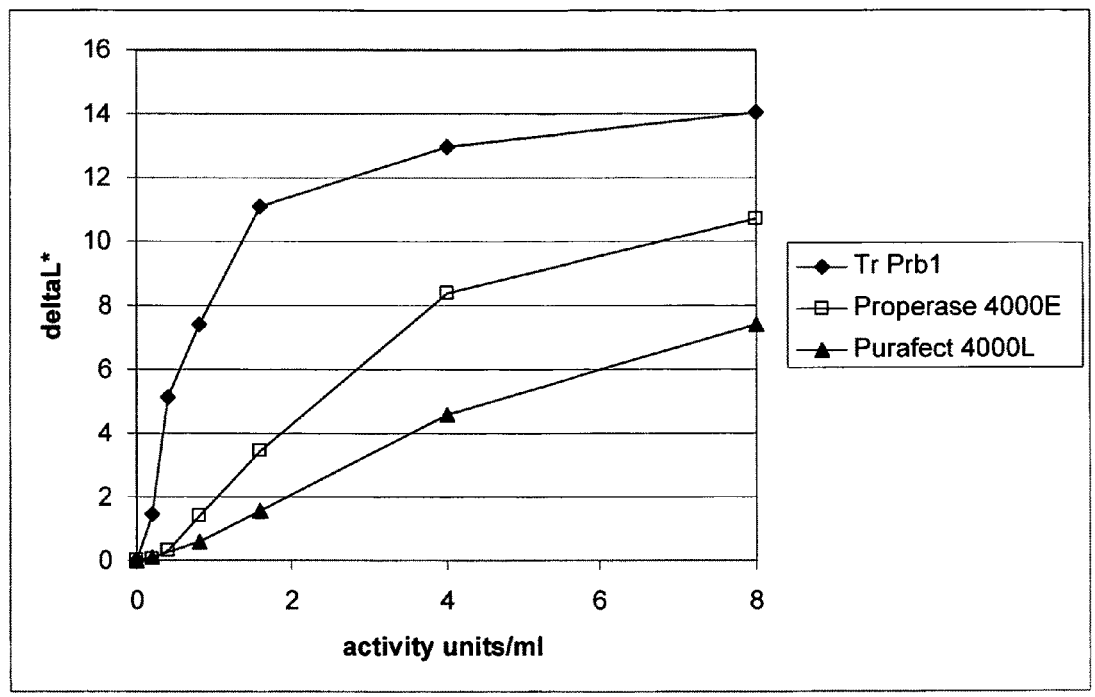
Figure 9E:
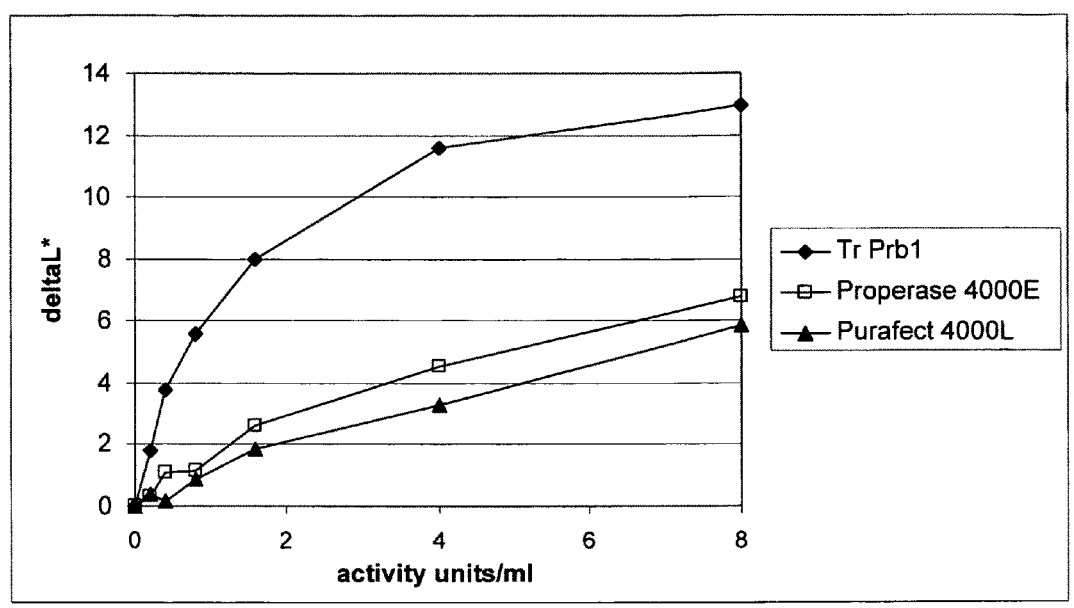

Results obtained with Ariel Sensitive and Erisan at 30° C. are shown in FIGS. 8A and B. Results obtained with Base detergent for colored fabrics using different detergent concentrations at 30° C. are shown in FIG. 9A-C and results obtained with detergent concentration 3.3 g/l at 10° C. and 20° C. are shown in FIGS. 9D and E. The efficiency of Tr Prb1 on blood/milk/ink stain was considerably higher at 30° C. compared to commercial preparations Savinase® Ultra 16L, Purafect® 4000L and Properase® 4000E with all detergents and at all detergent concentrations, when same amount of activity was dosed. The performance of Tr Prb1 compared to Purafect® 4000L and Properase® 4000E was remarkably higher especially at the lowest temperatures (10° C. and 20° C.). Results of these tests indicate that Tr Prb1 protease has excellent performance with liquid detergents at low washing temperatures. Also Fg_ALKO1726 preparation was at least as good as the above mentioned commercial protease preparations at 30° C.

EXAMPLE 6

Performance of Recombinant Protein Tr Prb1 and Fg_ALKO1726 with Detergent Powder at 40-50° C. and pH 10

Recombinant protein Tr Prb1 and Fg_ALKO1726 preparations produced in *Trichoderma* (as described in Example 2) were tested for their ability to remove blood/milk/ink standard stain in the presence of phosphate containing reference detergent at 40° C. and 50° C. (pH appr. 10). Standard stain Art.117 (blood/milk/ink, polyester+cotton, EMPA) was used as test material. Commercial proteases Purafect® 4000L, Properase® 4000E and treatment without enzyme (control) were used for comparison. Each enzyme was dosed 0, 0.2, 0.4, 0.8, 1.6, 4, and 8 activity units (μmol tyrosine/min) per ml wash liquor. Activity was measured as described in Example 4.

An amount of 3.3 g of phosphate containing ECE reference detergent 77 without optical brightener (Art. 601, EMPA) was dissolved in 1 liter of tap water (dH≦4), mixed well with magnetic stirrer and tempered to 40° C./50° C. Stain fabric was cut into pieces like described in Example 4. Swatches were placed in wells of microtiter plates (Nunc 150200) and 1.5 ml washing liquor containing detergent and enzyme dilution in water (below 60 μl) was added on top of the fabric. The plates with samples were incubated in a horizontal shaker at 40° C./50° C. for 60 min with 125 rpm. After that the swatches were carefully rinsed under running water (appr. 45° C.) and dried overnight at indoor air, on a grid, protected against daylight.

The color of the swatches after treatment was measured with Minolta CM 2500 spectrophotometer using L*a*b* color space coordinates stain removal effect calculated as ΔL* as described in Example 4. For treatment without enzyme (enzyme blank), the detergent solution was used as washing liquor.

The results (FIGS. 10A and B) showed that protease Tr Prb1 and Fg_ALKO1726 are also suitable with powder detergents at very alkaline conditions.

EXAMPLE 7

Evaluation of the Performance of the Recombinant Protein Tr Prb1 in Liquid Laundry Detergent 30° C. in Full Scale Trials The performance of recombinant protein Tr Prb1 preparation produced in *Trichoderma* (as described in Example 2) was tested in liquid detergent in full scale in a washing machine at 30° C. using short washing time (15 min) and compared to commercial protease preparations Purafect® 4000L and treatment with detergent without enzyme. Liquid base detergent for colored fabrics, as described in Example 8, and 9 different protease sensitive tracers (Table 5) were used. Tracers were from EMPA Testmaterialen AG, Swizerland CFT (Center For Testmaterials BV, The Netherlands). Stain swatches appr. 10 cm×10 cm were stitched to pillow cases. The process parameters and conditions are described in Table 6. Enzyme dosages used in the trials were calculated both as enzyme activities (appr. 0-14 activity units per ml of washing liquor) and as amount of protein (appr. 0-4 mg per litre of washing liquor). Purafect® 4000L was dosed 0.5, 0.75 and 1% of the detergent weight. Protease activity was measured as described in Example 4. The amount of protein from the enzyme preparations was determined by Bio-Rad protein assay (Bio-Rad Laboratories, Hercules, Calif.) using bovine gammaglobulin (Bio-Rad) as standard.

Similar washing procedure than No. 5A described on the European standard EN ISO 6330:2000 was used, except the temperature was set to 30° C. instead of 40° C. The protease sensitive swatches were dried overnight at indoor air, on a grid, protected against daylight and the filler material was tumble dried

TABLE 5

Protease sensitive tracers used in test

| Swatch | Amount/wash | Substrate |
| --- | --- | --- |
| EMPA Art.117 (Serial No. 10-07) | 2 | Blood/milk/ink, PE + CO |
| EMPA Art.116 (Serial No. 18-16) | 2 | Blood/milk/ink, CO |
| EMPA Art.112 (Serial No. 31-06) | 2 | Cocoa |
| CFT/C-03-030 | 1 | Chocolate milk/pigment |
| CFT/C-05-059b | 1 | Bood/milk/ink/CO |
| CFT/PC-05-014 | 1 | Blood/Milk/Ink/PE-CO |
| CFT/CS-08-069 | 1 | Grass/Cotton |
| CFT/C-10-186b | 1 | Groundnut oil/milk |
| CFT/CS-38-010 | 1 | Egg Yolk/Pigment |

TABLE 6

Process parameters and conditions

| | |
| --- | --- |
| Machine | Wascator FOM71 CSL (Electrolux) |
| Program | 30° C., 15 min (ISO 6330:200, 5A, temperature modified) |
| Hardness of water | ≦4 with appr. 20 kg intake |
| Ballast Load | 2.0 kg white bed-sheets, pillowcases, terry towels |
| Detergent dosage | 50 g/machine load (appr. 2.5 g/l) |

The stain removal effect was evaluated by measuring the color as reflectance values with Minolta CM 2500 spectrophotometer using L*a*b* color space coordinates (illuminant) D65/2°). The color from both sides of the swatches was measured after the treatment. Each value was the average of approximately 12 measurements (6 from each side). With EMPA's stains the values were the average of measurements of two swatches. Fading of the stain indicating of the protease performance (stain removal efficiency) was calculated as ΔL*, which means lightness value L* of enzyme treated fabric minus lightness value L* of fabric treated with detergent only. The color of the stain swatches was measured also before the treatment, but the values were not included in calculations since the swatches were homogeneous (standard deviation of L* values <0.2 units with all stains).

The results of are shown in FIGS. 11A-I. The performance of Tr Prb1 at low temperature and short cycle wash (15 min) was considerably higher with all tested stains compared to commercial protease preparations Purafect® 4000L, when proteases were dosed as amount of activity. Also if dosing is calculated as amount of added protein (FIGS. 12A and B), the stain removal efficiency of Tr Prb1 was similar or slightly better than with Purafect® 4000L, even though the measurement of total protein was not favorable to Tr Prb1 preparation that originated from an unoptimised fermentation.

Similar or slightly better stain removal efficiency compared to Purafect® 4000L was obtained with Tr Prb1 also using longer washing time (60 min) when enzyme dosage was 1.9 mg protein per liter of washing liquor, corresponding to activity units per ml for appr. 2 units for Tr Prb1 and appr. 14 units for Purafect® 4000L

EXAMPLE 8

Protease Activity Assay II

Protease activity was assayed by the casein Folin-Ciocalteau method using casein as a substrate. Rate of casein degradation by a protease was measured by spectrophotometrical monitoring of the release of acid-soluble fragments as a function of time. Casein substrate used in the assay was prepared as follows: 6 g of Casein Hammerstein Grade MP Biomedicals, LLC (101289) was dissolved in 500 ml of 30 mM Tris, 2.0 mM $CaCl_2$, 0.7 mM $MgCl_2$, 2.5 mM $NaHCO_3$. The pH of the substrate solution was adjusted to 8.5. The enzyme reactions were stopped using 0.11 M TCA solution. The Folin reagent used in the assay was prepared by diluting 25 ml of 2 N Folin-Ciocalteu's phenol reagent (SIGMA, F 9252) to 100 ml by distilled water. The reaction was started by first incubating 2.5 ml of substrate solution for 5 min at 50° C. after which 0.5 ml of enzyme solution was added and reaction was conducted for 15 min (for determination of the temperature and pH profiles) or 30 mM. After 15 min or 30 min reaction 2.5 ml of reaction stop solution was added, the contents were mixed and allowed to stand for 30 minutes at room temperature. Tubes were centrifuged 4000 rpm for 10 minutes (Hettich Rotanta 460). One ml of clear supernatant was mixed with 2.5 ml 0.5 M $Na_2CO_3$ and 0.5 ml diluted Folin reagent. After waiting for at least 5 min (color development) the absorbance of the mixture (color) was measured at 660 nm against an enzyme blank. The enzyme blank was prepared as follows: 0.5 ml enzyme solution was mixed with 2.5 ml stopping solution and 2.5 ml substrate, and the mixture was incubated for 15 min or 30 mM at 50° C. One unit of enzyme activity was defined as the enzyme quantity that liberates the acid soluble protein hydrolysis product corresponding to 1 μg of tyrosine per ml (or g) of the reaction mixture per min.

REFERENCES

Altschul S F, W Gish, W Miller, E W Myers and D J Lipman. 1990. Basic local alignment search tool. J. Mol. Biol. 215: 403-410.

AMFEP, 2007. Association of Manufacturers and Formulators of Enzyme products, List of commercial enzymes at http://www.amfep.org/list.html (updated 30 Nov. 2007).

Antal Z, L Manczinger, G Szakacs, R P Tengerdy and L Ferenczy. 2000. Colony growth, in vitro antagonism and secretion of extracellular enzymes in cold-tolerant strains of Trichoderma species. Mycol. Res. 104:545-549.

Anwar A and M Saleemuddin. 1998. Alkaline proteases: A review. Bioresource Technology 64:175-183.

Bolton E T and B J McCarthy. 1962. A general method for the isolation of RNA complementary to DNA. Proc. Nat. Acad. Sci. USA 48:1390-1397.

Chen Y-J, and M Inouye, 2008. The intramolecular chaperone-mediated protein folding. Curr. Opin. Struct. Biol. 18: 765-770.

Cherry J R. and A L Fidantsef. 2003. Directed evolution of industrial enzymes: an update. Curr. Opin. Biotechnol. 14: 438-443.

Dienes D, J Börjesson, P Hägglund, F Tjerneld, G Liden, K Réczey and H Ståbrand. 2007. Identification of a trypsin-like serine protease from Trichoderma reesei QM9414. Enzyme and Microb. Technol. 40:1087-1094.

Edman P and G Begg. 1967. A protein sequenator. Eur. J. Biochem. 1:80-91.

Gasteiger E, A Gattiker, C Hoogland, I Ivanyi, R D Appel and A Bairoch. 2003. ExPASy: the proteomics server for in-depth protein knowledge and analysis. Nucleic Acids Res. 31:3784-3788.

Geremia R A, G H Goldman, W Ardiles, S B Vila, M Van Montagu and A Herrera-Estrella. 1993. Molecular characterization of the proteinase-encoding gene, prb1, related to mycoparasitism by Trichoderma harzianum. Mol. Microbiol. 8(3):603-613.

Gupta R, Q K Beg, S Khan and B Chauhan. 2002. An overview on fermentation, downstream processing and properties of microbial alkaline protease. Appl. Microbiol. Biotechnol. 60: 381-395.

Gurr S J, S E Uncles and J R Kinghom. 1987. The structure and organization of nuclear genes in filamentous fungi, pp. 93-139. In (J R Kinghorn, ed.) Gene Structure in Eukaryotic Microbes. IRL Press, Oxford.

Joutsjoki V V, T K Torkkeli, and K M H Nevalainen. 1993. Transformation of Trichoderma reesei with the Hormoconis resinae glucoamylase P (gamP) gene: production of a heterologous glucoamylase by Trichoderma reesei. Curr. Genet. 24:223-228.

Kalisz H M. 1988. Microbial proteinases. Adv. Biochem. Eng. Biotechnol. 36:1-65.

Karhunen T, A Mäntylä, K M H Nevalainen and P L Suominen. 1993. High frequency one-step gene replacement in Trichoderma reesei. I. Endoglucanase I overproduction. Mol. Gen. Genet. 241:515-522.

Kredics L, Z Antal, A Szekeres, L Hatvani, L Manczinger, CS Vágwölgyi and E Nagy. 2005. Extracellular proteases of Trichoderma species. Acta Microbiol. et Immunol. Hungarica 52:169-184.

Laemmli U K. 1970. Cleavage of structural proteins during the assembly of the head of bacteriophage T4. Nature 227: 680-685.

Malardier L, M J Daboussi, J Julien, F Roussel, C Scazzocchio and Y Brygoo. 1989. Cloning of the nitrate reductase gene (niaD) of Aspergillus nidulans and its use for transformation of Fusarium oxysporum. Gene 78:147-156.

Manonmani H K and R Joseph. 1993. Preparation and properties of insolubilized proteinase of Trichoderma koningii. Process Biochem. 34:325-329.

Matrinez D, R M Berka, B Henrissat, M Saloheimo, M Arvas, S E Bakers, J Chapman, O Chertkov, P M Coutinho, D Cullen, E G J Danchin, I V Grigoriev, P Harris, M Jackson, C P Kubicek, C S Han, I Ho, L F Larrondo, A L de Leon, J K Magnuson, S Merino, M Misra, B Nelson, N Putman, B Robbertse, A A Salamov, M Schmoll, A Terry, N Thayer, A Westerholm-Parvinen, C L Schoch, J Yao, R Barabote, M A Nelson, C Detter, D Bruce, C R Kuske, G Xie, P Richardson, D S Rokhsar, S M Lucas, E M Rubin, N Dunn-Coleman, M Ward and T S Brettin. 2008. Genome sequencing and analysis of the biomass-degrading fungus *Trichoderma reesei* (syn. *Hypocrea jecorina*). Nature Biotechnol. 26:553-560.

Maurer K-H. 2004. Detergent proteases. Curr. Opin. Biotechnol. 15: 330-334.

Nielsen H, J Engelbrecht, S Brunak and G von Heijne. 1997. Identification of prokaryotic and eukaryotic signal peptides and prediction of their cleavage sites. Protein Engineering 10:1-6.

Nielsen H and A Krogh. 1998. Prediction of signal peptides and signal anchors by a hidden Markov model. In: Proceedings of the Sixth International Conference on Intelligent Systems for Molecular Biology (ISMB 6), AAAI Press, Menlo Park, Calif., pp. 122-130.

Paloheimo M, A Mäntylä, J Kallio and P Suominen. 2003. High-yield production of a bacterial xylanase in the filamentous fungus *Trichoderma reesei* requires a carrier polypeptide with an intact domain structure. Appl. Env. Microbiol. 69:7073-7082.

Penttilä M, H Nevalainen, M Rättoö, E Salminen and J Knowles. 1987. A versatile transformation system for the cellulolytic filamentous fungus *Trichoderma reesei*. Gene 61:155-164.

Pozo M J, J-M Baek, J M Garcia and C M Kenerley. 2004. Functional analysis of tvsp1, a serine protease-encoding gene in the biocontrol agent *Trichoderma virens*. Fungal Genet. Biol. 41:336-348.

Raeder U and P Broda. 1985. Rapid preparation of DNA from filamentous fungi. Lett. Appl. Microbiol. 1:17-20.

Rao M B, A M Tanksale, M S Ghatge and V V Deshpande. 1998. Molecular and biotechnological aspects of microbial proteases. Microbiol. Mol. Biol. Rev. 62:597-635.

Sambrook J and D W Russell. 2001. Molecular cloning, a laboratory manual. Cold Spring Harbor Laboratory, New York, US.

Shimogaki H, K Takenchi, T. Nishino, M. Ohdera, T. Kudo, K. Ohba, M V Iwama and M Irie. 1991. Purification and properties of a novel surface active agent and alkaline-resistant protease from *Bacillus* sp. Y. Agric. Biol. Chem. 55:2251-2258.

Steyaert J M, A Stewart and H J Ridgway. 2004. Co-expression of two genes, a chitinase (chit42) and proteinase (prb1), implicated in mycoparasitism by *Trichoderma hamatum*. Mycologia 96:1245-1252.

Suarez M B, Vizcaino J A, Lobell A and Monte E. 2007. Characterization of genes encoding novel peptidases in the biocontrol *Trichoderma harzianum* CECT 2413 using the TrichoEST functional genomics approach. Curr. Genet. 51:331-342.

The invention claimed is:

1. A recombinant serine protease enzyme, comprising a polypeptide that has an amino acid sequence having at least 94% sequence identity over the full-length amino acid sequence set forth in SEQ ID NO: 10, wherein the sequence identity is determined using ClustalW alignment using matrix: BLOSUM, Gap Open: 10, and Gap Extension: 0.5; and wherein the polypeptide has serine protease activity.

2. The recombinant serine protease enzyme of claim 1, wherein said enzyme has use as a detergent additive having lightening activity.

3. The recombinant serine protease enzyme of claim 1, wherein said enzyme is obtained from a filamentous fungus *Trichoderma*.

4. The recombinant serine protease enzyme of claim 1, wherein said enzyme comprises the amino acid sequence set forth in SEQ ID NO: 10.

5. The recombinant serine protease enzyme of claim 1, wherein a mature form of said enzyme has a molecular mass between 20 and 35 kDa.

6. The recombinant serine protease enzyme of claim 1, wherein said enzyme is encoded by an isolated nucleic acid molecule, which encodes a polypeptide comprising the amino acid sequence set forth in SEQ ID NO:10.

7. The recombinant serine protease enzyme of claim 1, wherein said enzyme is encoded by an isolated nucleic acid molecule comprising the nucleotide sequence set forth in SEQ ID NO: 9.

8. The recombinant serine protease enzyme of claim 1, wherein said enzyme is encoded by the polynucleotide sequence set forth in SEQ ID NO: 5 included in plasmid pALK2650 contained in *Escherichia coli* RF8052 which is deposited under accession number DSM 22635.

9. The recombinant serine protease enzyme of claim 1, wherein said recombinant serine protease enzyme is produced from a recombinant expression vector comprising a nucleic acid molecule encoding the serine protease according to claim 1 operably linked to regulatory sequences capable of directing the expression of the serine protease enzyme encoding gene in a suitable host.

10. The recombinant serine protease enzyme of claim 1, wherein said enzyme is produced in a heterologous host.

11. The recombinant serine protease enzyme of claim 1, wherein said enzyme is produced in a microbial host.

12. The recombinant serine protease enzyme of claim 1, wherein said enzyme is produced in a host of the genus *Trichoderma*, *Aspergillus*, *Fusarium*, *Humicola*, *Chrysosporium*, *Neurospora*, *Rhizopus*, *Penicillium* or *Mortiriella*.

13. The recombinant serine protease enzyme of claim 12, wherein said enzyme is produced in *Trichoderma* or *Aspergillus*.

14. The recombinant serine protease enzyme of claim 13, wherein said enzyme is produced in *T. reesei*.

15. A recombinant polypeptide having serine protease activity, wherein the polypeptide is encoded by a nucleic acid sequence selected from the group consisting of:
    (a) a nucleic acid molecule encoding a polypeptide having serine protease activity and comprising the amino acid sequence set forth in SEQ ID NO:10;
    (b) a nucleic acid molecule comprising the polynucleotide sequence set forth in SEQ ID NO:9;
    (c) a nucleic acid molecule comprising the coding sequence of the polynucleotide sequence set forth in SEQ ID NO:5 contained in DSM 22635; and
    (d) a nucleic acid molecule the polynucleotide sequence of which differs from the polynucleotide sequence of a nucleic acid molecule of (a) to (c) due to the degeneracy of the genetic code,
    wherein the polypeptide is obtained by a process comprising the steps of:
    (i) culturing a host cell comprising a recombinant expression vector comprising the nucleic acid sequence operably linked to regulatory sequences that direct expression of the nucleic acid sequence in the host cell; and
    (ii) recovering the polypeptide.

16. A recombinant enzyme preparation obtained by a process comprising the steps of:
    (i) culturing in a culture medium a host cell comprising a recombinant expression vector comprising a nucleotide sequence selected from the group consisting of:
    (a) a nucleic acid molecule encoding a polypeptide having serine protease activity and comprising the amino acid sequence set forth in SEQ ID NO:10;
    (b) a nucleic acid molecule comprising the polynucleotide sequence set forth in SEQ ID NO:9;
    (c) a nucleic acid molecule comprising the coding sequence of the polynucleotide sequence set forth in SEQ ID NO:5 contained in DSM 22635; and
    (d) a nucleic acid molecule the polynucleotide sequence of which differs from the polynucleotide sequence of a nucleic acid molecule of (a) to (c) due to the degeneracy of the genetic code, wherein the nucleotide sequence is operably linked to regulatory sequences that direct expression of the polypeptide in a suitable host, and (ii) either recovering the polypeptide from the cells or, if the polypeptide is secreted into the culture medium, separating the cells from the culture medium and recovering the polypeptide from the culture medium.

17. An enzyme preparation, which comprises the recombinant serine protease enzyme according to claim 1.

18. The enzyme preparation of claim 17, wherein said preparation further comprises other enzymes selected from the group consisting of protease, amylase, cellulase, lipase, xylanase, mannanase, cutinase, pectinase and oxidase with or without a mediator of the oxidase.

19. The enzyme preparation of claim 17, wherein said preparation further comprises an additive selected from the group consisting of stabilizers, buffers, surfactants, builders, bleaching agents, mediators of an oxidase, anti-corrosion agents, antiredeposition agents, caustics, abrasives, optical brighteners, dyes, pigments, and preservatives.

20. The enzyme preparation of claim 17, wherein said enzyme preparation is in the form of liquid, powder or granulate.

21. A method for degrading or removing proteinaceous materials from a solid, water-insoluble carrier comprising treating the solid, water-insoluble carrier with a composition comprising the recombinant serine protease of claim 1.

22. The method of claim 21, wherein the composition comprises a detergent.

23. The method of claim 21, wherein the composition comprises a detergent liquid.

24. The method of claim 21, wherein the composition comprises a detergent powder.

25. The recombinant serine protease of claim 1, wherein said recombinant serine protease degrades or removes proteinaceous materials from a solid, water-insoluble carrier at 10° C. to 60° C.

26. The recombinant serine protease of claim 25, wherein said solid, water-insoluble carrier is fabric or glass.

27. The method of claim 21, wherein the solid, water-insoluble carrier is fabric.

28. The method of claim 21, wherein the solid, water-insoluble carrier is glass.

* * * * *

UNITED STATES PATENT AND TRADEMARK OFFICE
CERTIFICATE OF CORRECTION

PATENT NO. : 8,362,222 B2  
APPLICATION NO. : 12/803456  
DATED : January 29, 2013  
INVENTOR(S) : Leena Valtakari et al.

Page 1 of 3

It is certified that error appears in the above-identified patent and that said Letters Patent is hereby corrected as shown below:

On the Title Page:

On page 2, Column 1 (Other Publications), line 2, delete "*Thricoderma*" and insert -- *Trichoderma* --, On page 2, Column 1 (Other Publications), line 4, delete "Full-Serin" and insert -- Full-Serine --, On page 2, Column 1 (Other Publications), line 50, delete "(prbl)" and insert -- (prb1) --, On page 2, Column 2 (Other Publications), line 40, delete "Interleukin-1 α" and insert -- Interleukin-1α --, On page 3, Column 2 (Other Publications), line 10, delete "lacasse"," and insert -- laccase," --, In the Drawings:

On Sheet 28 of 33 (FIG. 11F), delete "CFT/C-03-" and insert -- CFT/C-03-030 --,

In the Specifications:

In Column 1, line 7, delete "F120095779" and insert -- FI20095779 --,

In Column 1, line 51, delete "Del.)." and insert -- DE). --,

In Column 4, line 38, delete "*Mortiriella.*" and insert -- *Mortierella.* --,

In Column 5, line 1, delete "*Mortiriella.*" and insert -- *Mortierella.* --,

In Column 6, line 3, before "nucleotides" delete "the",

Signed and Sealed this  
Sixteenth Day of April, 2013

Teresa Stanek Rea  
*Acting Director of the United States Patent and Trademark Office*

CERTIFICATE OF CORRECTION (continued)
U.S. Pat. No. 8,362,222 B2

In Column 6, line 26, delete "mM" and insert -- min --,

In Column 9, line 32, delete "*amyloliquifaciens*," and insert -- *amyloliquefaciens*, --, In Column 11, line 8, delete "expasy" and insert -- (expasy --, In Column 15, line 24, delete "*Mortiriella*," and insert -- *Mortierella*, --, In Column 16, line 4, delete "jai" and insert -- jgi --, In Column 17, line 66, delete "*sublitis*" and insert -- *subtilis* --, In Column 18, line 43, delete "*Mortiriella*," and insert -- *Mortierella*, --, In Column 18, line 54, delete "*Mortiriella alpinis*," and insert -- *Mortierella alpina*, --, In Column 24, line 8, delete "preperation" and insert -- preparation --, In Column 24, line 46, delete "XM.sub.-383491," and insert -- XM_383491, --, In Column 24, lines 48-49, delete "XM.sub.-383491" and insert -- XM_383491 --, In Column 25, line 31, delete "mM" and insert -- min --, In Column 26, line 34, delete "serin" and insert -- serine --, In Column 27, line 24, delete "Bioreator" and insert -- Bioreactor --, In Column 27, lines 51-52, delete "Folin-Ciocalteau" and insert -- Folin-Ciocalteu --, In Column 29, lines 2-3, delete "Swizerland)" and insert -- Switzerland) --, In Column 29, lines 26-27, delete "(illuminant)" and insert -- (illuminant --, In Column 30, line 53, delete "concentration.or" and insert -- concentration or --, In Column 32, line 7, delete "Swizerland" and insert -- Switzerland --, In Column 32, line 26, delete "dried" and insert -- dried. --, In Column 32, line 37, delete "Bood" and insert -- Blood --, In Column 32, line 46, delete "CSL" and insert -- CLS --,

CERTIFICATE OF CORRECTION (continued)
U.S. Pat. No. 8,362,222 B2

In Column 32, lines 55-56, delete "(illuminant)" and insert -- (illuminant --,

In Column 33, line 16, delete "4000L" and insert -- 4000L. --,

In Column 33, lines 22-23, delete "Folin-Ciocalteau" and insert -- Folin-Ciocalteu --, In Column 33, line 38, delete "mM." and insert -- min. --, In Column 33, line 49, delete "mM" and insert -- min --, In Column 34, line 29, delete "Kinghom." and insert -- Kinghorn. --, In Column 35, line 22, delete "Rättoö," and insert -- Rättö, --, In the Claims:

In Column 58, line 21, in claim 12, delete "*Mortiriella.*" and insert -- *Mortierella.* --.

```
                    SEQUENCE LISTING

<160> NUMBER OF SEQ ID NOS: 16

<210> SEQ ID NO 1
<211> LENGTH: 45
<212> TYPE: DNA
<213> ORGANISM: Artificial Sequence
<220> FEATURE:
<223> OTHER INFORMATION: Sequence of the 5'-PCR primer PRO213 used for
      cloning the Trichoderma reesei QM6a prb1 gene

<400> SEQUENCE: 1
tccccgcgga ctgcgcatca tggccagcct tcgtcgcctt gccct           45

<210> SEQ ID NO 2
<211> LENGTH: 35
<212> TYPE: DNA
<213> ORGANISM: Artificial Sequence
<220> FEATURE:
<223> OTHER INFORMATION: Sequence of the 3'-PCR primer PRO214 used for
      cloning the Trichoderma reesei QM6a prb1 gene

<400> SEQUENCE: 2
cgcggatcct taagcactgt tcccgttgaa gatga                       35

<210> SEQ ID NO 3
<211> LENGTH: 45
<212> TYPE: DNA
<213> ORGANISM: Artificial Sequence
<220> FEATURE:
<223> OTHER INFORMATION: Sequence of the 5'-PCR primer PRO245 used for
      cloning the Fusarium graminearum ALKO1726 protease

<400> SEQUENCE: 3
acccgcggac tgcgcatcat gaccagcttc cgccgtcttg ctctc            45

<210> SEQ ID NO 4
<211> LENGTH: 33
<212> TYPE: DNA
<213> ORGANISM: Artificial Sequence
```

```
<220> FEATURE:
<223> OTHER INFORMATION: Sequence of the 3'-PCR primer PRO246 used for
      cloning the Fusarium graminearum ALKO1726 protease

<400> SEQUENCE: 4
cgggatcctt aagtagaggc accgttgaag gcg                                  33

<210> SEQ ID NO 5
<211> LENGTH: 1371
<212> TYPE: DNA
<213> ORGANISM: Trichoderma reesei
<220> FEATURE:
<221> NAME/KEY: misc_feature
<223> OTHER INFORMATION: The nucleotide sequence of the full-length
      Trichoderma reesei QM6a protease gene prb1 (Tr prb1) encoding the
      Prb1 protease (ID 121495).

<400> SEQUENCE: 5
atggccagcc ttcgtcgcct tgccctctat ctcggagccc tgctcccggc tgttctggcc        60
gctcctgctg tcaattacaa gctgcctgaa gctgttccca acaagttcat tgtcactctc       120
aaagatggtg cctctgttga tacagactct caccttacat gggtgaaaga ccttcacagg       180
cgctcactcg gcaagcgcag cactgctggt gttgagaaga cgtacaacat cgacagctgg       240
aatgcctatg ctggcgagtt cgatgaagaa accgttaagc agatcaaggc gaatcccgac       300
gtaagtattt gccctactgt tggacgagat gccaatgttc cattgcgaaa ttctaatgag       360
cataccaggt tgcttccgta gagccagact acatcatgtg ttgtctgac attgtggaag        420 acaagcgtgc tttgaccact cagactggcg ccccctgggg actcggcact gtctcccacc       480
gcacacccgg ctcaactagc tacatctatg acacttcggc tggtagcgga acattcgcct       540
atgttgttga ctctggaatc aacattgctc caagcaatt cggcggacgt gccagcctcg        600
gctacaacgc cgctggtgga gatcatgtcg acactctcgg ccacggcacg cacgtttccg       660
gaactatcgg tggctctacc tatggtgttg ctaagcaggt aagctgcttc attatacttc       720
ttcctttgca gtgcgggcct tgagcacgcc gggctgactc tgtaacgaaa ggccagctta       780
atctccgtca aggtcttcca gggcaacagc gccagcacct cggtcatcct tgacggctat       840
aattgggccg tgaacgacat tgtctcccgc aaccgcgcca gcaagtctgc catcaacatg       900
tctctcggtg gccggcctc ttccacctgg gctacggcga tcaatgcagc ctttaacaag        960
ggcgtcctga cgatcgtggc cgccggcaat ggtgacgctc ttggaaaccc tcagcctgtc      1020
tccagtactt ctccagccaa tgtgcccaac gccatcaccg tcgcagccct tgacattaac      1080
tggcgcaccg cttccttcac caattatggt gctggcgttg acgtcttcgc tcctggtgtc      1140
aacatcctgt cttcgtggat cggctctaac actgccacaa acacgattag cggcaccctcc    1200 atggccactc ctcacgttgt cggcctcgct ctttacctgc aggctcttga gggccttagc      1260
accccgactg ctgtaaccaa ccgcatcaag gccttggcta ctactggacg cgtcaccggc      1320
agtctgaatg gcagccccaa cactctcatc ttcaacggga acagtgctta a               1371

<210> SEQ ID NO 6
<211> LENGTH: 409
<212> TYPE: PRT
<213> ORGANISM: Trichoderma reesei
<220> FEATURE:
<221> NAME/KEY: MISC_FEATURE
<223> OTHER INFORMATION: The deduced amino acid sequence of the
      full-length Trichoderma reesei QM6a protease Prb1 (Tr_Prb1)
      including amino acids from Met1 to Ala409.

<400> SEQUENCE: 6
```

```
Met Ala Ser Leu Arg Arg Leu Ala Leu Tyr Leu Gly Ala Leu Leu Pro
1               5                   10                  15
Ala Val Leu Ala Ala Pro Ala Val Asn Tyr Lys Leu Pro Glu Ala Val
            20                  25                  30
Pro Asn Lys Phe Ile Val Thr Leu Lys Asp Gly Ala Ser Val Asp Thr
        35                  40                  45
Asp Ser His Leu Thr Trp Val Lys Asp Leu His Arg Arg Ser Leu Gly
    50                  55                  60
Lys Arg Ser Thr Ala Gly Val Glu Lys Thr Tyr Asn Ile Asp Ser Trp
65                  70                  75                  80
Asn Ala Tyr Ala Gly Glu Phe Asp Glu Thr Val Lys Gln Ile Lys
                85                  90                  95
Ala Asn Pro Asp Val Ala Ser Val Glu Pro Asp Tyr Ile Met Trp Leu
            100                 105                 110
Ser Asp Ile Val Glu Asp Lys Arg Ala Leu Thr Thr Gln Thr Gly Ala
        115                 120                 125
Pro Trp Gly Leu Gly Thr Val Ser His Arg Thr Pro Gly Ser Thr Ser
    130                 135                 140
Tyr Ile Tyr Asp Thr Ser Ala Gly Ser Gly Thr Phe Ala Tyr Val Val
145                 150                 155                 160
Asp Ser Gly Ile Asn Ile Ala His Gln Gln Phe Gly Arg Ala Ser
                165                 170                 175
Leu Gly Tyr Asn Ala Ala Gly Gly Asp His Val Asp Thr Leu Gly His
            180                 185                 190
Gly Thr His Val Ser Gly Thr Ile Gly Gly Ser Thr Tyr Gly Val Ala
        195                 200                 205
Lys Gln Ala Ser Leu Ile Ser Val Lys Val Phe Gln Gly Asn Ser Ala
    210                 215                 220
Ser Thr Ser Val Ile Leu Asp Gly Tyr Asn Trp Ala Val Asn Asp Ile
225                 230                 235                 240
Val Ser Arg Asn Arg Ala Ser Lys Ser Ala Ile Asn Met Ser Leu Gly
                245                 250                 255
Gly Pro Ala Ser Ser Thr Trp Ala Thr Ala Ile Asn Ala Ala Phe Asn
            260                 265                 270
Lys Gly Val Leu Thr Ile Val Ala Ala Gly Asn Gly Asp Ala Leu Gly
        275                 280                 285
Asn Pro Gln Pro Val Ser Ser Thr Ser Pro Ala Asn Val Pro Asn Ala
    290                 295                 300
Ile Thr Val Ala Ala Leu Asp Ile Asn Trp Arg Thr Ala Ser Phe Thr
305                 310                 315                 320
Asn Tyr Gly Ala Gly Val Asp Val Phe Ala Pro Gly Val Asn Ile Leu
                325                 330                 335
Ser Ser Trp Ile Gly Ser Asn Thr Ala Thr Asn Thr Ile Ser Gly Thr
            340                 345                 350
Ser Met Ala Thr Pro His Val Val Gly Leu Ala Leu Tyr Leu Gln Ala
        355                 360                 365
Leu Glu Gly Leu Ser Thr Pro Thr Ala Val Thr Asn Arg Ile Lys Ala
    370                 375                 380
Leu Ala Thr Thr Gly Arg Val Thr Gly Ser Leu Asn Gly Ser Pro Asn
385                 390                 395                 400
Thr Leu Ile Phe Asn Gly Asn Ser Ala
                405

<210> SEQ ID NO 7
```

```
<211> LENGTH: 1311
<212> TYPE: DNA
<213> ORGANISM: Trichoderma reesei
<220> FEATURE:
<221> NAME/KEY: misc_feature
<223> OTHER INFORMATION: The nucleotide sequence encoding the amino acid
      sequence of the proenzyme form of Trichoderma reesei Prb1
      protease.

<400> SEQUENCE: 7
```

| | | | | | |
|---|---|---|---|---|---|
| gctcctgctg | tcaattacaa | gctgcctgaa | gctgttccca | acaagttcat | tgtcactctc | 60 |
| aaagatggtg | cctctgttga | tacagactct | caccttacat | gggtgaaaga | ccttcacagg | 120 |
| cgctcactcg | gcaagcgcag | cactgctggt | gttgagaaga | cgtacaacat | cgacagctgg | 180 |
| aatgcctatg | ctggcgagtt | cgatgaagaa | accgttaagc | agatcaaggc | gaatcccgac | 240 |
| gtaagtattt | gccctactgt | tggacgagat | gccaatgttc | cattgcgaaa | ttctaatgag | 300 |
| cataccaggt | tgcttccgta | gagccagact | acatcatgtg | ttgtctgac | attgtggaag | 360 |
| acaagcgtgc | tttgaccact | cagactggcg | cccctgggg | actcggcact | gtctcccacc | 420 |
| gcacacccgg | ctcaactagc | tacatctatg | acacttcggc | tggtagcgga | acattcgcct | 480 |
| atgttgttga | ctctggaatc | aacattgctc | accagcaatt | cggcggacgt | gccagcctcg | 540 |
| gctacaacgc | cgctggtgga | gatcatgtcg | acactctcgg | ccacggcacg | cacgtttccg | 600 |
| gaactatcg | tggctctacc | tatggtgttg | ctaagcaggt | aagctgcttc | attatacttc | 660 |
| ttcctttgca | gtgcgggcct | tgagcacgcc | gggctgactc | tgtaacgaaa | ggccagctta | 720 |
| atctccgtca | aggtcttcca | gggcaacagc | gccagcacct | cggtcatcct | tgacggctat | 780 |
| aattgggccg | tgaacgacat | tgtctcccgc | aaccgcgcca | gcaagtctgc | catcaacatg | 840 |
| tctctcggtg | gccggcctc | ttccacctgg | gctacggcga | tcaatgcagc | ctttaacaag | 900 |
| ggcgtcctga | cgatcgtggc | cgccggcaat | ggtgacgctc | ttggaaaccc | tcagcctgtc | 960 |
| tccagtactt | ctccagccaa | tgtgcccaac | gccatcaccg | tcgcagccct | tgacattaac | 1020 |
| tggcgcaccg | cttccttcac | caattatggt | gctggcgttg | acgtcttcgc | tcctggtgtc | 1080 |
| aacatcctgt | cttcgtggat | cggctctaac | actgccacaa | acacgattag | cggcaccctcc | 1140 |
| atggccactc | ctcacgttgt | cggcctcgct | ctttacctgc | aggctcttga | gggccttagc | 1200 |
| accccgactg | ctgtaaccaa | ccgcatcaag | gccttggcta | ctactggacg | cgtcaccggc | 1260 |
| agtctgaatg | gcagccccaa | cactctcatc | ttcaacggga | acagtgctta | a | 1311 |

```
<210> SEQ ID NO 8
<211> LENGTH: 389
<212> TYPE: PRT
<213> ORGANISM: Trichoderma reesei
<220> FEATURE:
<221> NAME/KEY: MISC_FEATURE
<223> OTHER INFORMATION: The amino acid sequence of the proenzyme form
      of Trichoderma reesei Prb1 protease including amino acids Ala21 to
      Ala 409 of the full length protease.

<400> SEQUENCE: 8

Ala Pro Ala Val Asn Tyr Lys Leu Pro Glu Ala Val Pro Asn Lys Phe
1               5                   10                  15

Ile Val Thr Leu Lys Asp Gly Ala Ser Val Asp Thr Asp Ser His Leu
            20                  25                  30

Thr Trp Val Lys Asp Leu His Arg Arg Ser Leu Gly Lys Arg Ser Thr
        35                  40                  45

Ala Gly Val Glu Lys Thr Tyr Asn Ile Asp Ser Trp Asn Ala Tyr Ala
    50                  55                  60
```

Gly Glu Phe Asp Glu Thr Val Lys Gln Ile Lys Ala Asn Pro Asp
 65                  70                  75                  80

Val Ala Ser Val Glu Pro Asp Tyr Ile Met Trp Leu Ser Asp Ile Val
             85                  90                  95

Glu Asp Lys Arg Ala Leu Thr Thr Gln Thr Gly Ala Pro Trp Gly Leu
             100                 105                 110

Gly Thr Val Ser His Arg Thr Pro Gly Ser Thr Ser Tyr Ile Tyr Asp
             115                 120                 125

Thr Ser Ala Gly Ser Gly Thr Phe Ala Tyr Val Val Asp Ser Gly Ile
130                 135                 140

Asn Ile Ala His Gln Gln Phe Gly Gly Arg Ala Ser Leu Gly Tyr Asn
145                 150                 155                 160

Ala Ala Gly Gly Asp His Val Asp Thr Leu Gly His Gly Thr His Val
                 165                 170                 175

Ser Gly Thr Ile Gly Gly Ser Thr Tyr Gly Val Ala Lys Gln Ala Ser
             180                 185                 190

Leu Ile Ser Val Lys Val Phe Gln Gly Asn Ser Ala Ser Thr Ser Val
             195                 200                 205

Ile Leu Asp Gly Tyr Asn Trp Ala Val Asn Asp Ile Val Ser Arg Asn
210                 215                 220

Arg Ala Ser Lys Ser Ala Ile Asn Met Ser Leu Gly Gly Pro Ala Ser
225                 230                 235                 240

Ser Thr Trp Ala Thr Ala Ile Asn Ala Ala Phe Asn Lys Gly Val Leu
                 245                 250                 255

Thr Ile Val Ala Ala Gly Asn Gly Asp Ala Leu Gly Asn Pro Gln Pro
             260                 265                 270

Val Ser Ser Thr Ser Pro Ala Asn Val Pro Asn Ala Ile Thr Val Ala
             275                 280                 285

Ala Leu Asp Ile Asn Trp Arg Thr Ala Ser Phe Thr Asn Tyr Gly Ala
             290                 295                 300

Gly Val Asp Val Phe Ala Pro Gly Val Asn Ile Leu Ser Ser Trp Ile
305                 310                 315                 320

Gly Ser Asn Thr Ala Thr Asn Thr Ile Ser Gly Thr Ser Met Ala Thr
                 325                 330                 335

Pro His Val Val Gly Leu Ala Leu Tyr Leu Gln Ala Leu Glu Gly Leu
             340                 345                 350

Ser Thr Pro Thr Ala Val Thr Asn Arg Ile Lys Ala Leu Ala Thr Thr
             355                 360                 365

Gly Arg Val Thr Gly Ser Leu Asn Gly Ser Pro Asn Thr Leu Ile Phe
370                 375                 380

Asn Gly Asn Ser Ala
385

<210> SEQ ID NO 9
<211> LENGTH: 943
<212> TYPE: DNA
<213> ORGANISM: Trichoderma reesei
<220> FEATURE:
<221> NAME/KEY: misc_feature
<223> OTHER INFORMATION: The nucleotide sequence encoding the amino acid
      sequence of the mature form of Trichoderma reesei Prb1 protease.

<400> SEQUENCE: 9
gctttgacca ctcagactgg cgcccccctgg ggactcggca ctgtctccca ccgcacaccc      60
ggctcaacta gctacatcta tgacacttcg gctggtagcg gaacattcgc ctatgttgtt     120
gactctggaa tcaacattgc tcaccagcaa ttcggcggac gtgccagcct cggctacaac     180

```
gccgctggtg gagatcatgt cgacactctc ggccacggca cgcacgtttc cggaactatc    240
ggtggctcta cctatggtgt tgctaagcag gtaagctgct tcattatact tcttcctttg    300
cagtgcgggc cttgagcacg ccgggctgac tctgtaacga aaggccagct taatctccgt    360
caaggtcttc cagggcaaca cgccagcac ctcggtcatc cttgacggct ataattgggc    420
cgtgaacgac attgtctccc gcaaccgcgc agcaagtct gccatcaaca tgtctctcgg    480
tggcccggcc tcttccacct gggctacggc gatcaatgca gcctttaaca agggcgtcct    540
gacgatcgtg gccgccggca atggtgacgc tcttggaaac cctcagcctg tctccagtac    600
ttctccagcc aatgtgccca cgccatcac cgtcgcagcc cttgacatta actggcgcac    660
cgcttccttc accaattatg gtgctggcgt tgacgtcttc gctcctggtg tcaacatcct    720
gtcttcgtgg atcggctcta acactgccac aaacacgatt agcggcacct ccatggccac    780
tcctcacgtt gtcggcctcg ctctttacct gcaggctctt gagggcctta gcacccccgac   840 tgctgtaacc aaccgcatca aggccttggc tactactgga cgcgtcaccg gcagtctgaa    900
tggcagcccc aacactctca tcttcaacgg gaacagtgct taa                      943
```

<210> SEQ ID NO 10
<211> LENGTH: 289
<212> TYPE: PRT
<213> ORGANISM: Trichoderma reesei
<220> FEATURE:
<221> NAME/KEY: MISC_FEATURE
<223> OTHER INFORMATION: The amino acid sequence of the mature form of Trichoderma reesei Prb1 protease including amino acids Ala121 to Ala409 of the full length enzyme.

<400> SEQUENCE: 10

```
Ala Leu Thr Thr Gln Thr Gly Ala Pro Trp Gly Leu Gly Thr Val Ser
1               5                   10                  15

His Arg Thr Pro Gly Ser Thr Ser Tyr Ile Tyr Asp Thr Ser Ala Gly
            20                  25                  30

Ser Gly Thr Phe Ala Tyr Val Val Asp Ser Gly Ile Asn Ile Ala His
        35                  40                  45

Gln Gln Phe Gly Gly Arg Ala Ser Leu Gly Tyr Asn Ala Ala Gly Gly
    50                  55                  60

Asp His Val Asp Thr Leu Gly His Gly Thr His Val Ser Gly Thr Ile
65                  70                  75                  80

Gly Gly Ser Thr Tyr Gly Val Ala Lys Gln Ala Ser Leu Ile Ser Val
                85                  90                  95

Lys Val Phe Gln Gly Asn Ser Ala Ser Thr Ser Val Ile Leu Asp Gly
            100                 105                 110

Tyr Asn Trp Ala Val Asn Asp Ile Val Ser Arg Asn Arg Ala Ser Lys
        115                 120                 125

Ser Ala Ile Asn Met Ser Leu Gly Gly Pro Ala Ser Ser Thr Trp Ala
    130                 135                 140

Thr Ala Ile Asn Ala Ala Phe Asn Lys Gly Val Leu Thr Ile Val Ala
145                 150                 155                 160

Ala Gly Asn Gly Asp Ala Leu Gly Asn Pro Gln Pro Val Ser Ser Thr
                165                 170                 175

Ser Pro Ala Asn Val Pro Asn Ala Ile Thr Val Ala Ala Leu Asp Ile
            180                 185                 190

Asn Trp Arg Thr Ala Ser Phe Thr Asn Tyr Gly Ala Gly Val Asp Val
        195                 200                 205

Phe Ala Pro Gly Val Asn Ile Leu Ser Ser Trp Ile Gly Ser Asn Thr
```

```
                  210                 215                 220
Ala Thr Asn Thr Ile Ser Gly Thr Ser Met Ala Thr Pro His Val Val
225                 230                 235                 240

Gly Leu Ala Leu Tyr Leu Gln Ala Leu Glu Gly Leu Ser Thr Pro Thr
                245                 250                 255

Ala Val Thr Asn Arg Ile Lys Ala Leu Ala Thr Thr Gly Arg Val Thr
                260                 265                 270

Gly Ser Leu Asn Gly Ser Pro Asn Thr Leu Ile Phe Asn Gly Asn Ser
            275                 280                 285

Ala

<210> SEQ ID NO 11
<211> LENGTH: 1292
<212> TYPE: DNA
<213> ORGANISM: Fusarium graminearum
<220> FEATURE:
<221> NAME/KEY: misc_feature
<223> OTHER INFORMATION: The nucleotide sequence of the full-length
      Fusarium graminearum ALKO1726 protease gene Fg prtS8A.

<400> SEQUENCE: 11
atgaccagct tccgccgtct tgctctcgct cttggagctc tgctccctgc agtcctcgcc       60
gctcctactg agaagcgaca ggaactcact gccgcgcctg acaagtacat catcactctc      120
aagcccgagg ctactgagaa caagatcgag gctcacttga actgggtcag cgatgtccac      180
cgccgcagcc tgaacaagcg tgacacttct ggtgttgaga agaagttcaa catcagcagc      240
tggaacgcct actctggcga gttcgacaag gctaccattg atgagatcaa gaagagcccc      300
gaggttgctt tcgtcgagcc tgactacact gtctacctcg acttcgagac cgaactcact      360
gaccgtgctc tgaccaccca gagcggcgct ccttggggtc tcgcctccat ctcccgccga      420
acctccggtg cagcaccta cacctacgac accactgccg gctccggttc ttacggatac      480
gtcgttgaca gcggcatcaa cgtcaaccac cgagacttcg gtggccgtgc ttctctcggt      540
tacaacgctg ccggtggttc ccacgtcgac accctgggcc acggtaccca cgttgctgga      600
accattgctt cttccaccta cggtgttgcc aaggctgtaa gtaaacccca cattatatgg      660
tagcatctga actttatact tactatcttt aggccaacgt catctctgtc aaggtcttca      720
ctggcaacag tgcctctacc tccactatcc tcgctggttt caactgggct gtcaacgaca      780
tcacttccaa gggccgtgct ggtcgctctg tcatcaacat gtctctcggc ggtccctctg      840
ctcagacctg gaccactgct atcaacgctg cctacaactc tggtgtcctc tccgttgttg      900
ctgccggtaa cggtgacgat ttcggccgcc ctcttcccgt ctctggccag tctcctgcca      960
acgtccccaa cgctctgacc gttgctgcca ttgactccag ctggcgcact gcctcttcca     1020
ccaactacgg tgccggtgtt gatgtcttcg cccctggtgt cggcatcctc tccacctggt     1080
acacctccaa cactgctacc aactccatca gcggtaccc catggcctgc ctcacgttg      1140 ctggtcttgc tctctacctc caggttctcg agggtcttc cacccctgct gccgtcacca     1200
accgcatcaa ggctcttgct accactggcc gtgtcactgg cacccctcaac ggcagcccca     1260 acctgatcgc cttcaacggt gcctctactt aa                                   1292

<210> SEQ ID NO 12
<211> LENGTH: 411
<212> TYPE: PRT
<213> ORGANISM: Fusarium graminearum
<220> FEATURE:
<221> NAME/KEY: MISC_FEATURE
<223> OTHER INFORMATION: The deduced amino acid sequence of the
``` full-length Fusarium graminearum ALKO1726 protease (Fg_ALKO1726) including amino acids from Met1 to Thr411.

<400> SEQUENCE: 12

```
Met Thr Ser Phe Arg Arg Leu Ala Leu Ala Leu Gly Ala Leu Leu Pro
1               5                   10                  15

Ala Val Leu Ala Ala Pro Thr Glu Lys Arg Gln Glu Leu Thr Ala Ala
            20                  25                  30

Pro Asp Lys Tyr Ile Ile Thr Leu Lys Pro Glu Ala Thr Glu Asn Lys
        35                  40                  45

Ile Glu Ala His Leu Asn Trp Val Ser Asp Val His Arg Arg Ser Leu
50                  55                  60

Asn Lys Arg Asp Thr Ser Gly Val Glu Lys Lys Phe Asn Ile Ser Ser
65                  70                  75                  80

Trp Asn Ala Tyr Ser Gly Glu Phe Asp Lys Ala Thr Ile Asp Glu Ile
                85                  90                  95

Lys Lys Ser Pro Glu Val Ala Phe Val Glu Pro Asp Tyr Thr Val Tyr
            100                 105                 110

Leu Asp Phe Glu Thr Glu Leu Thr Asp Arg Ala Leu Thr Thr Gln Ser
        115                 120                 125

Gly Ala Pro Trp Gly Leu Ala Ser Ile Ser Arg Arg Thr Ser Gly Gly
130                 135                 140

Ser Thr Tyr Thr Tyr Asp Thr Thr Ala Gly Gly Ser Tyr Gly Tyr
145                 150                 155                 160

Val Val Asp Ser Gly Ile Asn Val Asn His Arg Asp Phe Gly Gly Arg
                165                 170                 175

Ala Ser Leu Gly Tyr Asn Ala Ala Gly Gly Ser His Val Asp Thr Leu
            180                 185                 190

Gly His Gly Thr His Val Ala Gly Thr Ile Ala Ser Ser Thr Tyr Gly
        195                 200                 205

Val Ala Lys Ala Ala Asn Val Ile Ser Val Lys Val Phe Thr Gly Asn
210                 215                 220

Ser Ala Ser Thr Ser Thr Ile Leu Ala Gly Phe Asn Trp Ala Val Asn
225                 230                 235                 240

Asp Ile Thr Ser Lys Gly Arg Ala Gly Arg Ser Val Ile Asn Met Ser
                245                 250                 255

Leu Gly Gly Pro Ser Ala Gln Thr Trp Thr Ala Ile Asn Ala Ala
            260                 265                 270

Tyr Asn Ser Gly Val Leu Ser Val Val Ala Ala Gly Asn Gly Asp Asp
        275                 280                 285

Phe Gly Arg Pro Leu Pro Val Ser Gly Gln Ser Pro Ala Asn Val Pro
290                 295                 300

Asn Ala Leu Thr Val Ala Ala Ile Asp Ser Ser Trp Arg Thr Ala Ser
305                 310                 315                 320

Phe Thr Asn Tyr Gly Ala Gly Val Asp Val Phe Ala Pro Gly Val Gly
                325                 330                 335

Ile Leu Ser Thr Trp Tyr Thr Ser Asn Thr Ala Thr Asn Ser Ile Ser
            340                 345                 350

Gly Thr Ser Met Ala Cys Pro His Val Ala Gly Leu Ala Leu Tyr Leu
        355                 360                 365

Gln Val Leu Glu Gly Leu Ser Thr Pro Ala Ala Val Thr Asn Arg Ile
370                 375                 380

Lys Ala Leu Ala Thr Thr Gly Arg Val Thr Gly Thr Leu Asn Gly Ser
385                 390                 395                 400
```

Pro Asn Leu Ile Ala Phe Asn Gly Ala Ser Thr
            405                 410

<210> SEQ ID NO 13
<211> LENGTH: 1232
<212> TYPE: DNA
<213> ORGANISM: Fusarium graminearum
<220> FEATURE:
<221> NAME/KEY: misc_feature
<223> OTHER INFORMATION: The nucleotide sequence encoding the amino acid
      sequence of the proenzyme form of Fusarium graminearum ALKO1726
      protease.

<400> SEQUENCE: 13

```
gctcctactg agaagcgaca ggaactcact gccgcgcctg acaagtacat catcactctc      60
aagcccgagg ctactgag

```
Thr Ser Gly Val Glu Lys Lys Phe Asn Ile Ser Ser Trp Asn Ala Tyr
 50                  55                  60
Ser Gly Glu Phe Asp Lys Ala Thr Ile Asp Glu Ile Lys Lys Ser Pro
 65                  70                  75                  80
Glu Val Ala Phe Val Glu Pro Asp Tyr Thr Val Tyr Leu Asp Phe Glu
                 85                  90                  95
Thr Glu Leu Thr Asp Arg Ala Leu Thr Thr Gln Ser Gly Ala Pro Trp
                100                 105                 110
Gly Leu Ala Ser Ile Ser Arg Arg Thr Ser Gly Gly Ser Thr Tyr Thr
            115                 120                 125
Tyr Asp Thr Thr Ala Gly Ser Gly Ser Tyr Gly Tyr Val Val Asp Ser
        130                 135                 140
Gly Ile Asn Val Asn His Arg Asp Phe Gly Arg Ala Ser Leu Gly
145                 150                 155                 160
Tyr Asn Ala Ala Gly Gly Ser His Val Asp Thr Leu Gly His Gly Thr
                165                 170                 175
His Val Ala Gly Thr Ile Ala Ser Ser Thr Tyr Gly Val Ala Lys Ala
            180                 185                 190
Ala Asn Val Ile Ser Val Lys Val Phe Thr Gly Asn Ser Ala Ser Thr
        195                 200                 205
Ser Thr Ile Leu Ala Gly Phe Asn Trp Ala Val Asn Asp Ile Thr Ser
210                 215                 220
Lys Gly Arg Ala Gly Arg Ser Val Ile Asn Met Ser Leu Gly Gly Pro
225                 230                 235                 240
Ser Ala Gln Thr Trp Thr Thr Ala Ile Asn Ala Ala Tyr Asn Ser Gly
                245                 250                 255
Val Leu Ser Val Val Ala Ala Gly Asn Gly Asp Asp Phe Gly Arg Pro
            260                 265                 270
Leu Pro Val Ser Gly Gln Ser Pro Ala Asn Val Pro Asn Ala Leu Thr
        275                 280                 285
Val Ala Ala Ile Asp Ser Ser Trp Arg Thr Ala Ser Phe Thr Asn Tyr
290                 295                 300
Gly Ala Gly Val Asp Val Phe Ala Pro Gly Val Gly Ile Leu Ser Thr
305                 310                 315                 320
Trp Tyr Thr Ser Asn Thr Ala Thr Asn Ser Ile Ser Gly Thr Ser Met
                325                 330                 335
Ala Cys Pro His Val Ala Gly Leu Ala Leu Tyr Leu Gln Val Leu Glu
            340                 345                 350
Gly Leu Ser Thr Pro Ala Ala Val Thr Asn Arg Ile Lys Ala Leu Ala
        355                 360                 365
Thr Thr Gly Arg Val Thr Gly Thr Leu Asn Gly Ser Pro Asn Leu Ile
370                 375                 380
Ala Phe Asn Gly Ala Ser Thr
385                 390

<210> SEQ ID NO 15
<211> LENGTH: 926
<212> TYPE: DNA
<213> ORGANISM: Fusarium graminearum
<220> FEATURE:
<221> NAME/KEY: misc_feature
<223> OTHER INFORMATION: The nucleotide sequence encoding the amino acid
      sequence of the mature form of Fusarium graminearum ALKO1726
      protease.

<400> SEQUENCE: 15
gctctgacca cccagagcgg cgctccttgg ggtctcgcct ccatctcccg ccgaacctcc      60
```

```
ggtggcagca cctacaccta cgacaccact gccggctccg gttcttacgg atacgtcgtt    120
gacagcggca tcaacgtcaa ccaccgagac ttcggtggcc gtgcttctct cggttacaac    180
gctgccggtg ttcccacgt cgacaccctg ggccacggta cccacgttgc tggaaccatt    240
gcttcttcca cctacggtgt tgccaaggct gtaagtaaac cccacattat atggtagcat    300
ctgaacttta tacttactat ctttaggcca acgtcatctc tgtcaaggtc ttcactggca    360
acagtgcctc tacctccact atcctcgctg gtttcaactg ggctgtcaac gacatcactt    420
ccaagggccg tgctggtcgc tctgtcatca acatgtctct cggcggtccc tctgctcaga    480
cctggaccac tgctatcaac gctgcctaca actctggtgt cctctccgtt gttgctgccg    540
gtaacggtga cgatttcggc cgccctcttc ccgtctctgg ccagtctcct gccaacgtcc    600
ccaacgctct gaccgttgct gccattgact ccagctggcg cactgcctct ttcaccaact    660
acggtgccgg tgttgatgtc ttcgcccctg gtgtcggcat cctctccacc tggtacacct    720
ccaacactgc taccaactcc atcagcggta cctccatggc ctgccctcac gttgctggtc    780
ttgctctcta cctccaggtt ctcgagggtc tttccacccc tgctgccgtc accaaccgca    840
tcaaggctct tgctaccact ggccgtgtca ctggcaccct caacggcagc cccaacctga    900
tcgccttcaa cggtgcctct acttaa                                         926
```

<210> SEQ ID NO 16
<211> LENGTH: 289
<212> TYPE: PRT
<213> ORGANISM: Fusarium graminearum
<220> FEATURE:
<221> NAME/KEY: MISC_FEATURE
<223> OTHER INFORMATION: The amino acid sequence of the mature form of
      Fusarium graminearum ALKO1726 protease including amino acids
      Ala123 to Thr411 of the full length enzyme.

<400> SEQUENCE: 16

```
Ala Leu Thr Thr Gln Ser Gly Ala Pro Trp Gly Leu Ala Ser Ile Ser
1               5                   10                  15

Arg Arg Thr Ser Gly Gly Ser Thr Tyr Thr Tyr Asp Thr Thr Ala Gly
            20                  25                  30

Ser Gly Ser Tyr Gly Tyr Val Val Asp Ser Gly Ile Asn Val Asn His
        35                  40                  45

Arg Asp Phe Gly Gly Arg Ala Ser Leu Gly Tyr Asn Ala Ala Gly Gly
    50                  55                  60

Ser His Val Asp Thr Leu Gly His Gly Thr His Val Ala Gly Thr Ile
65                  70                  75                  80

Ala Ser Ser Thr Tyr Gly Val Ala Lys Ala Ala Asn Val Ile Ser Val
                85                  90                  95

Lys Val Phe Thr Gly Asn Ser Ala Ser Thr Ser Thr Ile Leu Ala Gly
            100                 105                 110

Phe Asn Trp Ala Val Asn Asp Ile Thr Ser Lys Gly Arg Ala Gly Arg
        115                 120                 125

Ser Val Ile Asn Met Ser Leu Gly Gly Pro Ser Ala Gln Thr Trp Thr
    130                 135                 140

Thr Ala Ile Asn Ala Ala Tyr Asn Ser Gly Val Leu Ser Val Val Ala
145                 150                 155                 160

Ala Gly Asn Gly Asp Asp Phe Gly Arg Pro Leu Pro Val Ser Gly Gln
                165                 170                 175

Ser Pro Ala Asn Val Pro Asn Ala Leu Thr Val Ala Ala Ile Asp Ser
            180                 185                 190
```

```
Ser Trp Arg Thr Ala Ser Phe Thr Asn Tyr Gly Ala Gly Val Asp Val
        195                 200                 205

Phe Ala Pro Gly Val Gly Ile Leu Ser Thr Trp Tyr Thr Ser Asn Thr
        210                 215                 220

Ala Thr Asn Ser Ile Ser Gly Thr Ser Met Ala Cys Pro His Val Ala
225                 230                 235                 240

Gly Leu Ala Leu Tyr Leu Gln Val Leu Glu Gly Leu Ser Thr Pro Ala
                245                 250                 255

Ala Val Thr Asn Arg Ile Lys Ala Leu Ala Thr Thr Gly Arg Val Thr
            260                 265                 270

Gly Thr Leu Asn Gly Ser Pro Asn Leu Ile Ala Phe Asn Gly Ala Ser
        275                 280                 285

Thr
```